US010586353B2

(12) United States Patent
Yoshimura et al.

(10) Patent No.: US 10,586,353 B2
(45) Date of Patent: Mar. 10, 2020

(54) PLANT INFORMATION ACQUISITION SYSTEM, PLANT INFORMATION ACQUISITION DEVICE, PLANT INFORMATION ACQUISITION METHOD, CROP MANAGEMENT SYSTEM AND CROP MANAGEMENT METHOD

(71) Applicant: MAXELL HOLDINGS, LTD., Oyamazaki-cho (JP)

(72) Inventors: Hiroyuki Yoshimura, Ibaraki (JP); Kanryo Terasawa, Ibaraki (JP); Masashi Yoshimura, Ibarak (JP)

(73) Assignee: MAXELL HOLDINGS, LTD., Kyoto (JP)

(*) Notice: Subject to any disclaimer, the term of this patent is extended or adjusted under 35 U.S.C. 154(b) by 0 days.

(21) Appl. No.: 15/511,059

(22) PCT Filed: Jan. 12, 2016

(86) PCT No.: PCT/JP2016/050687

§ 371 (c)(1),
(2) Date: Mar. 14, 2017

(87) PCT Pub. No.: WO2016/111376

PCT Pub. Date: Jul. 14, 2016

(65) Prior Publication Data

US 2017/0358106 A1 Dec. 14, 2017

(30) Foreign Application Priority Data

Jan. 9, 2015 (JP) ................................ 2015-003086
Jul. 6, 2015 (JP) ................................ 2015-135666

(51) Int. Cl.
*G06K 9/00* (2006.01)
*G06T 7/90* (2017.01)
(Continued)

(52) U.S. Cl.
CPC ................. *G06T 7/90* (2017.01); *A01G 7/00* (2013.01); *A01G 7/045* (2013.01); *G01J 3/2803* (2013.01);
(Continued)

(58) Field of Classification Search
None
See application file for complete search history.

(56) References Cited

U.S. PATENT DOCUMENTS 5,859,435 A * 1/1999 Satake ................ G01N 21/359
250/339.01
6,080,950 A * 6/2000 Jalink ................... A01C 1/025
209/576

(Continued)

FOREIGN PATENT DOCUMENTS

JP H08-327538 A 12/1996
JP H10-090066 A 4/1998

(Continued)

OTHER PUBLICATIONS

Su et al., "Simultaneous estimation of chlorophyll a and lipid contents in microalgae by three-color analysis", Wiley InterScience, Aug. 17, 2007.*

(Continued)

*Primary Examiner* — Soo Jin Park
(74) *Attorney, Agent, or Firm* — Oliff PLC

(57) ABSTRACT

Information of plant based on color of a surface of plant is acquired from image data obtained by imaging plant, allowing to acquire information of plant at low cost, compared to chlorophyll meter or spectroscopic analyzer. In crop production like rice plant, fertilization management including fertilizer application management like fertilizer amount determination, or other agricultural works, is supported through a smart phone or the like based on data to be
(Continued)

observed, like converted leaf color value is calculated from image data obtained by crop imaging. Camera is connected to smart phone. Converted leaf color value can be obtained from image data obtained by imaging leaf of rice plant by camera. Converted leaf color value is transmitted to management server, for example, amount information of applied fertilizer is required in case where converted leaf color value is less than standard, can be obtained as management information for fertilizer application management.

20 Claims, 37 Drawing Sheets

(51) Int. Cl.

| | |
|---|---|
| ***G06F 16/951*** | (2019.01) |
| ***G06F 16/583*** | (2019.01) |
| ***G01J 3/51*** | (2006.01) |
| ***A01G 7/04*** | (2006.01) |
| ***G03B 15/00*** | (2006.01) |
| ***G01N 21/25*** | (2006.01) |
| ***G06K 9/62*** | (2006.01) |
| ***G01N 33/00*** | (2006.01) |
| ***G06T 7/00*** | (2017.01) |
| ***G01N 21/27*** | (2006.01) |
| ***G01J 3/28*** | (2006.01) |
| ***A01G 7/00*** | (2006.01) |
| ***G03B 11/04*** | (2006.01) |
| ***G06K 9/46*** | (2006.01) |
| ***H04N 5/225*** | (2006.01) |
| *G01N 21/84* | (2006.01) |
| *G01N 21/88* | (2006.01) |
| *G06K 9/20* | (2006.01) |

(52) U.S. Cl.

CPC .............. *G01J 3/51* (2013.01); *G01N 21/251* (2013.01); *G01N 21/274* (2013.01); *G01N 33/0098* (2013.01); *G03B 11/04* (2013.01); *G03B 15/00* (2013.01); *G06F 16/5838* (2019.01); *G06F 16/951* (2019.01); *G06K 9/00979* (2013.01); *G06K 9/4652* (2013.01); *G06K 9/6202* (2013.01); *G06T 7/0012* (2013.01); *H04N 5/2256* (2013.01); *G01N 2021/8466* (2013.01); *G01N 2021/8845* (2013.01); *G01N 2201/024* (2013.01); *G03B 11/045* (2013.01); *G06K 9/2027* (2013.01); *G06K 9/2036* (2013.01); *G06T 7/0002* (2013.01); *G06T 2207/10024* (2013.01); *G06T 2207/30188* (2013.01); *Y02P 60/146* (2015.11)

(56) References Cited

U.S. PATENT DOCUMENTS

| | | | | |
|---|---|---|---|---|
| 8,061,080 B2 * | 11/2011 | Loebl | A01G 9/26 | 47/58.1 LS |
| 8,249,308 B2 * | 8/2012 | Lussier | G01J 3/02 | 356/300 |
| 9,265,204 B2 * | 2/2016 | Younis | A01G 25/16 | |
| 2010/0111369 A1 * | 5/2010 | Lussier | G01J 3/02 | 382/110 |
| 2012/0297674 A1 * | 11/2012 | MacKenzie | A01B 79/005 | 47/58.1 R |
| 2013/0153673 A1 * | 6/2013 | Younis | A01G 25/165 | 239/1 |
| 2014/0168412 A1 * | 6/2014 | Shulman | H04N 7/18 | 348/89 |
| 2015/0027044 A1 * | 1/2015 | Redden | A01G 22/00 | 47/58.1 R |
| 2016/0113213 A1 * | 4/2016 | Berinsky | A01G 7/045 | 47/58.1 LS |

FOREIGN PATENT DOCUMENTS

| | | | |
|---|---|---|---|
| JP | H11-235124 | A | 8/1999 |
| JP | 2004-298069 | A | 10/2004 |
| JP | 4012554 | B2 | 11/2007 |
| JP | 2013-158277 | A | 8/2013 |

OTHER PUBLICATIONS

Hu et al., "Assessment of chlorophyll content based on image color analysis, comparison with SPAD-502", ICIECS 2010.*

Riccardi et al., "Non-destructive evaluation of chlorophyll content in quinoa and amaranth leaves by simple and multiple regression analysis of RGB image components", Photosynth Res (2014) 120:263-272.*

Wang et al., "Plant image analysis machine vision system in greenhouse", 8th International Conference on Computer and Computing Technologies in Agriculture (CCTA), Sep. 2014, Beijing, China.*

Apr. 19, 2016 International Search Report issued with International Patent Application No. PCT/JP2016/050687.

Oct. 23, 2018 Office Action issue in Japanese Patent Application No. 2015-135666.

Oct. 23, 2018 Office Action issue in Japanese Patent Application No. 2015-003086.

* cited by examiner

[Fig. 1]
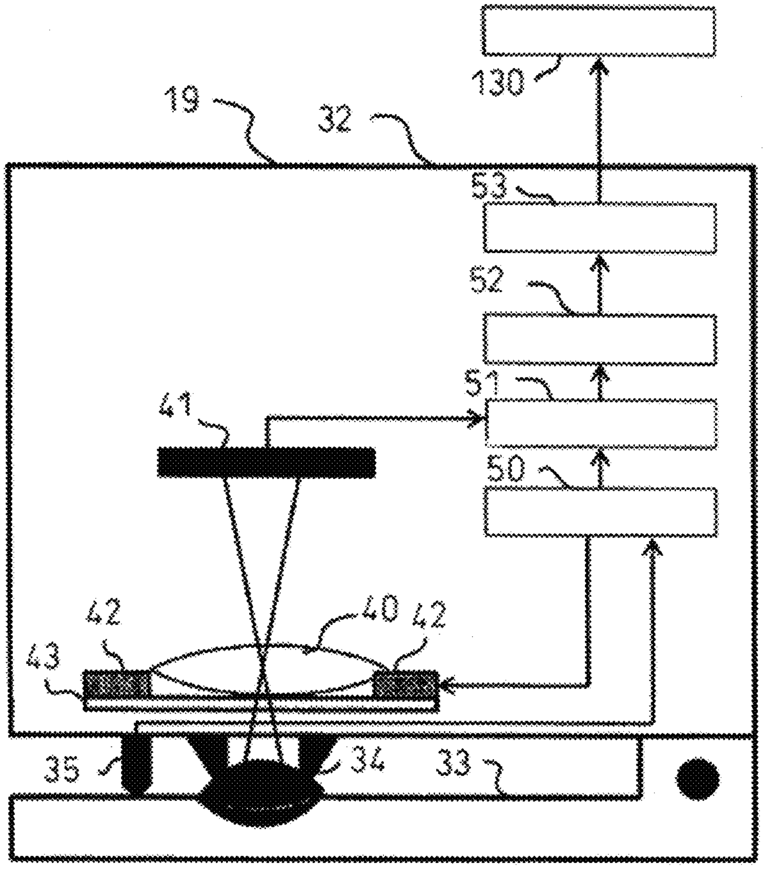

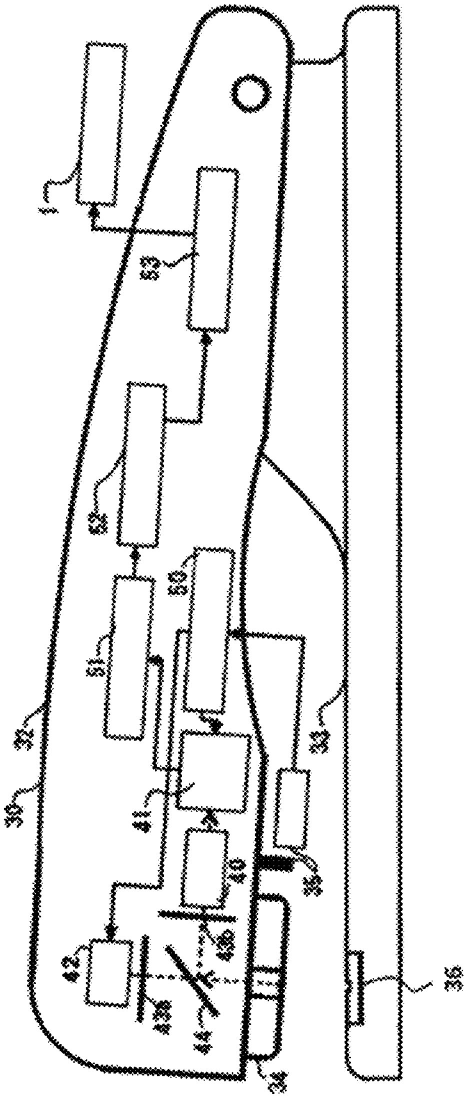
[Fig. 2]

[Fig. 3]
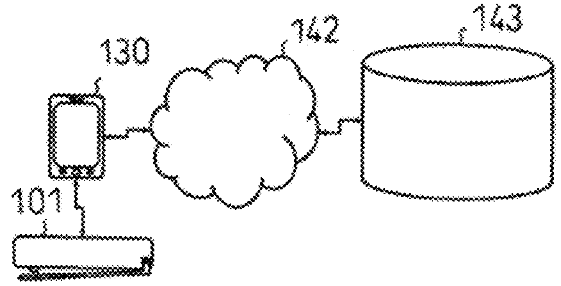

[Fig. 4]
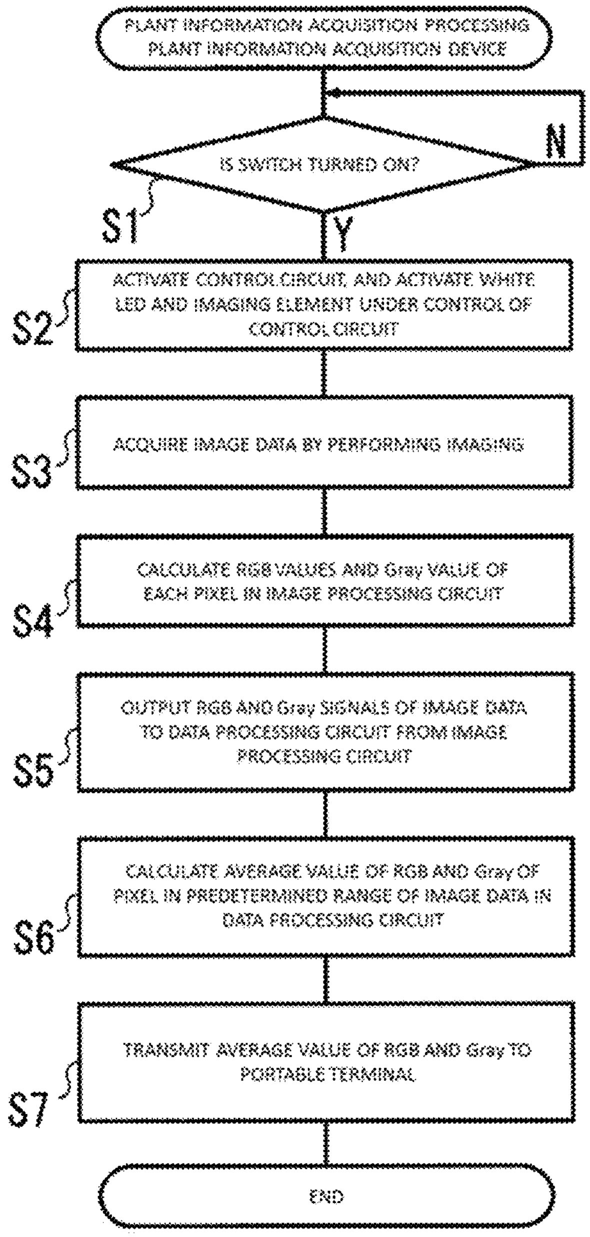

[Fig. 5]
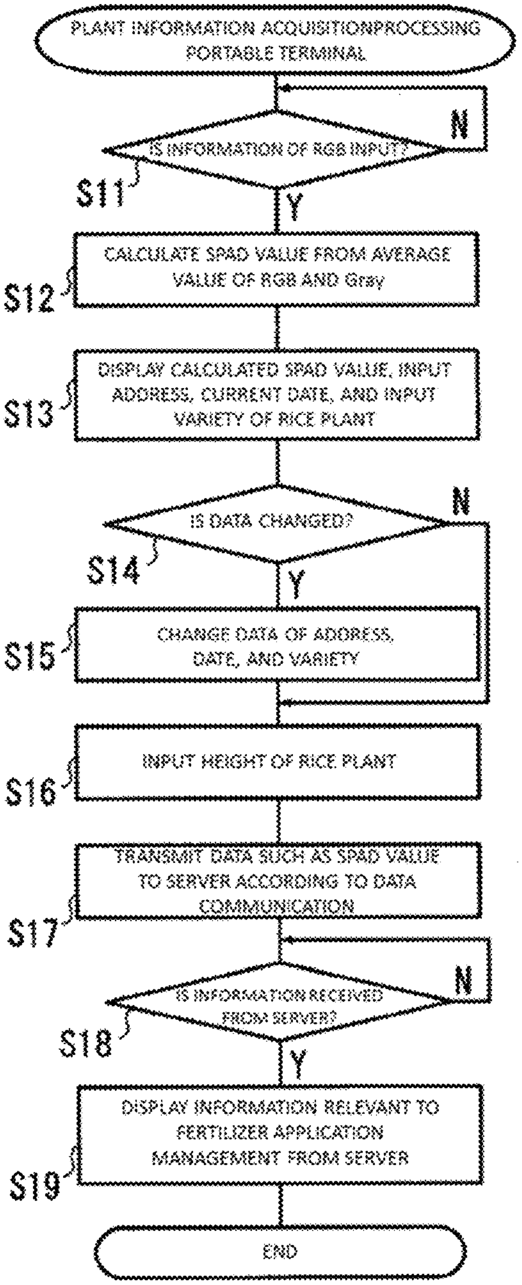

[Fig. 6]
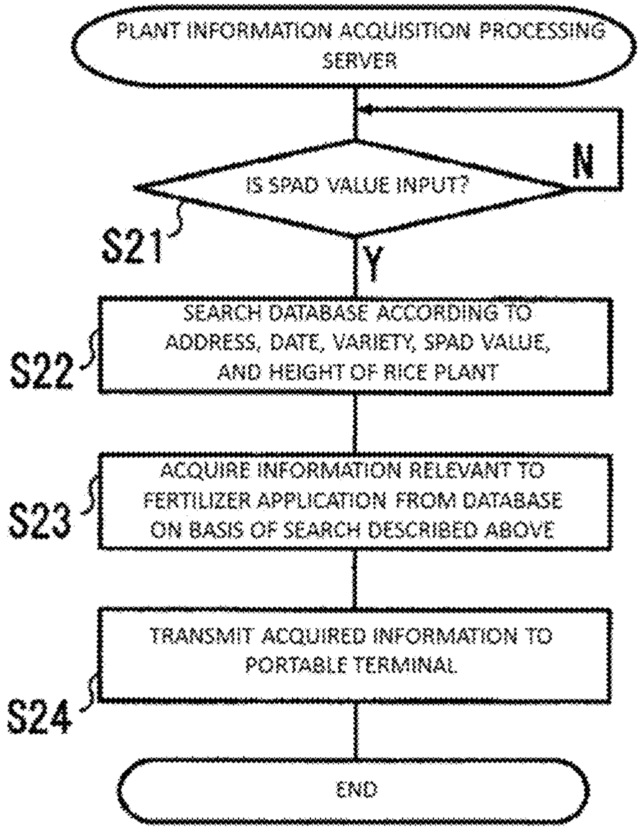

[Fig. 7]
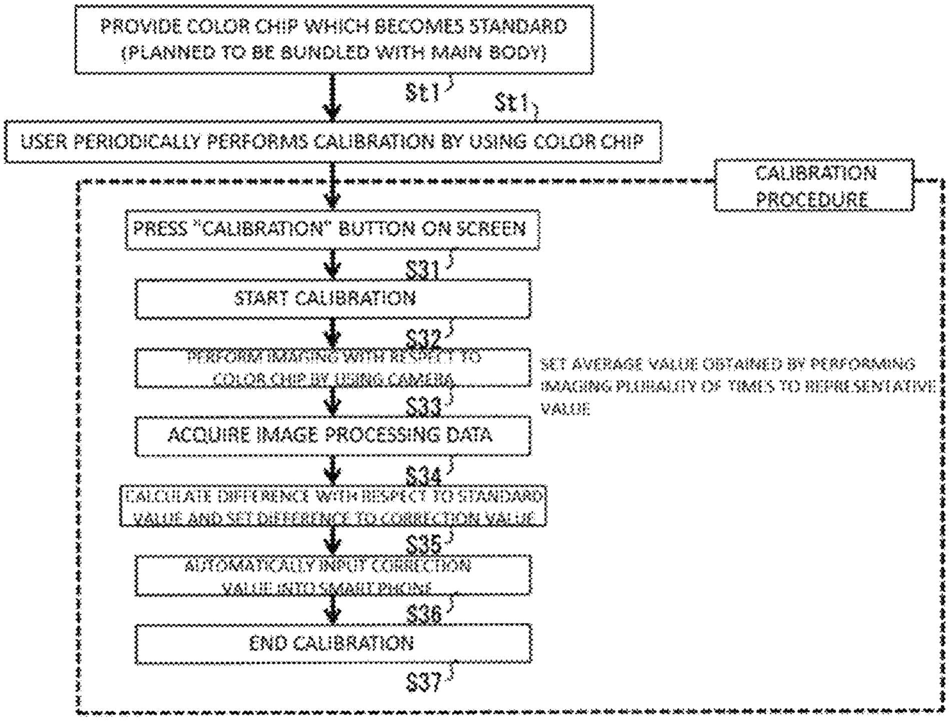

[Fig. 8]
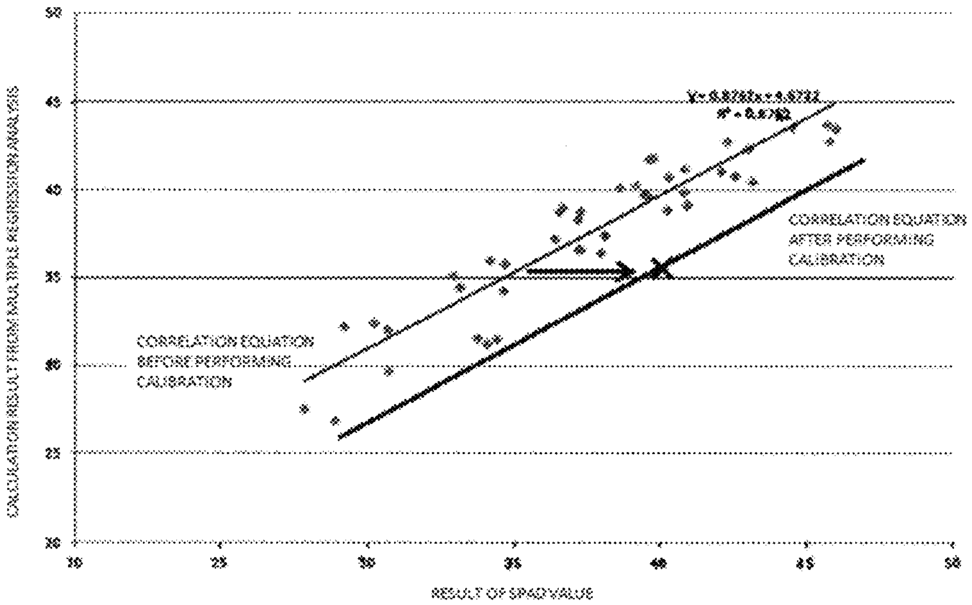

[Fig. 9]
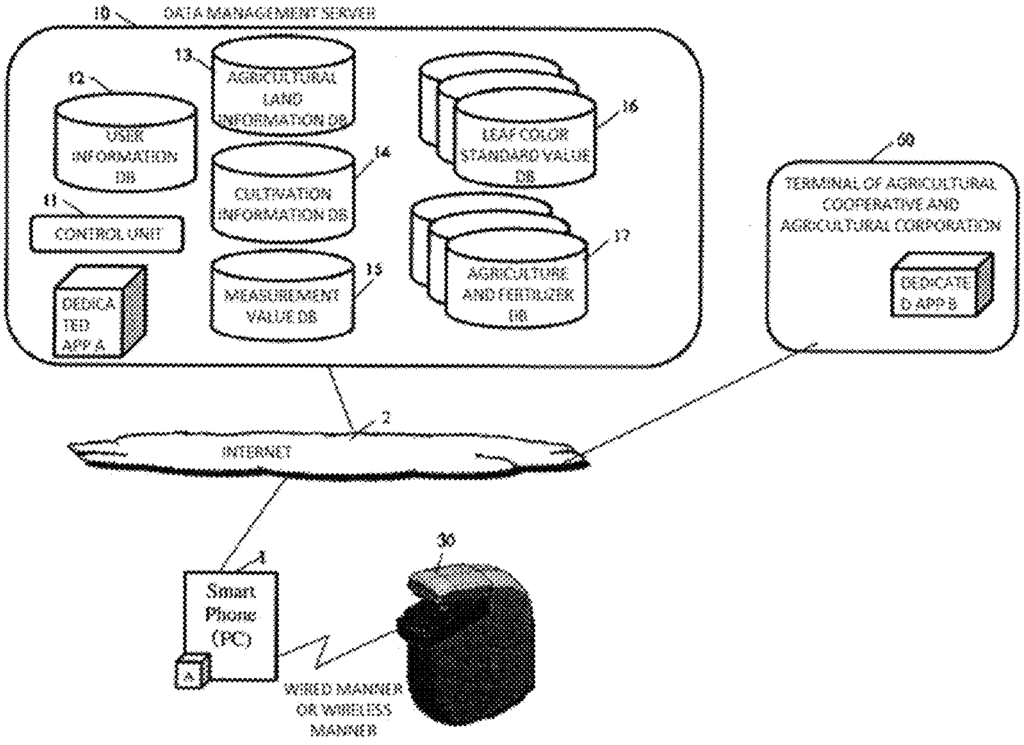

[Fig. 10]
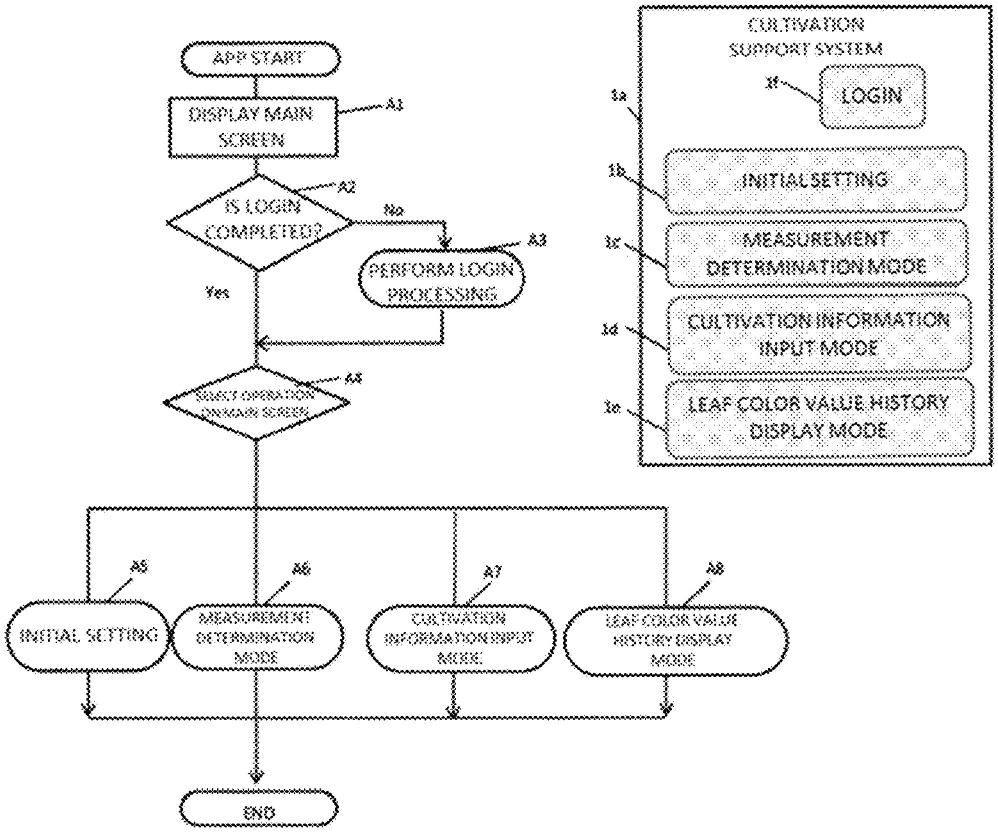

[Fig. 11]
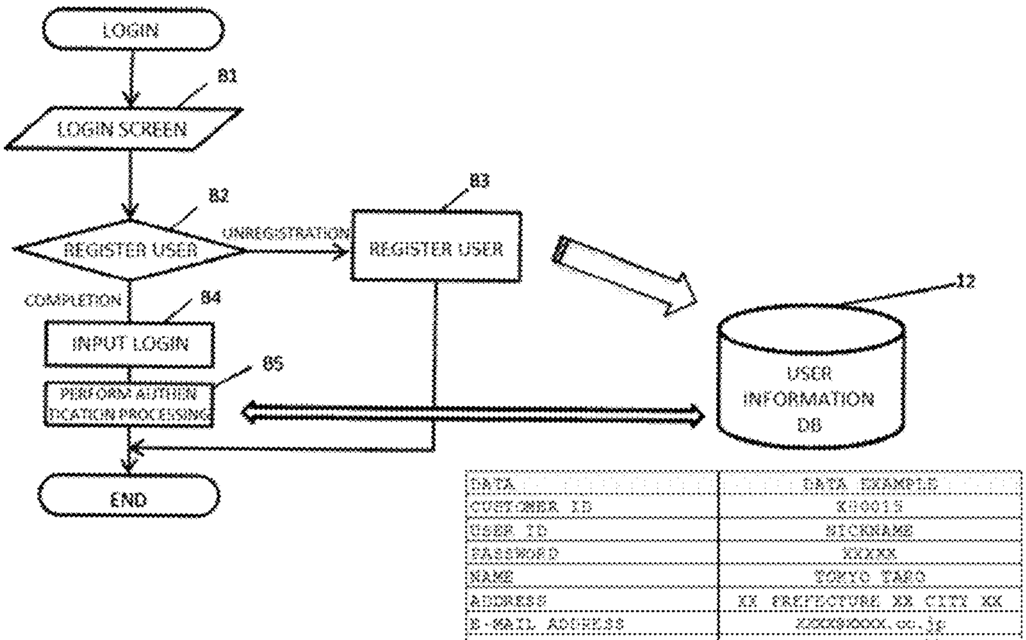
| DATA | DATA EXAMPLE |
|---|---|
| CUSTOMER ID | K00015 |
| USER ID | NICKNAME |
| PASSWORD | XXXXX |
| NAME | TOKYO TARO |
| ADDRESS | XX PREFECTURE XX CITY XX |
| E-MAIL ADDRESS | XXXX@XXXX.co.jp |
| CHARGING INFORMATION | [illegible] |
| CONTRACT PERIOD | 2018/3/31 |
| CAMERA SERIAL No. | 01020005 |
| AFFILIATED GROUP | JA AKITA XXX |

[Fig. 12]

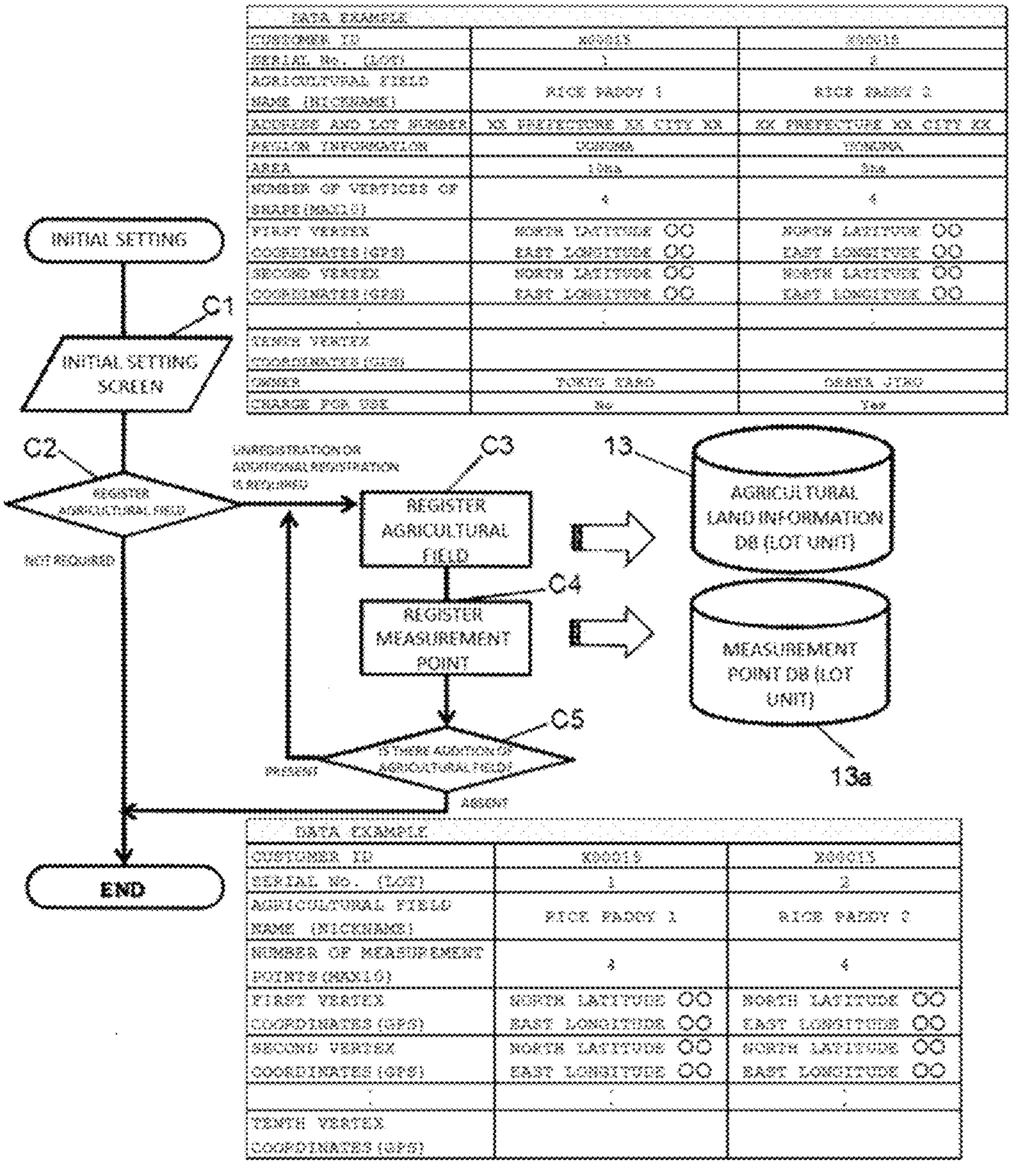

| DATA EXAMPLE | | |
|---|---|---|
| CUSTOMER ID | [illegible] | [illegible] |
| SERIAL No. (LOT) | 1 | 2 |
| AGRICULTURAL FIELD NAME (NICKNAME) | RICE PADDY 1 | RICE PADDY 2 |
| ADDRESS AND LOT NUMBER | XX PREFECTURE XX CITY XX | XX PREFECTURE XX CITY XX |
| REGION INFORMATION | [illegible] | [illegible] |
| AREA | [illegible] | [illegible] |
| NUMBER OF VERTICES OF SHAPE (MAX10) | 4 | 4 |
| FIRST VERTEX COORDINATES (GPS) | NORTH LATITUDE ○○ EAST LONGITUDE ○○ | NORTH LATITUDE ○○ EAST LONGITUDE ○○ |
| SECOND VERTEX COORDINATES (GPS) | NORTH LATITUDE ○○ EAST LONGITUDE ○○ | NORTH LATITUDE ○○ EAST LONGITUDE ○○ |
| ⋮ | ⋮ | ⋮ |
| TENTH VERTEX COORDINATES (GPS) | | |
| OWNER | TOKYO TARO | OSAKA JIRO |
| CHARGE FOR USE | No | Yes |

| DATA EXAMPLE | | |
|---|---|---|
| CUSTOMER ID | [illegible] | [illegible] |
| SERIAL No. (LOT) | 1 | 2 |
| AGRICULTURAL FIELD NAME (NICKNAME) | RICE PADDY 1 | RICE PADDY 2 |
| NUMBER OF MEASUREMENT POINTS (MAX10) | [illegible] | 4 |
| FIRST VERTEX COORDINATES (GPS) | NORTH LATITUDE ○○ EAST LONGITUDE ○○ | NORTH LATITUDE ○○ EAST LONGITUDE ○○ |
| SECOND VERTEX COORDINATES (GPS) | NORTH LATITUDE ○○ EAST LONGITUDE ○○ | NORTH LATITUDE ○○ EAST LONGITUDE ○○ |
| ⋮ | ⋮ | ⋮ |
| TENTH VERTEX COORDINATES (GPS) | | |

[Fig. 13]
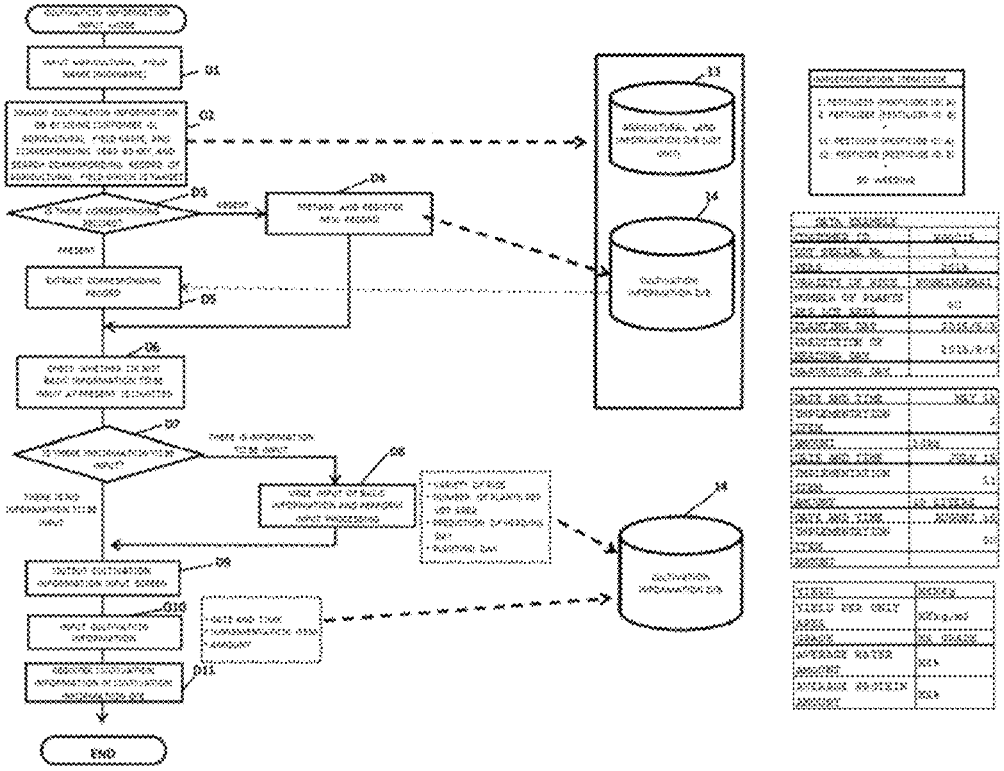

[Fig. 14]
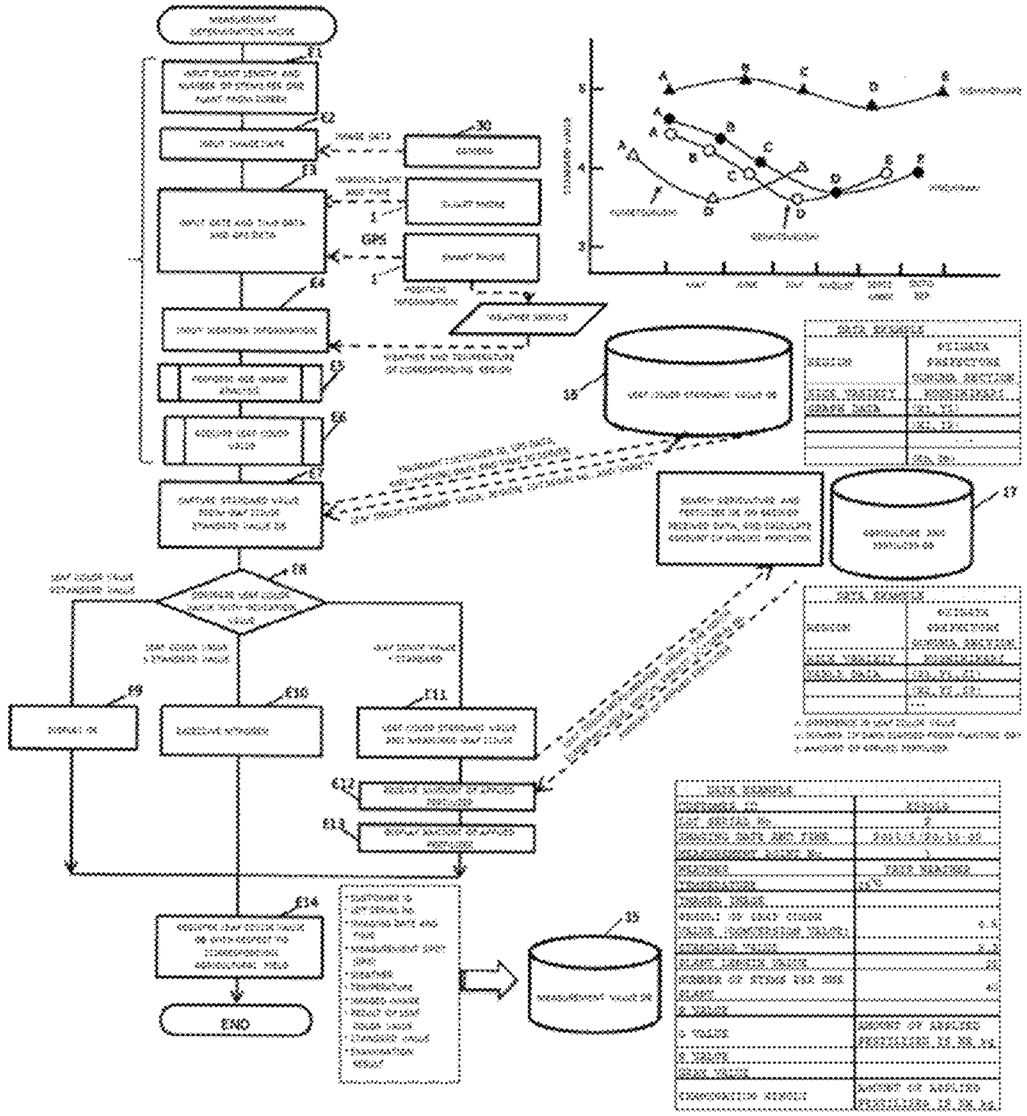

[Fig. 15]
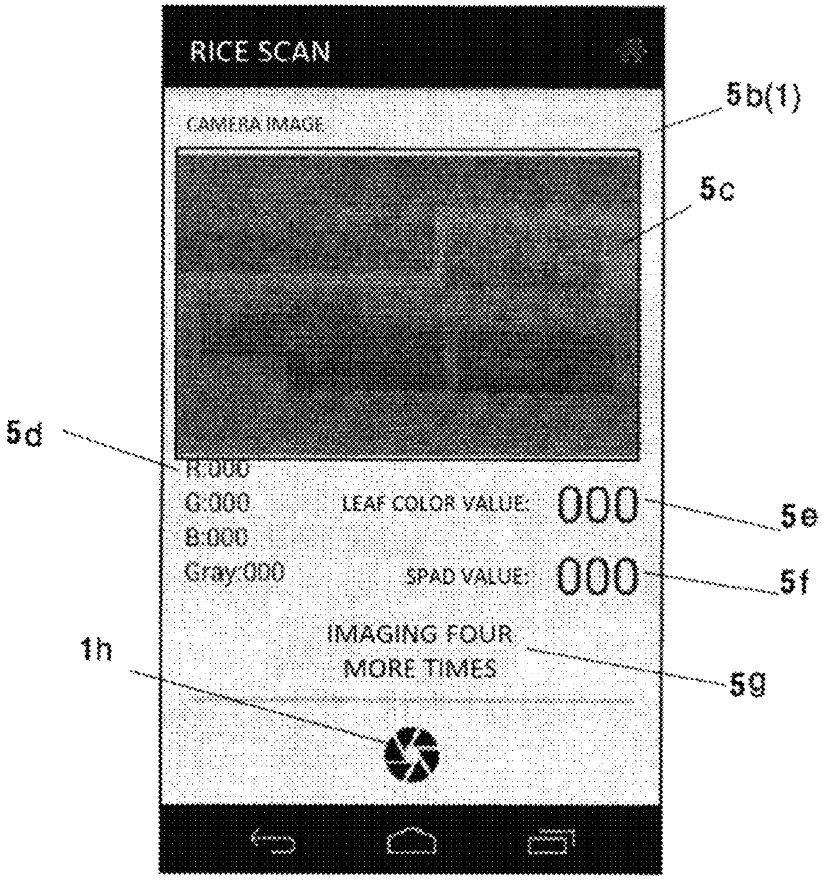

[Fig. 16]
1i(1)
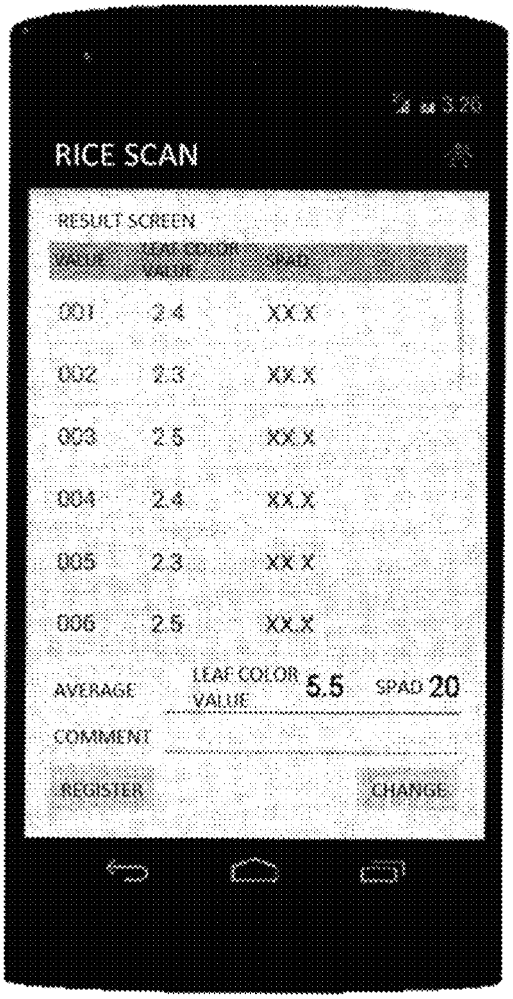

[Fig. 17]
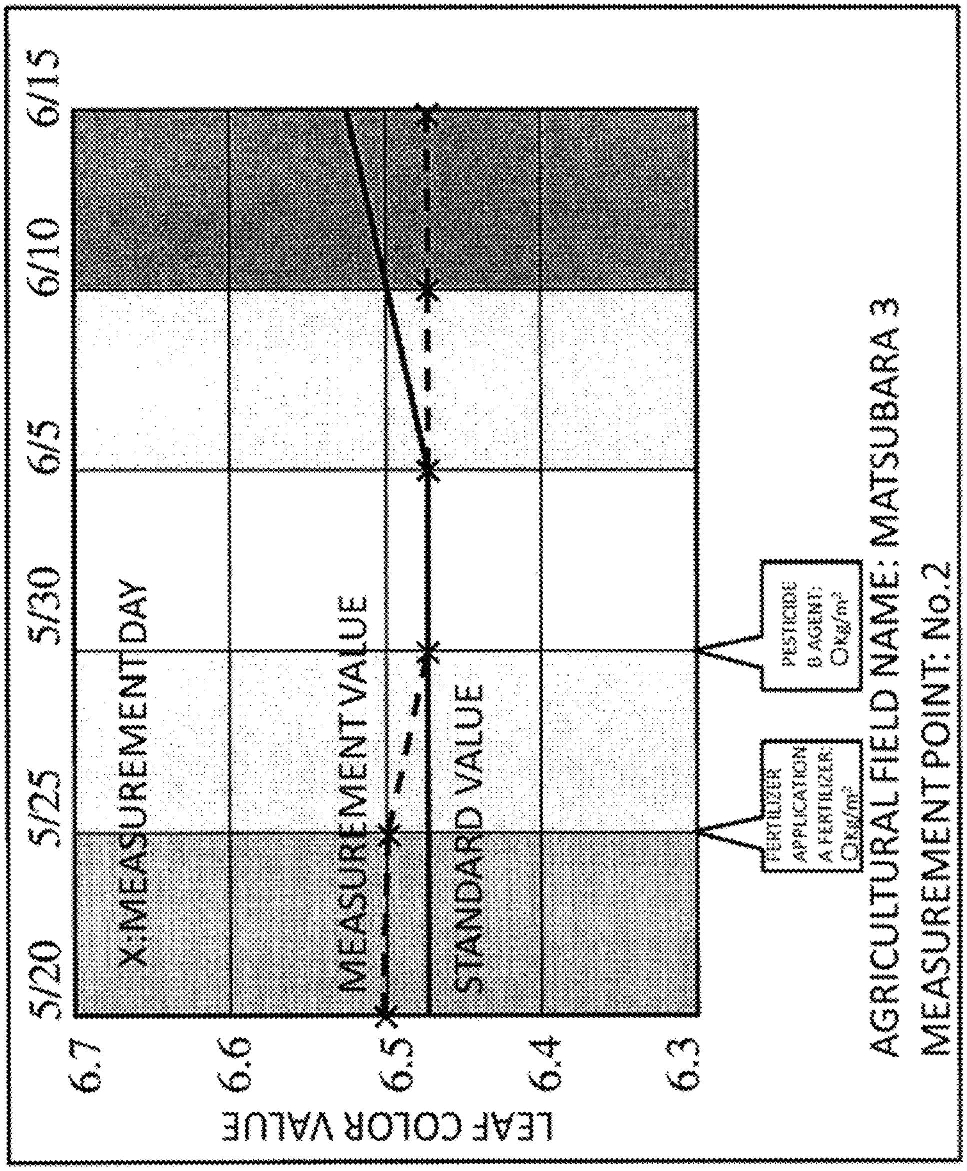

[Fig. 18]
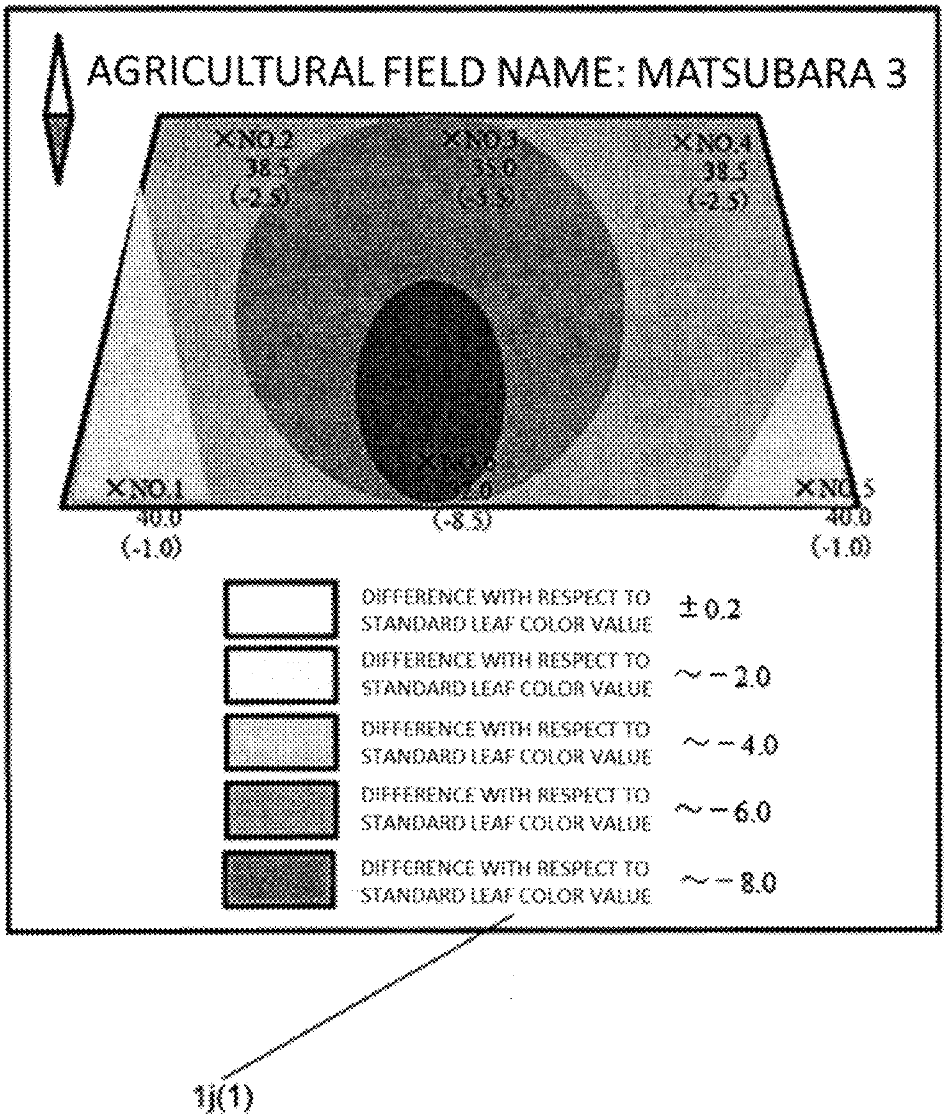

[Fig. 19]
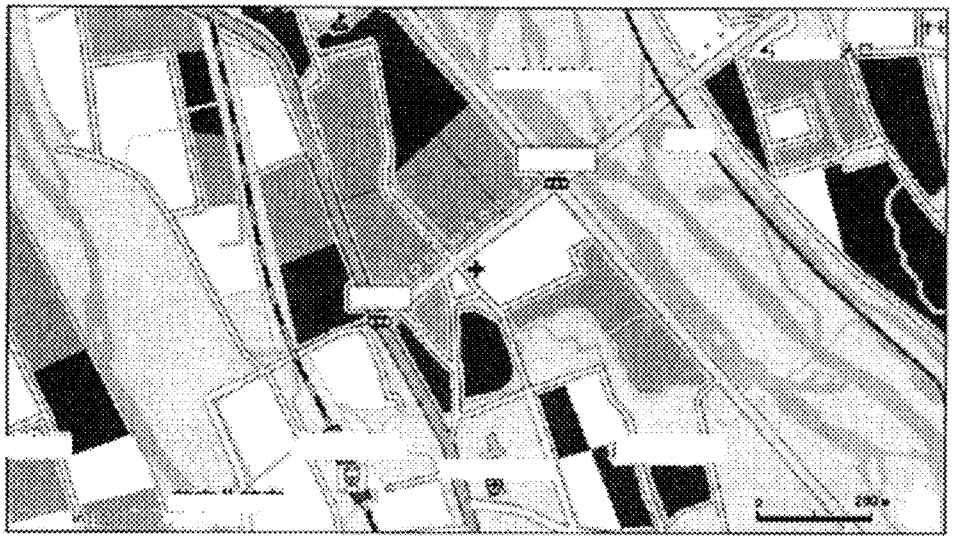
| | |
|---|---|
| DIFFERENCE WITH RESPECT TO STANDARD LEAF COLOR VALUE | ±0.2 |
| DIFFERENCE WITH RESPECT TO STANDARD LEAF COLOR VALUE | ~−0.4 |
| DIFFERENCE WITH RESPECT TO STANDARD LEAF COLOR VALUE | ~−0.6 |
| DIFFERENCE WITH RESPECT TO STANDARD LEAF COLOR VALUE | ~−0.8 |

[Fig. 20]

| IMAGE ANALYSIS METHOD | DATA PROCESSING METHOD | DATA PERIOD | TWO-LAMP DESKTOP | TWO-LAMP WINDOW WATERMARK | THREE-LAMP DESKTOP | THREE-LAMP WINDOW WATERMARK |
|---|---|---|---|---|---|---|
| RGB | EACH DATA | ENTIRE PERIOD (FOR FIVE DAYS) | ○ | ○ | ○ | ○ |
| RGB | TEN-POINT AVERAGE | ENTIRE PERIOD (FOR FIVE DAYS) | ○ | ○ | ○ | ○ |
| RGB | EACH DATA | THREE DAYS IN SECOND HALF | ○ | ○ | ○ | ○ |
| HSV | EACH DATA | ENTIRE PERIOD (FOR FIVE DAYS) | ○ | ○ | ○ | ○ |
| HSV | TEN-POINT AVERAGE | ENTIRE PERIOD (FOR FIVE DAYS) | ○ | ○ | ○ | ○ |

[Fig. 21]
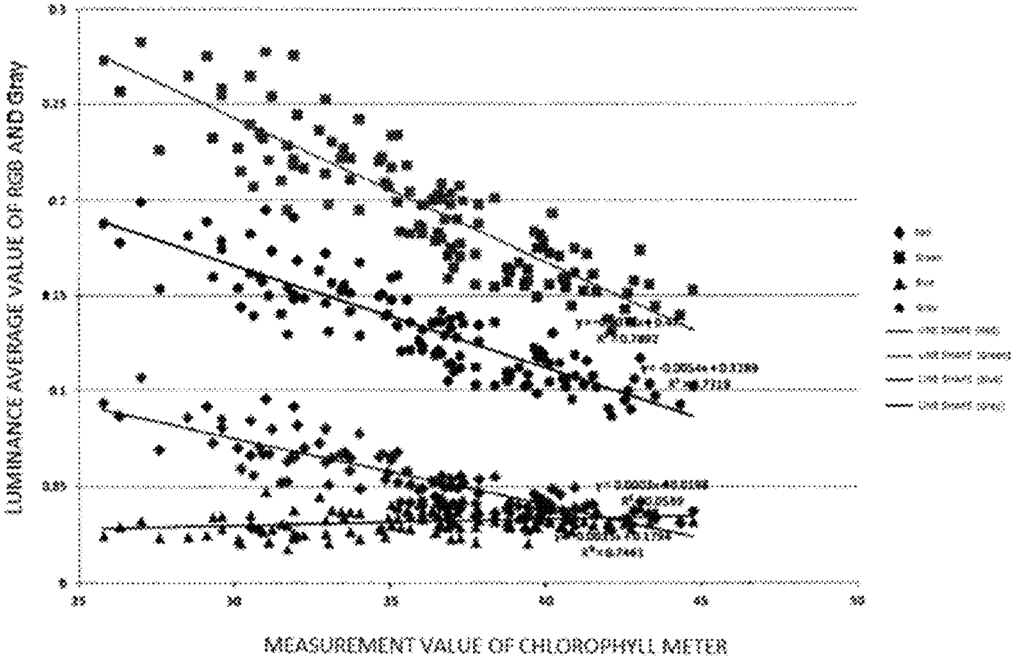

[Fig. 22]
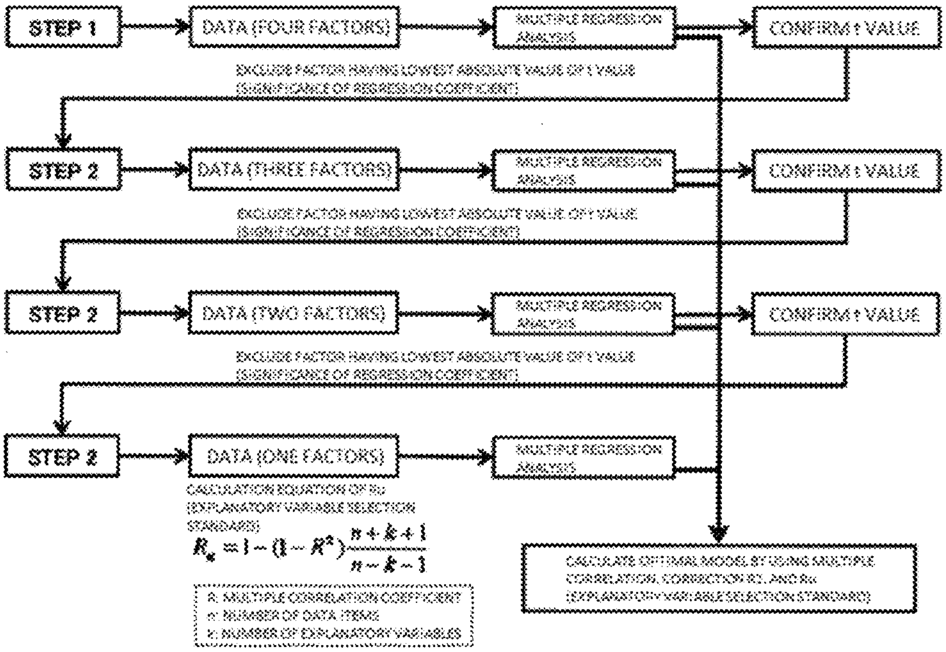

[Fig. 23]

CASE OF TEN-POINT AVERAGE DATA IN EACH MEASUREMENT CONDITION OF TWO-LAMP DESKTOP MEASUREMENT

| | | | | | AVERAGE | AVERAGE | AVERAGE | AVERAGE |
|---|---|---|---|---|---|---|---|---|
| MEASUREMENT DAY | TEST SECTION | IMAGING CONDITION | No. | SPAD VALUE | Green | Gray | Red | Blue |
| JUNE 25 | E-EAST-1 | TWO-LAMP DESKTOP | ave | 40.87 | 0.1743 | 0.1178 | 0.0455 | 0.036 |
| JUNE 25 | E-EAST-2 | TWO-LAMP DESKTOP | ave | 42.96 | 0.1582 | 0.1074 | 0.044 | 0.033 |
| JUNE 25 | E-EAST-3 | TWO-LAMP DESKTOP | ave | 44.47 | 0.1484 | 0.1003 | 0.0377 | 0.0344 |
| JUNE 25 | E-EAST-4 | TWO-LAMP DESKTOP | ave | 44.1 | 0.139 | 0.0926 | 0.0323 | 0.0308 |
| JUNE 25 | E-MIDDLE-1 | TWO-LAMP DESKTOP | ave | 43.13 | 0.1601 | 0.1068 | 0.0389 | 0.0294 |
| JUNE 25 | E-MIDDLE-2 | TWO-LAMP DESKTOP | ave | 45.74 | 0.15 | 0.1007 | 0.0373 | 0.0324 |
| JUNE 25 | E-MIDDLE-11 | TWO-LAMP DESKTOP | ave | 39.12 | 0.1647 | 0.1106 | 0.0417 | 0.0282 |
| JUNE 25 | E-MIDDLE-12 | TWO-LAMP DESKTOP | ave | 45.66 | 0.1433 | 0.0959 | 0.0336 | 0.0325 |
| JULY 4 | E-MIDDLE-1 | TWO-LAMP DESKTOP | ave | 36.33 | 0.20411 | 0.14192 | 0.06317 | 0.04661 |
| JULY 4 | E-MIDDLE-12 | TWO-LAMP DESKTOP | ave | 42.54 | 0.18348 | 0.12804 | 0.05228 | 0.05795 |
| JULY 4 | E-EAST-7 | TWO-LAMP DESKTOP | ave | 39.43 | 0.18829 | 0.131 | 0.05498 | 0.05262 |
| JULY 4 | E-EAST-8 | TWO-LAMP DESKTOP | ave | 36.5 | 0.19551 | 0.13629 | 0.05827 | 0.05365 |
| JULY 11 | E-EAST-4 | TWO-LAMP DESKTOP | ave | 37.22 | 0.21411 | 0.15285 | 0.06585 | 0.08066 |
| JULY 11 | E-EAST-8 | TWO-LAMP DESKTOP | ave | 30.16 | 0.26465 | 0.18984 | 0.09284 | 0.07575 |
| JULY 11 | E-MIDDLE-1 | TWO-LAMP DESKTOP | ave | 29.15 | 0.27184 | 0.19599 | 0.09899 | 0.07659 |
| JULY 11 | E-MIDDLE-2 | TWO-LAMP DESKTOP | ave | 39.57 | 0.19819 | 0.14239 | 0.06206 | 0.08173 |
| JULY 11 | E-MIDDLE-3 | TWO-LAMP DESKTOP | ave | 34.59 | 0.25044 | 0.17956 | 0.08275 | 0.08486 |
| JULY 11 | E-MIDDLE-13 | TWO-LAMP DESKTOP | ave | 42.05 | 0.19836 | 0.14171 | 0.05705 | 0.08748 |
| JULY 11 | 131-1 | TWO-LAMP DESKTOP | ave | 30.69 | 0.29386 | 0.21241 | 0.10818 | 0.08266 |
| JULY 11 | 131-3 | TWO-LAMP DESKTOP | ave | 40.78 | 0.20799 | 0.14874 | 0.06311 | 0.08347 |
| JULY 11 | 131-11 | TWO-LAMP DESKTOP | ave | 40.2 | 0.21435 | 0.15315 | 0.06381 | 0.08718 |
| JULY 11 | 131-13 | TWO-LAMP DESKTOP | ave | 45.96 | 0.18501 | 0.13286 | 0.05309 | 0.09046 |
| JULY 25 | E-EAST-1 | TWO-LAMP DESKTOP | ave | 34.35 | 0.22987 | 0.1576 | 0.06789 | 0.03898 |
| JULY 25 | E-EAST-2 | TWO-LAMP DESKTOP | ave | 37.2 | 0.18473 | 0.12387 | 0.04552 | 0.03531 |
| JULY 25 | E-EAST-3 | TWO-LAMP DESKTOP | ave | 38.04 | 0.17677 | 0.1178 | 0.04129 | 0.0339 |
| JULY 25 | E-EAST-4 | TWO-LAMP DESKTOP | ave | 37.94 | 0.18805 | 0.12661 | 0.04778 | 0.03616 |
| JULY 25 | E-MIDDLE-1 | TWO-LAMP DESKTOP | ave | 28.82 | 0.2648 | 0.18296 | 0.08848 | 0.03108 |
| JULY 25 | E-MIDDLE-2 | TWO-LAMP DESKTOP | ave | 37.13 | 0.18002 | 0.11972 | 0.04487 | 0.0275 |
| JULY 25 | E-MIDDLE-11 | TWO-LAMP DESKTOP | ave | 30.62 | 0.21738 | 0.14719 | 0.06398 | 0.02498 |
| JULY 25 | E-MIDDLE-12 | TWO-LAMP DESKTOP | ave | 42.26 | 0.14594 | 0.09704 | 0.03311 | 0.03127 |
| JULY 25 | 131-11 | TWO-LAMP DESKTOP | ave | 39.55 | 0.16381 | 0.10904 | 0.03975 | 0.02977 |
| JULY 25 | 131-13 | TWO-LAMP DESKTOP | ave | 40.8 | 0.15789 | 0.10569 | 0.0386 | 0.03277 |
| JULY 25 | 131-3 | TWO-LAMP DESKTOP | ave | 34.03 | 0.22214 | 0.15041 | 0.0632 | 0.03022 |
| JULY 25 | 131-5 | TWO-LAMP DESKTOP | ave | 33.7 | 0.22124 | 0.15804 | 0.0544 | 0.02849 |
| AUGUST 18 | E-EAST-1 | TWO-LAMP DESKTOP | ave | 33.08 | 0.1917 | 0.12736 | 0.04691 | 0.02782 |
| AUGUST 18 | E-EAST-2 | TWO-LAMP DESKTOP | ave | 38.57 | 0.15694 | 0.10357 | 0.03494 | 0.0286 |
| AUGUST 18 | E-EAST-4 | TWO-LAMP DESKTOP | ave | 40.27 | 0.15453 | 0.10315 | 0.03413 | 0.02982 |
| AUGUST 18 | E-MIDDLE-1 | TWO-LAMP DESKTOP | ave | 34.61 | 0.18629 | 0.12415 | 0.04697 | 0.02722 |
| AUGUST 18 | E-MIDDLE-2 | TWO-LAMP DESKTOP | ave | 36.61 | 0.16991 | 0.11371 | 0.04198 | 0.03226 |
| AUGUST 18 | E-MIDDLE-12 | TWO-LAMP DESKTOP | ave | 39.72 | 0.14449 | 0.0945 | 0.0296 | 0.02701 |
| AUGUST 18 | 131-1 | TWO-LAMP DESKTOP | ave | 27.82 | 0.25938 | 0.1789 | 0.08531 | 0.03089 |
| AUGUST 18 | 131-5 | TWO-LAMP DESKTOP | ave | 32.87 | 0.19811 | 0.12678 | 0.04959 | 0.02583 |
| AUGUST 18 | 131-11 | TWO-LAMP DESKTOP | ave | 34.1 | 0.17884 | 0.11779 | 0.04252 | 0.02326 |
| AUGUST 18 | 131-15 | TWO-LAMP DESKTOP | ave | 37.15 | 0.16457 | 0.1081 | 0.03775 | 0.0248 |

A

[Fig. 24]
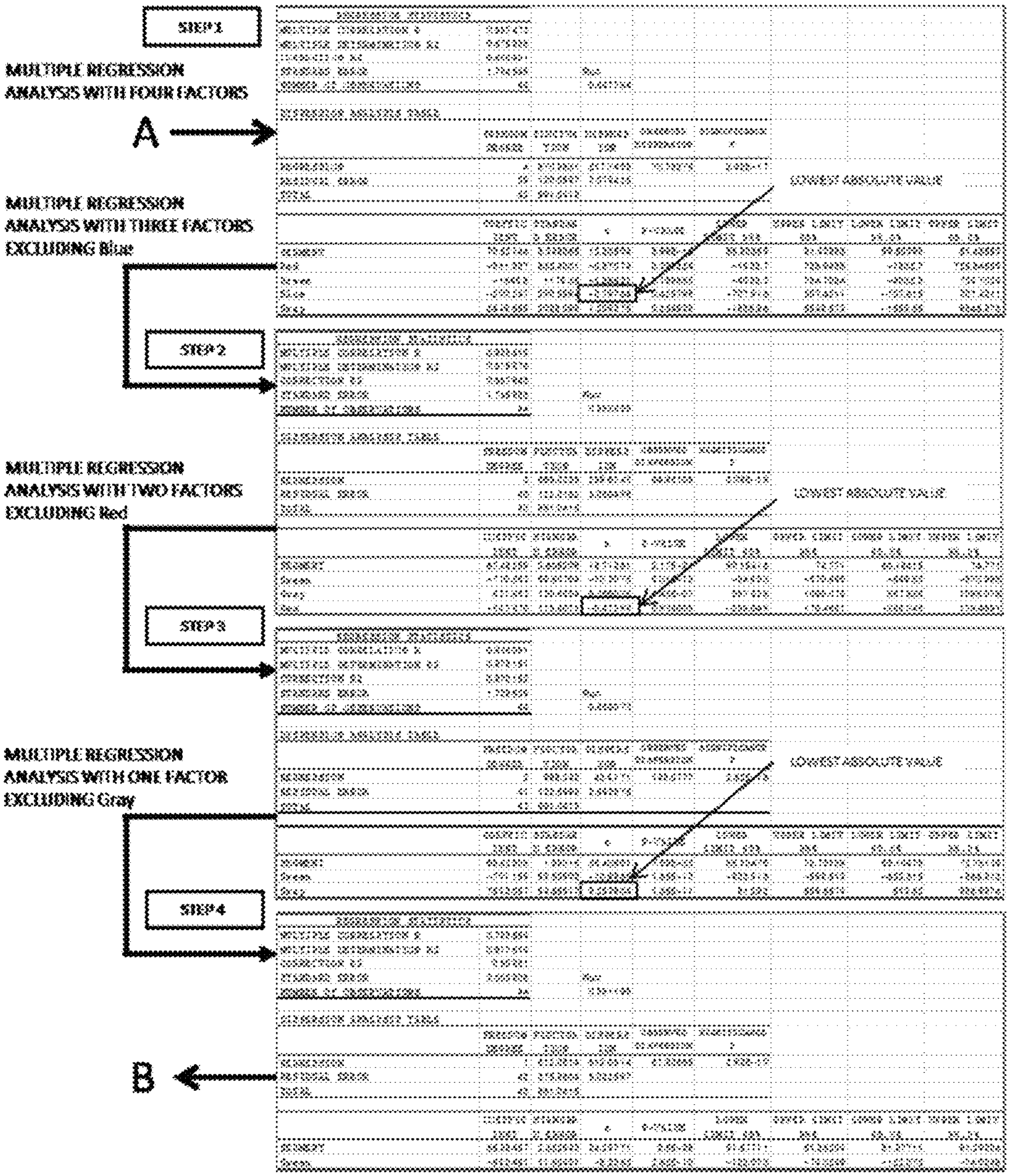

[Fig. 25]

EXPLANATORY VARIABLE

ACQUIRE MAXIMUM VALUE BY CORRECTION R2 AND Ru IN STEP 3 (TWO-FACTOR ANALYSIS)

| | Red | Green | Blue | Gray | R | CORRECTION R2 | Ru |
|---|---|---|---|---|---|---|---|
| 1 | ○ | ○ | ○ | ○ | 0.937473 | 0.866431 | 0.847794 |
| 2 | ○ | ○ | | ○ | 0.936418 | 0.867645 | 0.852255 |
| 3 | | ○ | | ○ | 0.936051 | 0.870152 | 0.858073 |
| 4 | | ○ | | | 0.785884 | 0.60851 | 0.581196 |

OPTIMIZATION CONDITION (row 3)

B (row 2)

[Fig. 26]

| IMAGE ANALYSIS METHOD | IMAGING CONDITION | DATA PROCESSING | DATA PERIOD | GRAPH HORIZONTAL AXIS NAME | MULTIPLE DETERMINATION | SIGNIFICANCE F |
|---|---|---|---|---|---|---|
| HSV | TWO-LAMP DESKTOP | TEN-POINT AVERAGE | ENTIRE PERIOD | HSV-TWO-LAMP DESKTOP (AVERAGE) | 0.888529 | 4.82E-18 |
| HSV | TWO-LAMP DESKTOP | EACH POINT | ENTIRE PERIOD | HSV-TWO-LAMP DESKTOP | 0.784104 | 2.7E-143 |
| RGB | TWO-LAMP DESKTOP | TEN-POINT AVERAGE | ENTIRE PERIOD | RGB-TWO-LAMP DESKTOP (AVERAGE) | 0.878191 | 2.52E-19 |
| RGB | TWO-LAMP DESKTOP | EACH POINT | ENTIRE PERIOD | RGB-TWO-LAMP DESKTOP | 0.774716 | 1.2E-140 |
| RGB | TWO-LAMP DESKTOP | EACH POINT | THREE DATA ITEMS IN SECOND HALF | RGB-TWO-LAMP DESKTOP-THREE DAYS IN SECOND HALF | 0.802627 | 5.8E-111 |
| HSV | TWO-LAMP WINDOW | TEN-POINT AVERAGE | ENTIRE PERIOD | HSV-TWO-LAMP WINDOW WATERMARK (AVERAGE) | 0.799962 | 4.87E-14 |
| HSV | TWO-LAMP WINDOW | EACH POINT | ENTIRE PERIOD | HSV-TWO-LAMP WINDOW WATERMARK | 0.616927 | 2.05E-89 |
| RGB | TWO-LAMP WINDOW | TEN-POINT AVERAGE | ENTIRE PERIOD | RGB-TWO-LAMP WINDOW WATERMARK (AVERAGE) | 0.722647 | 3.2E-11 |
| RGB | TWO-LAMP WINDOW | EACH POINT | ENTIRE PERIOD | RGB-TWO-LAMP WINDOW WATERMARK | 0.583921 | 1.68E-81 |
| RGB | TWO-LAMP WINDOW | EACH POINT | THREE DATA ITEMS IN SECOND HALF | RGB-TWO-LAMP WINDOW WATER MARK-THREE DAYS IN SECOND HALF | 0.599849 | 1.56E-62 |
| HSV | THREE-LAMP DESKTOP | TEN-POINT AVERAGE | ENTIRE PERIOD | HSV-THREE-LAMP DESKTOP (AVERAGE) | 0.849658 | 1.66E-16 |
| HSV | THREE-LAMP DESKTOP | EACH POINT | ENTIRE PERIOD | HSV-THREE-LAMP DESKTOP | 0.731605 | 4.2E-124 |
| RGB | THREE-LAMP DESKTOP | TEN-POINT AVERAGE | ENTIRE PERIOD | RGB-THREE-LAMP DESKTOP (AVERAGE) | 0.845954 | 2.22E-17 |
| RGB | THREE-LAMP DESKTOP | EACH POINT | ENTIRE PERIOD | RGB-THREE-LAMP DESKTOP | 0.726435 | 1.5E-119 |
| RGB | THREE-LAMP DESKTOP | EACH POINT | THREE DATA ITEMS IN SECOND HALF | RGB-THREE-LAMP DESKTOP-THREE DAYS IN SECOND HALF | 0.768985 | 3.6E-100 |
| HSV | THREE-LAMP WINDOW | TEN-POINT AVERAGE | ENTIRE PERIOD | HSV-THREE-LAMP WINDOW WATERMARK (AVERAGE) | 0.875502 | 4.1E-17 |
| HSV | THREE-LAMP WINDOW | EACH POINT | ENTIRE PERIOD | HSV-THREE-LAMP WINDOW WATERMARK | 0.688775 | 7.9E-109 |
| RGB | THREE-LAMP WINDOW | TEN-POINT AVERAGE | ENTIRE PERIOD | RGB-THREE-LAMP WINDOW WATERMARK (AVERAGE) | 0.844776 | 2.6E-17 |
| RGB | THREE-LAMP WINDOW | EACH POINT | ENTIRE PERIOD | RGB-THREE-LAMP WINDOW WATERMARK | 0.695708 | 1.2E-109 |
| RGB | THREE-LAMP WINDOW | EACH POINT | THREE DATA ITEMS IN SECOND HALF | RGB-THREE-LAMP WINDOW WATER MARK-THREE DAYS IN SECOND HALF | 0.738397 | 2.23E-90 |

[Fig. 27]
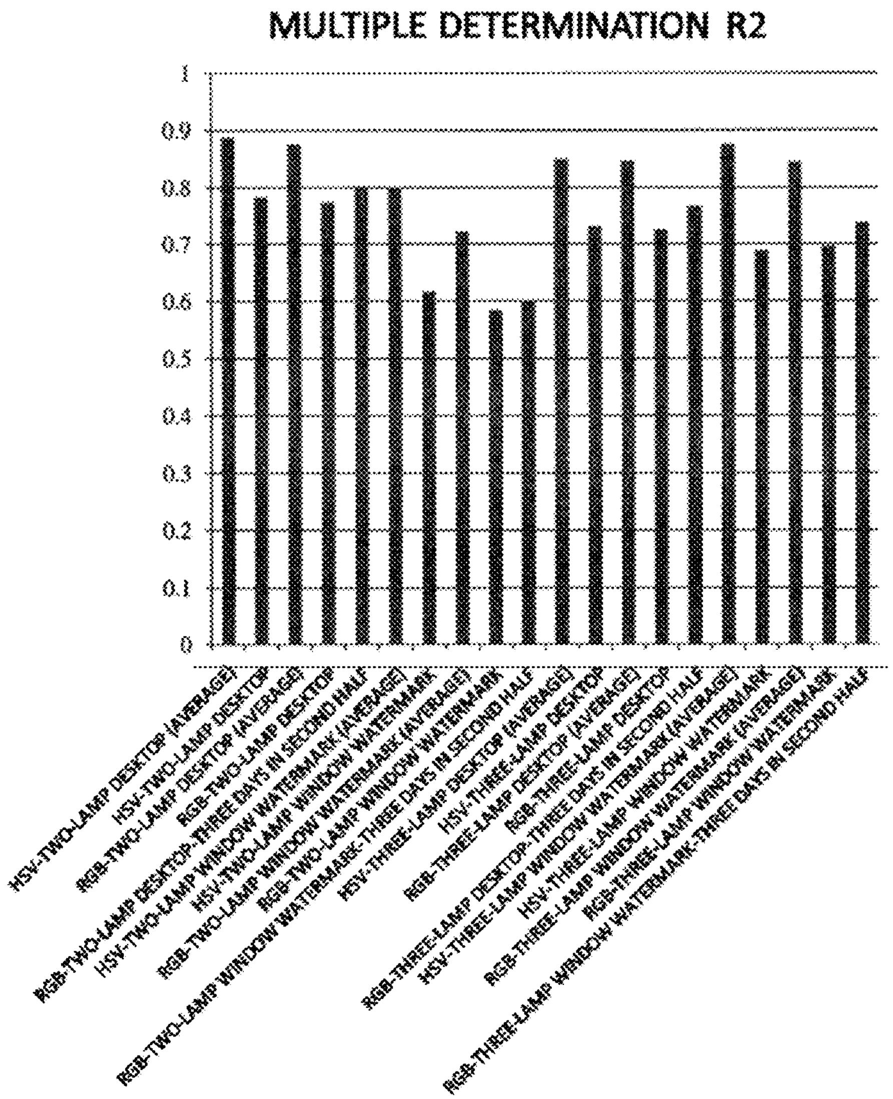

[Fig. 28]
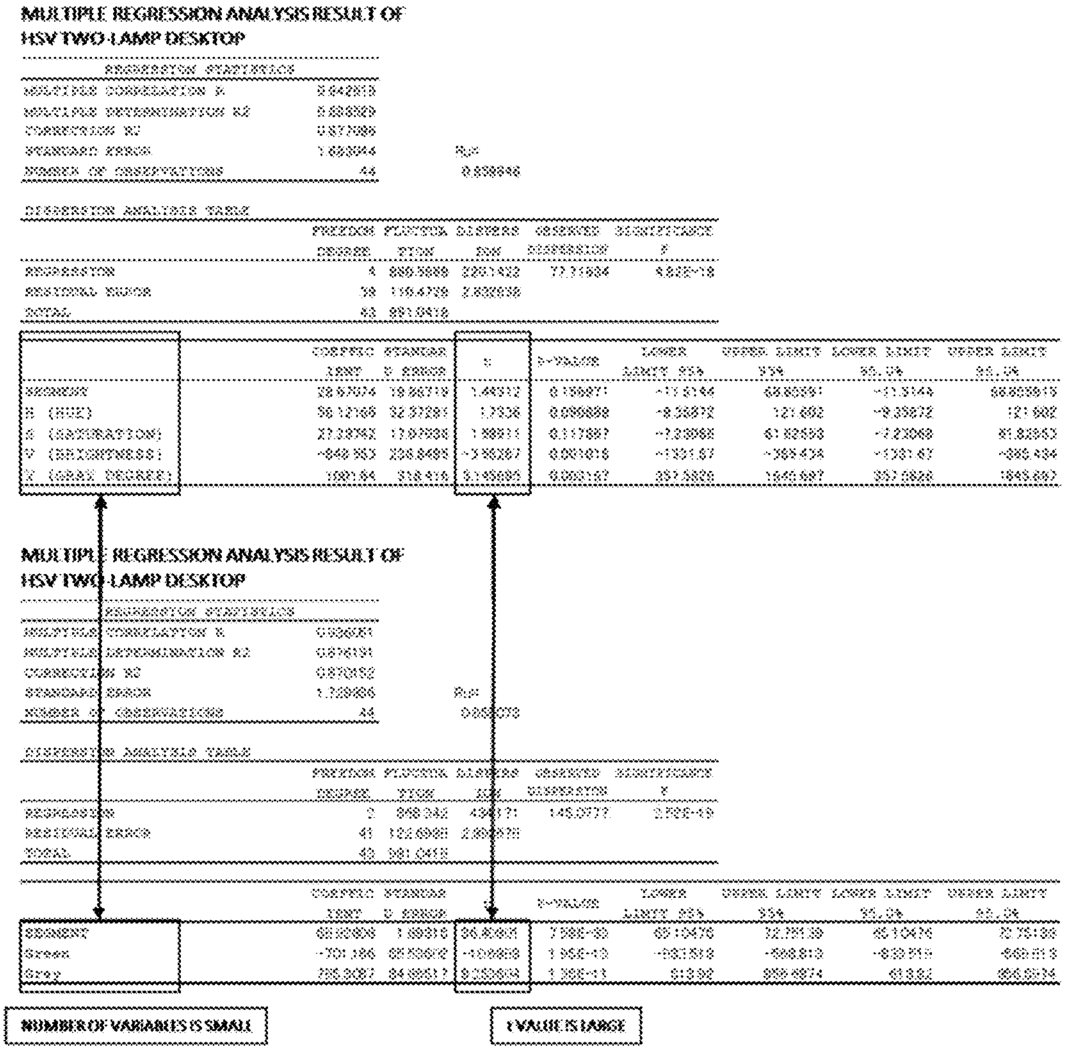

[Fig. 29]
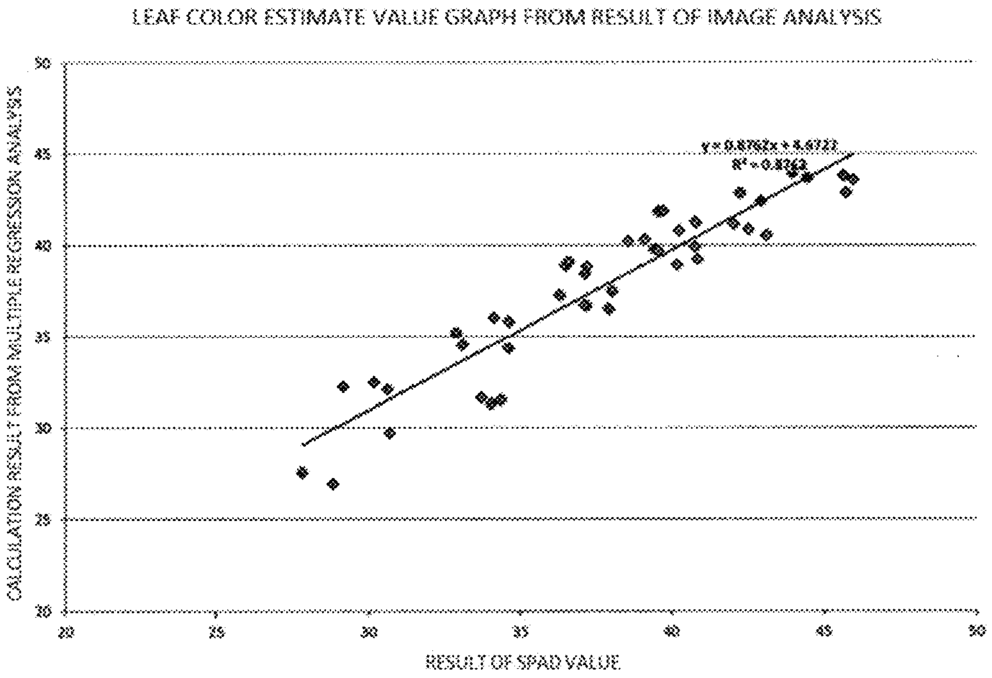

[Fig. 30]
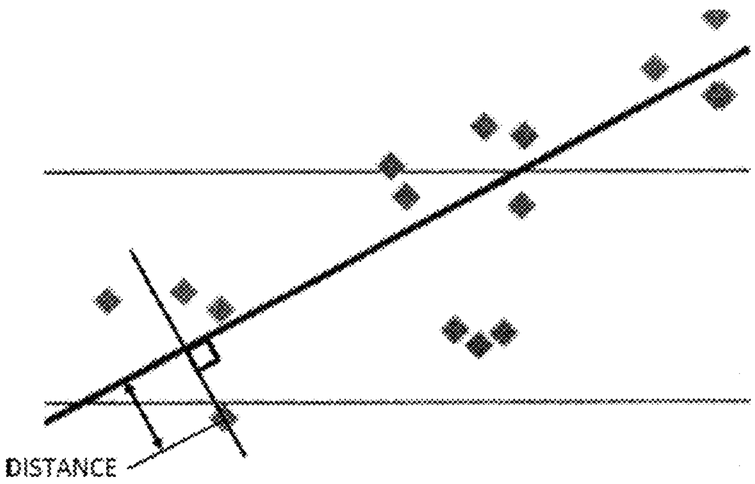
[Fig. 31]
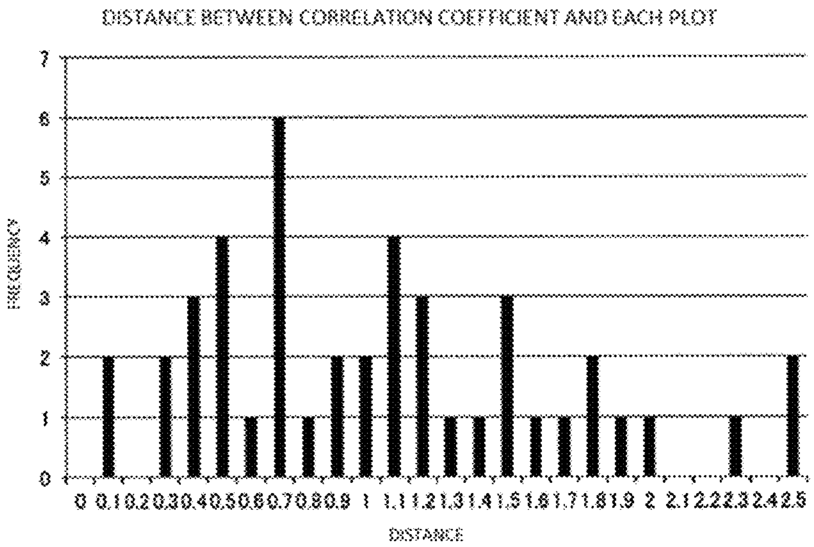

[Fig. 32]

<table>
<tr><th>PHENOMENON</th><th>IMAGE (EXAMPLE)</th></tr>
<tr><td>DEFECTIVE LEAF POSITION<br>(LEAF END EXTENDS OVER CAMERA IMAGING AREA)</td><td>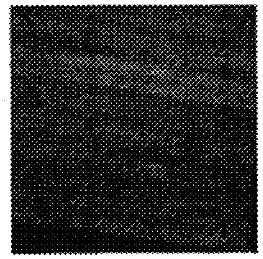
<table>
<tr><th></th><th>1.</th><th>2.</th><th>3.</th><th>4.</th></tr>
<tr><td>R LUMINANCE VALUE</td><td>104</td><td>128</td><td>98</td><td>85</td></tr>
<tr><td>G LUMINANCE VALUE</td><td>114</td><td>122</td><td>100</td><td>58</td></tr>
<tr><td>B LUMINANCE VALUE</td><td>62</td><td>70</td><td>80</td><td>59</td></tr>
<tr><td>Y VALUE</td><td>0.425</td><td>0.470</td><td>0.381</td><td>0.229</td></tr>
<tr><td>LEAF COLOR CONVERSION VALUE</td><td>5.27</td><td>4.76</td><td>6.43</td><td>8.22</td></tr>
</table></td></tr>
<tr><td>OUTSIDE LIGHT<br>(PART BECOMES PALE DUE TO ABNORMAL PRESSING)</td><td>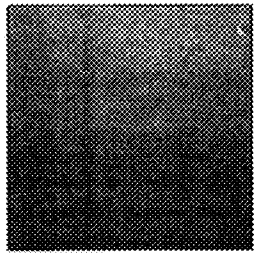
<table>
<tr><th></th><th>RESULT</th><th>AVERAGE</th></tr>
<tr><td>LEAF COLOR VALUE</td><td>4.7</td><td>5.08</td></tr>
<tr><td>R LUMINANCE VALUE</td><td>137</td><td>139.4</td></tr>
<tr><td>G LUMINANCE VALUE</td><td>138</td><td>128.9</td></tr>
<tr><td>B LUMINANCE VALUE</td><td>78</td><td>53.7</td></tr>
<tr><td>GRAY VALUE</td><td>128.7</td><td>137.4</td></tr>
</table></td></tr>
<tr><td>ONLY ONE PICTURE IS DENSE OR PALE</td><td></td></tr>
</table>

[Fig. 33]
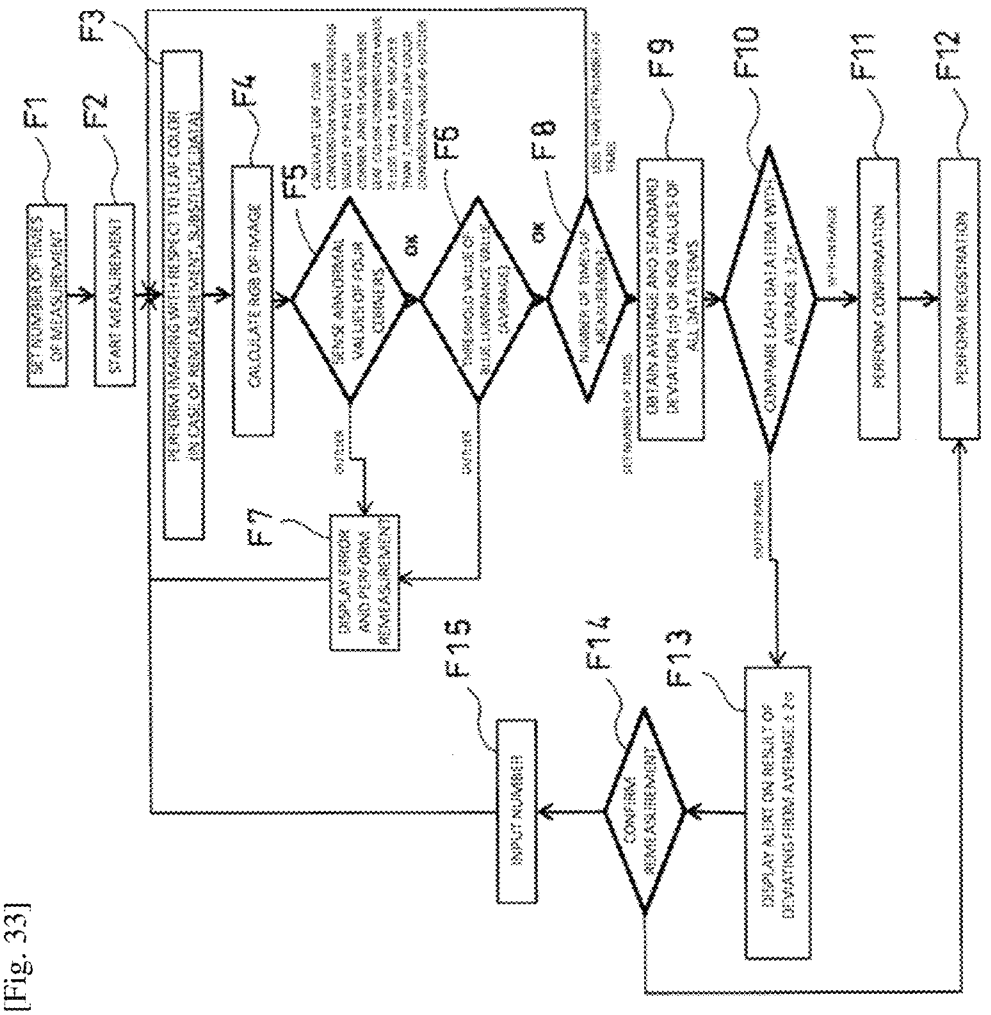

[Fig. 34]
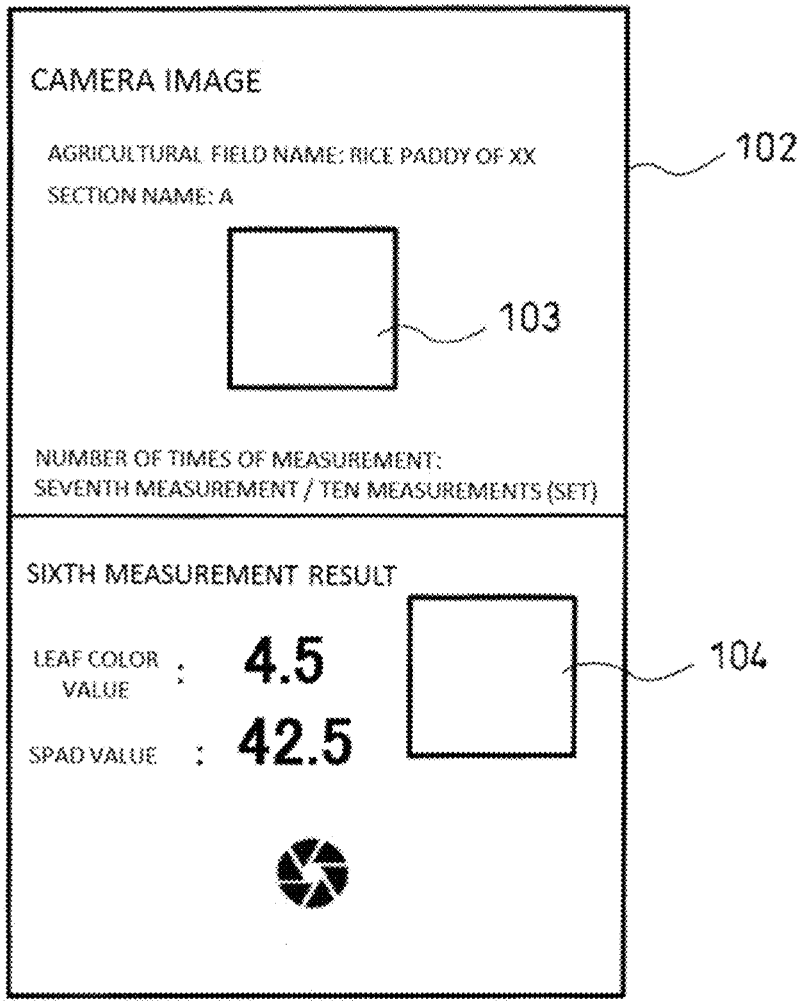

[Fig. 35]
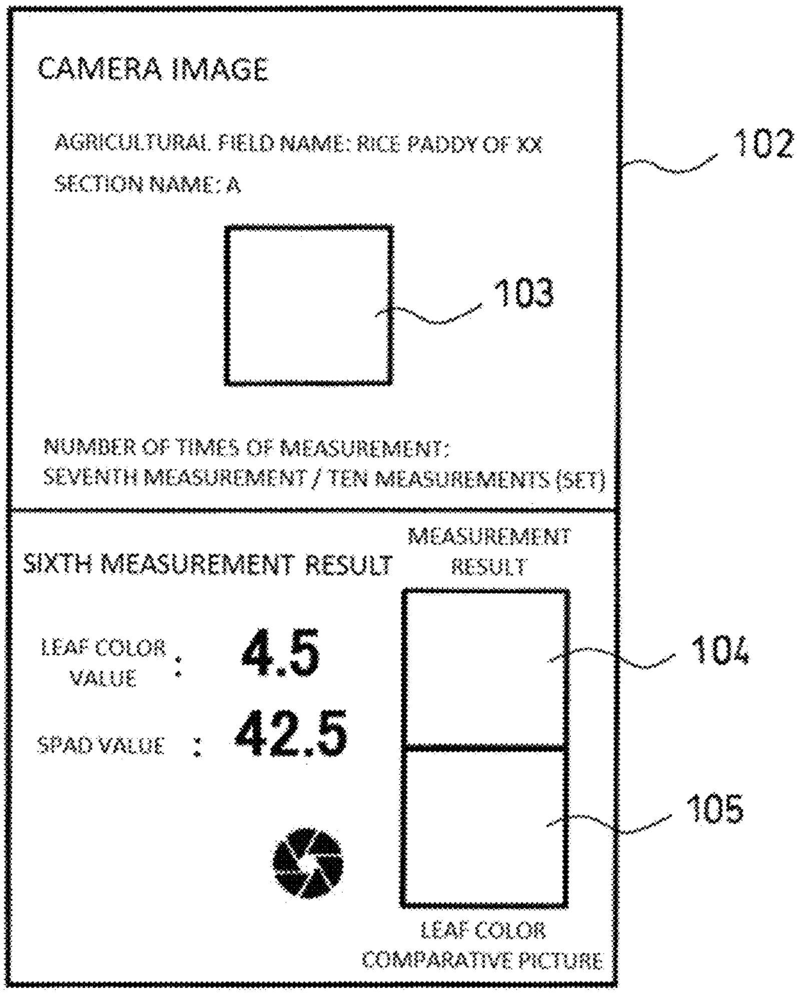

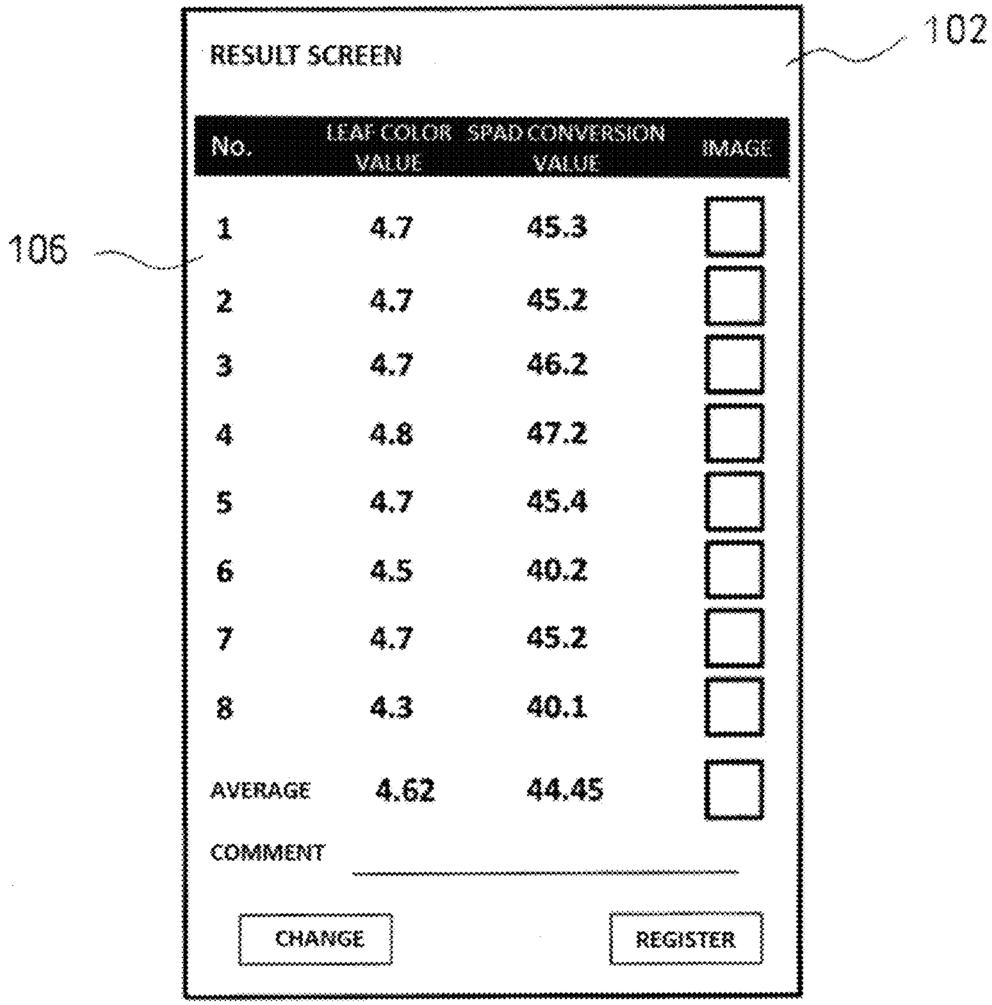
[Fig. 36]
| No. | LEAF COLOR VALUE | SPAD CONVERSION VALUE | IMAGE |
|---|---|---|---|
| 1 | 4.7 | 45.3 | ☐ |
| 2 | 4.7 | 45.2 | ☐ |
| 3 | 4.7 | 46.2 | ☐ |
| 4 | 4.8 | 47.2 | ☐ |
| 5 | 4.7 | 45.4 | ☐ |
| 6 | 4.5 | 40.2 | ☐ |
| 7 | 4.7 | 45.2 | ☐ |
| 8 | 4.3 | 40.1 | ☐ |
| AVERAGE | 4.62 | 44.45 | ☐ |
RESULT SCREEN — 102
106
COMMENT
CHANGE    REGISTER

[Fig. 37]
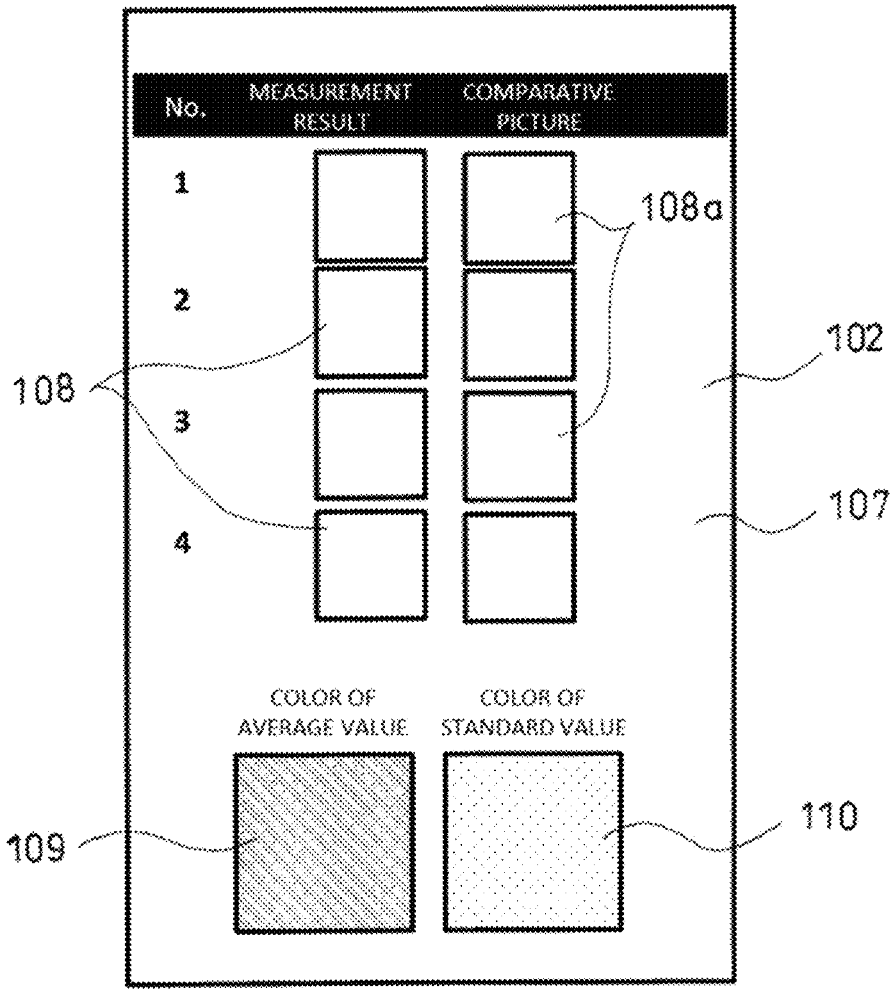

[Fig. 38]
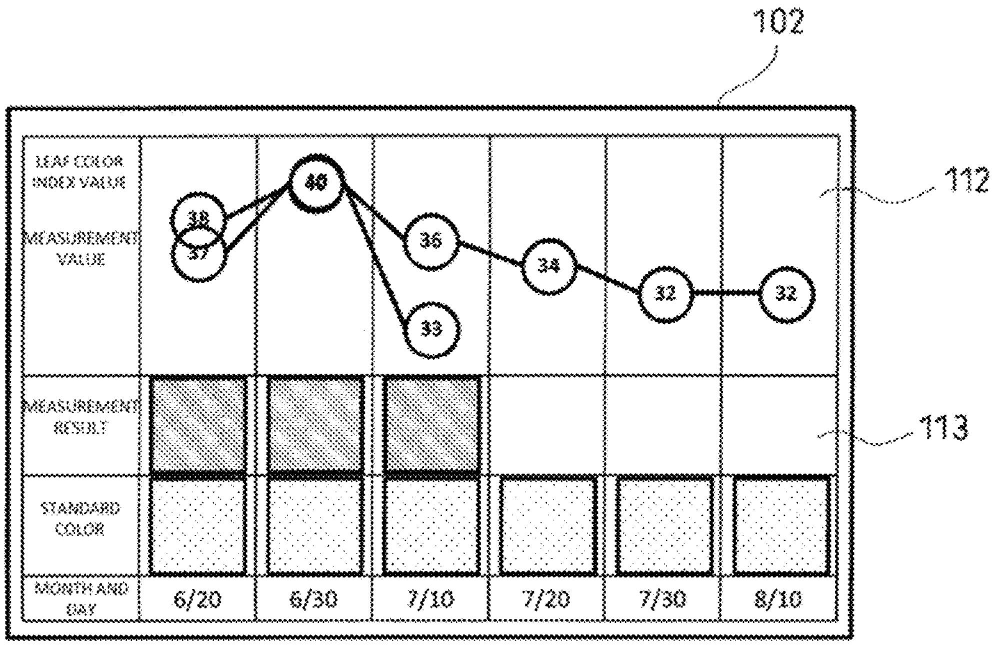

PLANT INFORMATION ACQUISITION SYSTEM, PLANT INFORMATION ACQUISITION DEVICE, PLANT INFORMATION ACQUISITION METHOD, CROP MANAGEMENT SYSTEM AND CROP MANAGEMENT METHOD

TECHNICAL FIELD

The present invention relates to a plant information acquisition system, a plant information acquisition device, a plant information acquisition method, a crop management system, and a crop management method for acquiring information of a plant from the color of the surface of the plant, and for managing and supporting various agricultural works or the like relevant to the production of a product such as a crop according to the cultivation of a useful plant.

BACKGROUND ART

In the agriculture, in particular, the cultivation of a rice plant, there is a case of using a leaf color scale, that is, a color chart of a leaf color density which becomes an index of fertilizer application management of wet-rice. In the leaf color scale, leaf colors from 1, which is the palest, to 7, which is the densest, are gradually illustrated, and in the case of reading to the intermediate value of each value, the leaf color can be measured in thirteen stages, and thus, it is possible to easily determine the leaf color. Here, in the measurement, attention such as placing the sun on the back is required, and thus, it is difficult to determine the leaf color according to a measurement time zone. In addition, in a crop such as a rice plant, it is known that in a case where a nitrogen content of the crop increases, a green color becomes dense (a chlorophyll content increases), and for example, the leaf color scale can be a material of determining a period or an amount in fertilizer application such that it is preferable to apply a nitrogen-based fertilizer in a case where a green color of a leaf of a rice plant having a predetermined variety in a predetermined period in a predetermined region is paler than a predetermined density.

The fertilizer application management is performed according to a document in which, for example, a timing or the like for applying the fertilizer is described from the color of the leaf of the rice plant. The document is required to be prepared in each of regions where environments such as climate or soil are similar to each other to a certain degree, and for example, is prepared such that the fertilizer application management or the like can be performed from a date (a period) such as a month and a day, and mainly the color on the leaf color scale at the date. As described above, the document which is used, for example, in the fertilizer application management according to the leaf color scale is required to be prepared in a comparatively narrow range such as a prefecture or a municipal unit, and for example, is prepared by a public institution (a prefectural agricultural experiment station) associated with the agriculture or other organizations (an agricultural cooperative, an agricultural corporation, or the like).

In addition, a chlorophyll meter is used in order to digitize the leaf color, in addition to the leaf color scale described above.

The chlorophyll meter obtains the content of the chlorophyll on the basis of the optical properties of the chlorophyll. It is known that the chlorophyll has an absorbance peak in a range of red of visible light of 600 nm to 700 nm, and rarely absorbs infrared light on a wavelength side longer than 700 nm. Therefore, a chlorophyll amount contained in the leaf, which is measured on the basis of a difference between an optical density of transmission light of the range of red and an optical density of transmission light of infrared light by using an LED outputting light in the range of red and an LED outputting infrared light, is calculated.

As with the measurement result of the leaf color scale described above, the measurement result of the chlorophyll meter, far example, can also be used for determining whether or not the amount of applied fertilizer of the nitrogen fertilizer is suitable, and the measurement result can be used as an index of the fertilizer application management. Furthermore, in the chlorophyll meter, a soil & plant analyzer development (SPAD) value, which becomes an index of the content of the chlorophyll, is output, the SPAD value is associated with a color scale value as the measurement result of the leaf color scale, and thus, the SPAD value and the color scale value can be converted into each other. Accordingly, in both of the SPAD value and the color scale value, it is possible to perform the fertilizer application management by using the document described above relevant to the cultivation of the same rice plant. In the following description, the SPAD value of the chlorophyll meter and the color scale value of the leaf color scale will be referred to as a leaf color value. That is, in the following description, the leaf color value includes the SPAD value and the color scale value.

The object of the chlorophyll meter described above is to measure the content of the chlorophyll and to measure a nitrogen amount of the crop on the basis of the content of the chlorophyll, and a spectroscopic analyzer is also proposed in which nitrogen is measured by optical measurement of the crop (for example, refer to Patent Literature 1). In this case, it is possible to directly measure the nitrogen content and thus, it is possible to use the spectroscopic analyzer in the fertilizer application management.

CITATION LIST

Patent Literature

Patent Literature 1: JP 8-327538 A

SUMMARY OF INVENTION

Technical Problem

Here, the leaf color scale has an advantage of a comparatively low price, but as described above, there is a variation in the measurement result according to a measurement time, weather, a measurer, or the like. In addition, the price of the chlorophyll meter or the spectroscopic analyzer is set to be commensurate with the cost, and thus, there is a possibility that a small-scale farming family may not purchase the chlorophyll meter or the spectroscopic analyzer. Furthermore, remote sensing using an artificial satellite is known as a method of measuring a growth state of a plant in a comparatively wide range, but a high cost is required for single measurement.

In addition, in order to use the measurement results of various devices, as described above, the document is required in which the fertilizer application management based on the measurement result is described corresponding to a region to be used. In a case of the leaf color scale, the measurement result is determined by the measurer, and the measurement result is not digital data, and thus, for example, it is unavoidable to obtain the fertilizer application management corresponding to the measurement result from the document, and for example, in the chlorophyll meter or the spectroscopic analyzer, a possibility that the measurement result is obtained as the digital data, is high, but basically, only the measurement result is output, and it is not possible to directly obtain data for the fertilizer application management from the measurement result.

In order to perform the fertilizer application management or the like according to the leaf color value described above, it is necessary that an agriculture worker cultivating a rice plant obtains a leaf color value in which, for example, a contrasting density or the like of the color of a leaf is digitized, by using the color scale or the chlorophyll meter described above, and calculates a specific amount of applied fertilizer, for example, from a document such as a brochure of a fertilizer application management method suitable for a region, which is provided by an autonomous community, an agricultural cooperative, or the like in each province, by using the leaf color value.

In the fertilizer application management of the rice plant, for example, in order to determine a fertilizer amount which is actually applied, information of the area of an agricultural field (a rice-field), the amount of rice plant such as the number of rice plants per unit area, and a growth rate such as the height of a rice stalk (slow growth, overgrowth, or the like) is required in addition to the leaf color value, and as described above, the document of the fertilizer application management provided by the autonomous community, the agricultural cooperative, or the like is required. In addition, knowledge or ability to actually determine the fertilizer amount on the basis of the document of the fertilizer application management is required for the agriculture worker.

By such fertilizer application management, it is possible to increase a production amount of the rice, to attain stabilization, or to improve quality, but the agriculture worker is required not only to perform the measurement of the leaf color value but also to have knowledge and ability for using the leaf color value described above, and for example, there is a case where it is difficult for an agriculture worker who is inexperienced and does not have sufficient knowledge about fertilizer application or the like, to perform the fertilizer application management based on the leaf color value described above. On the other hand, an agriculture worker who is skillful and has abundant knowledge about the fertilizer application management or fertilization management is able to perform the fertilizer application management or the fertilization management from the experience and the knowledge, but there is a possibility that the agriculture worker regards an operation such as the measurement of the leaf color as described above and the consideration of the fertilizer application from the measurement result and the distributed document, as a bother.

In addition, the growth of the crop greatly depends on the weather and thus in a case where various documents described above are prepared on the basis of the average weather of a plurality of years and the actual weather is greatly different from the average weather, the contents of the fertilizer application management or the fertilization management are required to be changed, and in a case where the contents of the document described above for the fertilizer application management or the fertilization management are changed, the change in the contents of the document is required to be transmitted to the agriculture worker performing agricultural works on the basis of the document.

The present invention has been made in consideration of the circumstances described above, and an object of the present invention is to provide a plant information acquisition system, a plant information acquisition device, a plant information acquisition method, a crop management system, and a crop management method, in which information of a plant based on the color of the surface of the plant can be acquired from image data obtained by imaging the plant, and thus, it is possible to acquire the information of the plant at a low cost, compared to a chlorophyll meter or a spectroscopic analyzer, and in the production of a crop such as a rice plant, fertilization management including fertilizer application management such as determination of a fertilizer amount, or other agricultural works, is supported through a smart phone or the like as a user terminal, on the basis of data to be observed, such as converted leaf color value which is calculated from image data obtained by imaging the crop.

Solution to Problem

To solve the problem, a plant information acquisition system of the present invention includes:

an imaging element;

an optical system including a lens focusing an image of a plant as an object on the imaging element;

an illumination light source configured to illuminate the plant at the time of performing imaging by using the imaging element; and a light shielding device configured to shield outside light at the time of performing imagine by using the imaging element, wherein information representing a chlorophyll amount of the plant is output from a correlative relationship between color information of a color of the plant which is obtained from an image signal output from the imaging element imaging the plant and the information representing the chlorophyll amount of the plant.

Furthermore, a plant information acquisition system of the present invention includes:

an imaging element;

an optical system including a lens focusing an image of a plant as an object on the imaging element;

an illumination light source configured to illuminate the plant at the time of performing imaging by using the imaging element;

a light shielding device configured to shield outside light at the time of performing imaging by using the imaging element;

an image processing device configured to acquire color information representing a color of the plant on the basis of an image signal output from the imaging element; and a plant information acquisition device configured to acquire plant information from the color information on the basis of a correlative relationship between the color information and the plant information relevant to the plant which is correlated with the color information.

Furthermore, a plant information acquisition method of the present invention is a plant information acquisition method using a plant information acquisition device including an imaging element, an optical system including a lens focusing an image of a plant as an object on the imaging element, an illumination light source configured to illuminate the plant at the time of performing imaging by using the imaging element, a light shielding device configured to shield outside light at the time of performing imaging by using the imaging element, and an image processing device configured to acquire color information representing a color of the plant on the basis of an image signal output from the imaging element, the method including:

acquiring plant information from the color information on the basis of a correlative relationship between the color information and the plant information relevant to the plant which is correlated with the color information.

According to such a configuration, for example, it is possible to obtain the plant information such as the content of chlorophyll or the content of nitrogen in the plant by imaging the plant with a so-called camera provided with the imaging element, the optical system including the lens, and the illumination light source. That is, even in the case of not using an expensive measurement device such as a calorimetric analyzer, it is possible to obtain the plant information such as a chlorophyll density by the camera which can be prepared at a low price.

In addition, in a state where the outside light is shielded by the light shielding device, the plant is imaged by light of the illumination light source, and thus, it is possible to image the plant with stable light intensity or in a stable light direction without being affected by outside light. Therefore, in the measurement in an outdoor rice-field or the like, it is possible to prevent the measurement result from being changed according to the position of the sun or the like. Furthermore, the plant information, for example, may include information of the content of components (compounds and molecules) contained in the plant, such as chlorophyll, nitrogen, a sugar content, or polyphenol, information of a growth degree of the plant or a mature degree of fruits of the plant, and information of whether or not diseases are developed.

In the plant information acquisition system and the plant information acquisition method of the present invention, it is preferable that the plant information is a numerical value which becomes an index of a content of a predetermined component contained in the plant, and the color information representing the color of the plant is represented by values of one or more types of variables among values of a plurality of types of variables configuring a color space of each pixel of image data obtained by performing imaging by the imaging element and is a representative value representing values of the variables respectively corresponding to a plurality of pixels in a predetermined range of the image data.

According to such a configuration, the color information is represented by the value of at least one type of variable of the variables configuring the color space, for example, each variable of R, G, and B of an RGB color space, each variable of H, S, and V of an HSV color space, or a variable of the color space obtained by adding a variable of gray (Gray, luminance) to the variables described above, and is the representative value (for example, an average value) of the variables of the plurality of pixels in the predetermined range of the image data which is obtained by performing imaging by the imaging element. In addition, the plant information is set to the value of the content of the component which is contained in the plant. Therefore, in a case where there is a correlative relationship between the value of the color information and the value of the plant information, it is possible to calculate the value of the plant information from the value of the color information by using a correlation equation, or to calculate the value of the plant information from the value of the color information by using a data table in which the value of the color information is associated with the value of the plant information on the basis of the correlative relationship. Furthermore, as described above, the growth degree of the plant, the mature degree of the fruits, or the presence or absence of the development of diseases may be obtained from the representative value described above of one or more variables of the variables of the color space as the color information.

Furthermore, in the plant information acquisition system of the present invention, it is preferable that regression analysis or multiple regression analysis is performed by setting the numerical value which becomes the index of the content of the predetermined component contained in the plant to a dependent variable and the representative value of the variable configuring the color space as the color information representing the color of the plant to an independent variable, and thus, a correlation equation for calculating the dependent variable from the independent variable is obtained, and the plant information acquisition device calculates the numerical value which becomes the index of the content of the predetermined component contained in the plant from the representative value as the color information on the basis of the image signal output from the imaging element by using the correlation equation.

Furthermore, in the plant information acquisition method of the present invention, it is preferable that regression analysis or multiple regression analysis is performed by setting the numerical value which becomes the index of the content of the predetermined component contained in the plant to a dependent variable and the representative value of the variable configuring the color space as the color information representing be color of the plant to an independent variable, and thus, a correlation equation for calculating the dependent variable from the independent variable is obtained, and the numerical value which becomes the index of the content of the predetermined component contained in the plant is calculated from the representative value as the color information on the basis of the image signal output from the imaging element by using the correlation equation.

According to such a configuration, a value, which becomes the plant information, is set to the dependent variable (an objective variable), a value, which becomes the color information, is set to the independent variable (an explanatory variable) and the correlation equation is obtained by the regression analysis or the multiple regression analysis, and thus, it is possible to calculate the value, which becomes the plant information, from the value, which becomes the color information, by the correlation equation. Therefore, in a case where there is the value of the plant information in which the correlative relationship with respect to the value of the color information is confirmed, it is possible to obtain a value which becomes the index representing the content of the component contained in the plant from the color information. Furthermore, the value, which becomes the index of the content, may represent the content as it is.

Furthermore, in the configuration of the present invention, it is preferable that the plant information is a leaf color value which becomes the index of the content of chlorophyll as the predetermined component, and the color space includes red (R) green (G), blue (B), and gray (Gray) or hue (H), saturation (S), brightness (V), and gray (Gray), as the type of the variable.

According to such a configuration, it is possible to measure a leaf color value having compatibility with an SPAD value at a low cost, compared to a chlorophyll meter in which a dedicated colorimetric analyzing device used in the measurement of the leaf color value (for example, a conversion value of an SPAD value) of the related art is mounted. Accordingly, it is possible to perform the fertilizer application management of the rice plant using the leaf color value (the conversion value of the SPAD value) with comparatively less burden, and to promote the introduction of fertilizer application management of a rice plant using a leaf color value in a small-scale farming family.

In addition, it is possible to suppress a variation in measurement data according to a measurement period or a measurement time, a measurement spot a measurer, or the like without being affected by the outside light in the measurement as with the leaf color scale, and to operate the fertilizer application management with a high accuracy, compared to the leaf color scale.

Furthermore, in the configuration of the plant information acquisition system of the present invention, it is preferable that a plant information acquisition device including the imaging element, the optical system, the light source, the light shielding device, and the image processing device and a portable terminal including the plant information acquisition device are included, and the plant information acquisition device is connected to the portable terminal to be capable of transmitting the color information.

Furthermore, in the configuration of the plant information acquisition system of the present invention, it is preferable that a server including a database in which information relevant to cultivation of the plant is stored, corresponding to the plant information is included, the portable terminal is capable of being connected to the server such that data communication is capable of being performed with respect to the server through Internet by communication, and in a case where the plant information is received from the portable terminal, the server extracts the information relevant to the cultivation of the plant corresponding to the received plant information from the database, and transmits the extracted information relevant to the cultivation of the plant to the portable terminal.

Furthermore, in the configuration of the plant information acquisition method of the present invention, it is preferable that the plant information is acquired, and then the information relevant to the cultivation of the plant corresponding to the plant information is extracted from a database in which the information relevant to the cultivation of the plant is stored, corresponding to the plant information.

Furthermore, a plant information acquisition device of the present invention, which is provided in the plant in acquisition system, images the plant, and outputs the color information representing the color of the plant.

According to such a configuration, the plant information acquisition system is configured of the plant information acquisition device mainly performing imaging and the portable terminal mainly performing arithmetic processing, data display, or the like. The portable terminal, for example, includes a smart phone, a tablet type personal computer, or a laptop computer, and in general, a diffuse rate of the smart phone is high, and thus, the smart phone can be preferably used.

In this case, for example, in the data display or the like, a display of the smart phone can be used, and in a case where sound output is performed, a speaker of the smart phone can be used. Therefore, it is not necessary that the display or the speaker is provided in the plant information acquisition, device side. In addition, it is sufficient that the color information is obtained and output from the image signal output from the imaging element in the plant information acquisition device side, and thus, the plant information acquisition device basically has the configuration of camera except for the light shielding device, and it is sufficient that a comparatively narrow range of the plant is imaged at a close range, and thus, a great number of pixels is not required in the imaging element, an imaging element is not required in which pixels are arranged with a high density, and an inexpensive imaging element having a small number of pixels can be used. Therefore, a configuration which is less expensive than the chlorophyll meter or the like, can be used as the camera.

From the above description, in a case where the user possesses a smart phone, it is sufficient to purchase the plant information acquisition device corresponding to the camera which is less expensive than the chlorophyll meter or the like, and thus, it is possible to reduce the financial burden of the user. In addition, the arithmetic processing of acquiring the plant information from the color information is performed by the smart phone side, and thus, can be easily performed by the smart phone having high arithmetic capacity as the portable device. In addition, measurement date and time, a measurement spot, or the like can be automatically obtained by a clocking function of the smart phone side, the measurement of the current position according to a GPS sensor, or the like. In this case, a clock or the GPS sensor is not required in the plant information acquisition device side, and thus, it is possible to reduce the cost with respect to the clocking function or a position measurement function.

In addition, in the portable terminal such as the smart phone, the data communication using the internet can be performed by wifi or a public wireless communication network, the acquired plant information is allowed to access the server through the Internet, the information relevant to the cultivation of the plant which is associated with the acquired plant information can be obtained in a short period of time, and for example, the labor hour for searching the information relevant to the cultivation of the plant corresponding to the measurement data from the document described on the paper is not required. In addition, in the server side, a lot of users are able to collect, for example, the SPAD value as the measured plant information, in association with the measurement date and time and the measurement spot, and thus, in the fertilizer application management or the like corresponding to the SPAD value, it is possible to obtain useful information.

A crop management system of the present invention includes:

a user terminal that includes plant information acquired by the plant information acquisition system and transmits crop information which is information of a crop to be cultivated, including a growth state of the crop, period information representing an acquisition period of the crop information, and region information representing a region in which the crop information is acquired; and a management server that is capable of performing data communication with respect to the user terminal, receives the crop information, the period information, and the region information, includes management information storage device storing management information relevant to management of crop cultivation associated with the crop information, the period information, and the region information, and transmits the management information which is extracted from the management information storage device to a user terminal to which the crop information, the period information, and the region information are transmitted, on the basis of the crop information, the period information, and the region information.

A crop management method of the present invention is a crop management method in a crop management system including a user terminal, and a management server capable of performing data communication with respect to the user terminal, and in a case where crop information which is information of a crop to be cultivated, including a growth state of the crop, period information representing an acquisition period of the crop information, and region information representing a region in which the crop information is acquired are received from the user terminal, the management server extracts the management information on the basis of the crop information, the period information, and the region information which are received from the management information storage device storing management information relevant to management of crop cultivation associated with the crop information, the period information, and the region information, and transmits the management information to the user terminal.

According to such a configuration, for example, in a case where the user, who is an agriculture worker, acquires the crop information relevant to the growth of the crop to be cultivated by using a portable wireless terminal such as a smart phone, as the user terminal, inputs the crop information into the smart phone, and transmits the acquisition period of the crop information and the region information to the management server along with the crop information, it is possible to receive the management information by the smart phone.

In this case, it is not necessary for the agriculture worker to have a document or the like relevant to fertilizer application distributed by an autonomous community or the like, and in a case where there are provided the smart phone and an application (hereinafter, simply referred to as app) for performing data input and output, data communication with respect to the management server, and the like, it is possible to obtain the management information for the crop cultivation.

Therefore, for example, in the fertilizer application management, it is possible to easily obtain the management information or the like representing a fertilizer amount, and thus, an agriculture worker who has less experience or knowledge about the fertilizer application management or the fertilization management, is able to simply obtain the management information from a growth state of a useful crop to be cultivated.

In addition, it is possible to simply obtain the management information relevant to the crop cultivation, and thus, an agriculture worker who is acquainted with the fertilizer application management or the fertilization management, is also able to obtain the management information without taking labor hour, the way of the user own can be compared with the way of the management information output from the management server, and the fertilization management can be performed with reference to the management information.

In the configuration of the present invention, it is preferable that the user terminal includes an imaging device including the imaging element, the optical system, the light source, and the light shielding device in order to acquire image information obtained by imaging a part of a surface of the crop to be cultivated, as information for acquiring the crop information.

According to such a configuration, the user terminal includes the imaging device for acquiring an image of a crop surface by imaging a part of the surface of the crop, and thus, it is possible to transmit the image data to the management server from the user terminal as the crop information.

Furthermore, for example, in a case where the user terminal is the smart phone, including the imaging device in the user terminal includes connecting the imaging device as an external camera to the smart phone.

In addition, the image information obtained by performing imaging by the imaging device may be transmitted to the management server as the crop information, or for example, a color scale conversion value or an SPAD conversion value may be calculated by the user terminal from the image information as a converted leaf color value, and the converted leaf color value or the like may be transmitted to the management server as the crop information. In addition, in a case where the image information acquired by imaging the crop is transmitted as the crop information, the image information may be digitized to the converted leaf color value by the management server side. Here, the converted leaf color value is obtained on the basis of a correlative relationship between the image data and the SPAD value, is an SPAD conversion value correlated with the SPAD value, and is capable of being converted into a color scale value from the SPAD conversion value such that the SPAD value can be converted to the color scale value. In addition, the color scale value which is converted from the SPAD conversion value will be referred to as a color scale conversion value. Therefore, the converted leaf color value includes the SPAD conversion value and the color scale conversion value.

Basically, in a case where the leaf of the crop can be imaged in an approximately constant condition by shielding the outside light and by using the illumination of the illumination device, the SPAD conversion value or the color scale conversion value can be obtained from a correlative relationship between the color scale value or the SPAD value described above, and for example, RGB values, a luminance Y value, or the like of the image information, as the converted leaf color value.

From the above description, the crop is imaged, for example, by using a camera to be attached to the smart phone, a camera to be embedded in the smart phone, or the like, without obtaining the color scale value by using the leaf color scale which is difficult measure or using the chlorophyll meter which is comparatively expensive, and thus, for example, it is possible to obtain information (the converted leaf color value) such as the color scale conversion value or the SPAD conversion value, and on the basis of the information, it is possible to extract the management information in the management server. Accordingly, the agriculture worker is able to more easily obtain the management information.

Furthermore, in the configuration of the present invention, it is preferable that agricultural land information relevant to an area of an agricultural land in which the crop is cultivated is included in information which is transmitted from the user terminal and is received by the management server.

According to such a configuration, the agricultural land information including the information relevant to the area of the agricultural land in which the crop corresponding to the crop information is cultivated, is transmitted to the management server from the user terminal, in addition to the crop information, the period information, or the region information, and thus, in a case where a fertilizer amount per unit area at the time of performing the fertilizer application is stored in the management server, in association with the crop information, the period information, and the region information, the total fertilizer amount to be applied to the crop, or the like can be obtained on the basis of the fertilizer amount and the agricultural land information, and can be transmitted to the user terminal. In this case, not only the fertilizer amount per unit area but also a fertilizer amount to be actually used are obtained, and thus, it is possible to save the labor hour for calculation. Furthermore, the agricultural land information, for example, may be the area of the agricultural land, or may be information of the position of the corner of the agricultural land in which the shape of the size of the agricultural land can be recognized, and for example, may be four corner positions of a quadrangular land. In addition, in a case where the agricultural land information or the crop information includes information which becomes a measure of a cultivation density per unit area of the crop to be cultivated in the agricultural land, for example, information such as the number of plants or the number of stems per unit area, in the management server, the fertilizer amount may be changed according to the cultivation density.

Furthermore, in the configuration of the present invention, it is preferable that the management server extracts the management information stored in the management information storage device on the basis of the crop information, the period information, and the region information which are transmitted from the user terminal, and in a case where information of an amount of applied fertilizer per unit area is included in the extracted management information, the management server calculates the amount of applied fertilizer of the agricultural land on the basis of the information of the amount of applied fertilizer and the agricultural land information transmitted from the user terminal, and transmits the amount of applied fertilizer to the user terminal.

According to such a configuration, a specific fertilizer amount is output from the user terminal, and thus, the user is in a state of rarely taking labor hour for planning the fertilizer application management. Therefore, a user who has no experience or knowledge, is able to perform the fertilizer application management suitable for the growth state of the crop. In addition, the fertilizer amount is determined without taking labor hour, and thus, for example, a user who has abundant experience or knowledge is able to easily compare the fertilizer amount with a fertilizer amount determined by the user, and there is a possibility of offering an opportunity to be used by the user.

The plant information acquisition system of the present invention includes: an abnormal value sensing device configured to set the color information or the plant information to an abnormal value in a case where the acquired color information or the acquired plant information satisfies an abnormal value determination condition which is set.

According to such a configuration, the abnormal value is sensed by an abnormality sensing device, and thus, for example, it is possible to eliminate the abnormal value as the measurement result or to perform remeasurement.

A main cause for occurring the measurement abnormality includes a first cause in which the object is shifted from an imaging range at the time of performing imaging, and there is a portion where the object is not imaged in a part of the imaging range, a second cause in which the outside light which is not capable of being shielded by the light shielding device, enters at the time of performing imaging, and a third cause in which contamination or flaw occurs on an imaging portion of the object.

In a case of the first cause, for example, at least a part of a circumferential portion of an image which is imaged in a predetermined range becomes dark by exceeding the lower limit value which is set (the color becomes dense) or becomes bright by exceeding the upper limit value (the color becomes pale), and thus, on the basis of this, it is possible to determine the abnormal value. In a case of the second cause, the image is brighter than a predetermined threshold value due to the entrance of the outside light, and thus, it is possible to determine the abnormal value, but in a case where a green leaf of a plant is set to the object, it is possible to determine a case where the value of blue B of RGB becomes bright (dense) by exceeding the threshold value, as abnormal. In a case of the third cause, a standard deviation $\sigma$ of the color information or the plant information is obtained by performing imaging a plurality of times, and thus, for example, it is possible to determine color information or plant information exceeding a range of $2\sigma$ as abnormal. In this case, it is not possible to determine the abnormality from one image, one color information item, or one plant information item, but in general, in the measurement of the plant information, a plurality of times of the measurement is performed at a time, and thus, it is possible to obtain the standard deviation $\sigma$, and accordingly, it is possible to determine the abnormality. Furthermore, a case where an abnormality determination condition, which is a condition to be determined as abnormal, is satisfied, is determined as abnormal, and in a case where a condition to be determined as normal is not satisfied, it is possible to determine that the abnormality determination condition is satisfied.

Furthermore, the plant information acquisition system of the present invention includes:

a display device configured to display an image based on the image signal or the color information which is acquired from the image signal as a color; and a display control device configured to cause the display device to display the image or the color and to display a comparative image or a comparative color which becomes a comparative target.

According to such a configuration, it is possible to measure an image or a color while comparing, the image or the color, which becomes the measurement result, with an image or a color, which becomes the comparative target, or to visually confirm the measurement result. In a case where a plurality of times of the measurement is performed at a time as the comparative target, an image or a color measured before the current measurement among the plurality of times of the measurement can be displayed as the comparative image or the comparative color, and in this case, it is possible to confirm the degree of variation in one time of the measurement and to pause or eliminate measurement which is assumed as abnormal. In addition, the comparative target may be a color or image data in the same period of the past such as the last year, and the color or the image data of a plant in other fields, agricultural fields, or the like which are provided. By setting a color or an image in a state where the growth is excellent to the comparative target, it is possible to determine the growth state to a certain degree. In addition, in the case of being instructed on agricultural works, it is possible to perform instruction to be easily understood by instruction which is performed while comparing the comparative target with the current measurement result. In addition, comparative display may be performed at the time of performing measurement, or may be performed after measurement.

In the configuration of the present invention, it is preferable that the color information is a representative value of each color component of a value corresponding to each color component of each pixel of an image in a predetermined range which is imaged by the imaging element.

According to such a configuration, a color as each measurement result is not changed according to a portion of a leaf as with the image of the leaf, but can be displayed as a surface having a uniform color. Accordingly, measurement results are easily visually compared with each other, compared to a case where a color is changed according to a position as with the image of the leaf at the time of performing comparison. Here, a color component, for example, is each color component, for example of red R, green G, and blue B as the color space, and may be color components of other than RGB, or may be gray obtained from each value of RGB.

Furthermore, in the plant information acquisition system of the present invention, the image processing device is adjusted such that the plant information acquisition device is capable of acquiring the plant information which approximates to predetermined plant information, by using the optical system, the light source, and the light shielding device, at the time of imaging a calibration object corresponding to the predetermined plant information.

According to such a configuration, in imaging using the imaging element, the optical system, the light source, and the light shielding device, due to an individual difference thereof, it is possible to decrease a difference in the color information or the plant information to be output according to a difference in the plant information acquisition device (a camera) of the plant information acquisition system, even in the case of imaging plants having the same color. Furthermore, the imaging element and the image processing device may be configured in one chip, or may be individually configured of two chips.

Advantageous Effects of Invention

According to the present invention, it is possible to acquire the plant information from the color information representing the color of the plant which is imaged by the imaging element. In this case, the plant information is obtained by the plant information acquisition device which basically has a basic configuration as a camera, and thus, it is possible to acquire the plant information at a low price, compared to a dedicated colorimetric analyzing device. In addition, it is possible to easily perform the fertilizer application management or the fertilization management based on the growth state of the crop.

BRIEF DESCRIPTION OF DRAWINGS

FIG. 1 is a block diagram illustrating a plant information acquisition device of a plant information acquisition system, in an embodiment of the present invention.

FIG. 2 is a schematic diagram illustrating the plant information acquisition device, in the embodiment of the present invention.

FIG. 3 is a schematic diagram illustrating the plant information acquisition system, in the embodiment of the present invention.

FIG. 4 is a flowchart for illustrating plant information acquisition processing which is performed by the plant information acquisition device, in the embodiment of the present invention.

FIG. 5 is a flowchart for illustrating plant information acquisition processing which is performed by a portable terminal, in the embodiment of the present invention.

FIG. 6 is a flowchart for illustrating plant information acquisition processing which is performed by a server, in the embodiment of the present invention.

FIG. 7 is a process chart for illustrating a calibration method which is performed by the plant information acquisition device, in the embodiment of the present invention.

FIG. 8 is a diagram for illustrating the calibration method which is performed by the plant information acquisition device, in the embodiment of the present invention.

FIG. 9 is a block diagram illustrating a crop management system, in a second embodiment of the present invention.

FIG. 10 is a flowchart for illustrating main processing at the time of activating a crop management app, which is per formed by a smart phone and a management server, in the second embodiment of the present invention.

FIG. 11 is a flowchart for illustrating login processing of the crop management app, which is performed by the smart phone and the management server, in the second embodiment of the present invention.

FIG. 12 is a flowchart for illustrating initial setting processing of the crop management app, which is performed by the smart phone and the management server, in the second embodiment of the present invention.

FIG. 13 is a flowchart for illustrating cultivation information input processing of the crop management app, which is performed by the smart phone and the management server, in the second embodiment of the present invention.

FIG. 14 is a flowchart for illustrating measurement determination processing of the crop management app, which is performed by the smart phone and the management server, in the second embodiment of the present invention.

FIG. 15 is a diagram for illustrating display of the smart phone after a converted leaf color value is measured, in the second embodiment of the present invention.

FIG. 16 is a diagram for illustrating the display of the smart phone after the converted leaf color value is measured in a plurality of measurement points, in the second embodiment of the present invention.

FIG. 17 is a graph illustrating measurement of a leaf color and past history of a standard value by comparing the measurement with the past history, in the second embodiment of the present invention.

FIG. 18 is a diagram illustrating an example of gradually displaying a difference between a converted leaf color value and a leaf color standard value in an area of an agricultural field in which each measurement point is included, on a map with a color as a display of a terminal such as a smart phone, in the second embodiment of the present invention.

FIG. 19 is a diagram illustrating an example of gradually displaying a difference between the converted leaf color value and the leaf color standard value in each agricultural field, on a map with a color as the display of the terminal or the like, in the second embodiment of the present invention.

FIG. 20 is a diagram for illustrating a test condition, in an example of the present invention.

FIG. 21 is a graph illustrating a result of single regression analysis, in the example of the present invention.

FIG. 22 is a diagram for illustrating a narrowing method of an independent variable of multiple regression analysis, in the example of the present invention.

FIG. 23 is a diagram illustrating data which becomes the independent variable and is used for narrowing the independent variable of the multiple regression analysis, in the example of the present invention.

FIG. 24 is a diagram illustrating an analysis result of narrowing the independent variable of the multiple regression analysis, in the example of the present invention.

FIG. 25 is a diagram illustrating a correlation coefficient R, a freedom degree-adjusted determination coefficient $R^2$, and an explanatory variable selection standard Ru in the analysis result of narrowing the independent variable of the multiple regression analysis, in the example of the present invention.

FIG. 26 is a diagram illustrating a (multiple) determination coefficient $R^2$ and significance F as the result of the multiple regression analysis in each test condition, in the example of the present invention.

FIG. 27 is a graph illustrating the (multiple) determination coefficient $R^2$ as the result of the multiple regress ion analysis in each of the test conditions, in the example of the present invention.

FIG. 28 is a diagram illustrating an analysis result of top two test conditions of the (multiple) determination coefficient $R^2$ among multiple regression analysis results in each of the test conditions, in the example of the present invention.

FIG. 29 is a graph illustrating a correlative relationship between an SPAD conversion value calculated by a correlation equation which is obtained with respect to a test condition selected from all test conditions and an SPAD value measured by a chlorophyll meter, in the example of the present invention.

FIG. 30 is a diagram for illustrating a calculation method of the shortest distance between a multiple regression line and each plot of FIG. 29.

FIG. 31 is a graph illustrating a frequency distribution of the shortest distance between the multiple regression line and each of the plots of FIG. 29.

FIG. 32 is a diagram for illustrating a sensing method of an abnormal value in a third embodiment of the present invention.

FIG. 33 is a flowchart for illustrating the sensing method of the abnormal value, in the third embodiment of the present invention.

FIG. 34 is a diagram for illustrating comparative display of data on a display screen of the smart phone in a fourth embodiment of the present invention.

FIG. 35 is a diagram for illustrating the comparative display of the data on the display screen of the smart phone, in the fourth embodiment of the present invention.

FIG. 36 is a diagram for illustrating the comparative display of the data on the display screen of the smart phone, in the fourth embodiment of the present invention.

FIG. 37 is a diagram for illustrating the comparative display of the data on the display screen of the smart phone, in the fourth embodiment of the present invention.

FIG. 38 is a diagram for illustrating the comparative display of the data on the display screen of the smart phone, in the fourth embodiment of the present invention.

MODE FOR CARRYING OUT THE INVENTION

Hereinafter, a first embodiment of the present invention will be described.

A plant information acquisition system of this embodiment acquires information of a plant on the basis of image data obtained by imaging the surface of the plant. In this embodiment, a leaf color density (for example, a conversion value of an SPAD value or a conversion value of a leaf color scale) is obtained, for example, from the values of a plurality of variables configuring a color space of red, green, and blue (RGB) of the image data.

As illustrated in FIG. 1 and FIG. 2, a plant information acquisition device 101 (a crop information acquisition device: a camera 30 of a crop management system) of the plant information acquisition system of this embodiment is formed of a device main body 32, and a receiving member 33 including a receiving surface facing the device main body 32, a base portion of the receiving member 33 is rotatably fixed to the device main body 32, and thus, for example, the receiving member 33 has a stapler (hotchkiss)-like structure. That is, a base end portion of the receiving member 33 is rotatable connected to the device main body 32, and thus, interposes, for example, a leaf, which becomes a measurement target, between a tip portion side of the receiving member 33 and the device main body 32.

Furthermore, the receiving member 33 can be rotated with respect to the device main body 32 by an angle in a predetermined range and is biased to have a maximum angle in the predetermined range by a biasing device (not illustrated) such as a spring. In such a state, the tip portion of the receiving member 33 is brought close to the device main body 32 against a biasing force, and thus, can be retained in a state of interposing the leaf.

The device main body 32 includes an imaging element (an image sensor) 41, a lens 40 for forming an image on the imaging element 41, as an optical system, an illumination white LED (a light source) 42, a polarizing plate 43 (43*a* and 43*b*) for preventing reflection light, a hood 34 for shielding outside light, and an On-Off switch 35, as an imaging device. In addition, the device main body 32 includes a control circuit 50 controlling at least on and off of the white LED 42, the imaging element 41, and various circuits, an image processing circuit 51 processing each signal of RGB output from the imaging element 41, a data processing circuit 52 calculating an independent variable from image data of an RGB space output from the image processing circuit 51, and a communication circuit 53 performing data communication with respect to a portable terminal 130 (a smart phone 1) described below. The communication circuit 53 and the portable terminal 130 are connected to each other by a wireless manner (bluetooth (Registered Trademark); WiFi) or a wired manner (a USB cable or the like). On the other hand, a surface of the receiving member 33 facing the device main body 32 is a flat surface, and a positioning guide 36 is disposed in a position corresponding to an imaging position of the device main body. The positioning guide 36 is a convex portion protruding to right and left from the receiving member 33 in a width direction (in a depth direction from the front side in FIG. 2), and includes a flat portion in an upper portion continuous with the flat surface of the receiving member 33. A linear concave portion representing the center of an imaging range of the camera is disposed in the center portion of each of right and left positioning guides 36. The concave portion functions as a mark for positioning the leaf on the center of the imaging range. Therefore, when a leaf of a rice plant is interposed in a state where the leaves are arranged from the concave portion of one of the right and left positioning guides 36 to the concave portion of the other positioning guide 36, it is possible to dispose the leaf on the center of an optical visual field of the camera. Therefore, the concave portion of the positioning guide 36 becomes a mark for disposing the leaf of the rice plant on the center of the imaging range of the camera at the time of disposing the leaf on the receiving member, and is capable of manually fixing the leaf such that the leaf is not moved with respect to the receiving member 33 until immediately before interposing the leaf. Even in a case where the concave portion is not disposed, a mark for disposing the position of the positioning guide 36 itself on the center may be provided.

The hood 49 for shielding outside light is formed of a black urethane material, and the height of the hood 49 for shielding outside light and the height of the shutter switch 35 which is turned on are set such that the leaf is not damaged at the time of being imaged in an interposed state and the shutter switch 35 is turned on in a state where sufficient outside light is shielded by the hood 49 for shielding outside light.

The imaging element 31 is a charged coupled devices (CCD) sensor or a complementary metal-oxide-semiconductor (CMOS) sensor including a color filter. The lens 40, for example, a close-up single focus lens. The white LED 42 is an illumination for imaging the leaf, and in this embodiment the hood 34 described above is pressed against the surface of the leaf at the time of imaging the leaf, and the leaf is imaged by light of the white LED 42 in a state where the outside light is shielded. At this time, the leaf is in a state of being interposed between the device main body 32 and the receiving member 33, and the receiving member 33 is in a state where outside light in a direction, which is transmitted through the leaf is shielded. Therefore, a light shielding device shielding the outside light at the time of performing imaging, is configured of the hood 34 described above and the receiving member 33.

In addition, in order to prevent reflection light of the white LED 42 close to an object, for example, from being in a state of being reflected on the surface of the leaf (for example, a state of being close to a reflection on a mirror), a polarizing plate 43 is used. As illustrated in FIG. 2, the polarizing plate 43 is formed of a polarizing plate 43*a* through which illumination light of the white LED 42 is transmitted, and a polarizing plate 43*b* through which reflection light of the leaf as the object is transmitted, and the polarizing plate 43*a* and the polarizing plate 43*b* are in a state where polarization directions of the polarizing plate 43*a* and the polarizing plate 43*b* are orthogonal to each other. Accordingly, direct reflection light of the illumination light of the white LED 42 which is emitted to the leaf through the polarizing plate 43*a* is shielded by a pair of polarizing plates 43*a* and 43*b*, and thus, for example, the white LED 42 is prevented from being in a state of being reflected on the surface of the leaf, and the color of a surface layer of the leaf is viewed.

In addition, in this example, a half mirror 44 is used, and thus, the illumination light is incident on the leaf by being transmitted through the half mirror 44, and the reflection light from the leaf is guided to the lens 40 by being reflected on the half mirror 44. In addition, as described above, the leaf is interposed between the device main body 32 and the receiving member 33 in the position of the hood 34, and thus, a state is obtained in which the cylindrical hood 34 is pressed against the leaf, and the outside light entering from an opening for imaging can be prevented from being directed towards the imaging element 41 side. That is, it is possible to shield the outside light. In addition, the hood 34 is formed to limit the imaging range, and the imaging range is narrower than an effective pixel portion of the imaging element 41. Furthermore, in the case of interposing the leaf, there is concern that the leaf is damaged and is discolored, and thus, it is preferable that the hood 34 has a smooth shape without having a protrusion or the like on the surface. In addition, in order to improve light shielding properties and to prevent the leaf from being damaged, the hood 34 may be formed of a material having high flexibility to be elastically deformed at the time of manually performing an interposing operation.

In this embodiment, for example, a converted leaf color value (an SPAD conversion value) as an index representing the content of chlorophyll is obtained from the color of the leaf, as plant information (crop information), and at this time, the SPAD conversion value correlated with an SPAD value is obtained on the basis of a correlative relationship with respect to the SPAD value which can be converted into a color scale value. For this reason, for example, each value of RGB of each pixel in a predetermined range (a predetermined area) of the image data obtained by performing imaging, and the value of Gray obtained from each of the values of RGB are used. Furthermore, when RGB values of each of the pixels are obtained, for example, signals of RGB output from the imaging element 41, are subjected to image processing by the image processing circuit (an image processing device) 51, and are output as a signal of each color of RGB. In addition, in a case where the imaging element 41 is a single pixel type imaging element, each of the pixels is formed of a pixel of R, a pixel of G, and a pixel of B, corresponding to the pattern of a color filter, and the RGB values of each of the pixels are obtained by synchronization processing (interpolation processing).

In this embodiment, signals from a plurality of pixels in a predetermined range in the imaging range based on the optical system are used. The predetermined range described above, for example, is approximately 200 pixels×200 pixels in 2 mm×2 mm, but is not particularly limited thereto. Each value of RGB of each of the pixels included in the predetermined range, and the value of Gray obtained from the values of RGB are used. The value of Gray is obtained from each of the values of RGB by the following equation.

$$Gray=R\times0.3+G\times0.59+B\times0.11$$

Furthermore, the image data is not limited to RGB and Gray, and HSV, HLS, YUV, YCbCr, YPbPr, or the like may be used. Basically, in a case where there is a correlative relationship with respect to a color scale value or a chlorophyll density (the SPAD value) as crop information to be obtained, a color space other than RGB may be used.

In addition, each of the values of RGB or the value of Gray are obtained, but values of each of the pixels in the predetermined range to be used in the imaging range described above are not necessarily required, and a representative value of data relevant to colors of each of the pixels in the predetermined range of the image data obtained by performing imaging, that is, representative values of each of the values of RGB and the value of Gray are respectively obtained, and for example, the converted leaf color value (the SPAD conversion value) is obtained on the basis of a correlative relationship with respect to the representative value. An average value, a center value, a mode value, an integral value, or various values which can be the representative value, can be adopted as the representative value representing a main tendency of the population. In this embodiment, the average values of each of the values of RGB and the value of Gray of each of the pixels in the predetermined range of the image data are respectively obtained as the representative value.

Furthermore, the plant information (the crop information) which can be acquired is not limited to the converted leaf color value, and for example, may be a nitrogen content having correlativity with the chlorophyll density or the SPAD value. Basically, a value having a correlative relationship with respect to the value of a variable of RGB or the like of each of the pixels configuring the image data, can be the crop information which can be acquired. For example, in a case where there is a correlative relationship between the color of a fruit and a growth situation such as a sugar concentration, a citric acid concentration, other acid concentrations, a polyphenol concentration, and a mature degree, information of the sugar concentration or the concentrations of various acids or information of the concentrations of various polyphenols or the growth situation may be acquired as the crop information. In addition, it is determined whether or not predetermined diseases are developed, by using the values of RGB or the like described above.

In addition, the switch 35 turns on and off the white LED 42 and the imaging element 41 through the control circuit 50, and for example, functions as turning On-Off of the illumination and as a shutter. As described, above, in a case where the receiving member 33 is brought close to the device main body 32 against the biasing force of the biasing device, the switch 35 on the device main body 32 side is pressed by the receiving member 33 and thus, is turned on, and in a case where the receiving member 33 is separated from the device main body 32, the switch 35 is turned off. In a case where the switch 35 is turned on, a power source of a circuit board on which the control circuit 50, the imaging element 41, the image processing circuit 51, or the like is mounted, is turned on. In addition, according to the control of the control circuit 50 which is turned on by the above operation, the illumination white LED 42 is turned on, and then, the shutter is turned on. At this time, in a case where the leaf is interposed between the receiving member 33 and the hood 34 of the device main body 32, the surface of the leaf is imaged in a state where light is shielded by the hood 34. At this time, light which is transmitted through the leaf is shielded by the receiving member 33. Furthermore, the number of switches 35 is not limited to one, and a power source switch of the circuit board on which the imaging element 41, the image processing circuit 51, or the like is mounted, a power source switch of the illumination white LED 42, a shutter switch, and the like may be respectively disposed. In this case, the switch 35 only functions as a shutter button for capturing a static image, and thus, a moving image of the current input image may be displayed with respect to the smart phone until the switch 35 is pressed. Accordingly, it is possible to press the switch while confirming an image, and thus, is possible to image a suitable static image.

In addition, in this embodiment, the switch 35 is in contact with the receiving member 33, and thus, is turned on, and the switch 35 may be turned on, for example, in a case where the receiving member 33 is rotated and moved by a predetermined angle, or may be a touch sensor disposed on a predetermined portion. In addition, the switch 35 may be an illumination intensity sensor (for example, a light receiving element) disposed in the hood, and the illumination white LED 42 may be turned on when illumination intensity is decreased by shielding the outside light, the illumination intensity sensor may sense that the white LED 42 is turned on, and thus, the shutter may be turned on.

The lens 40, for example, is a close-up single focus macrolens, and is brought to a focus on the object (the leaf) blocking the hood 34 by being in contact with the tip of the hood 34.

The control circuit 50 controls the driving or the like of the white LED 42 and the imaging element 41 as described above, and may further control the driving or the like of the image processing circuit 51, the data processing circuit 52, and the communication circuit 53.

The image processing circuit 51 performs the synchronization processing described above based on the image signal output from the imaging element 41, obtains the value of Gray of each of the pixels from the values of RGB of each of the pixels in the predetermined range, and outputs each of the values of RGB and the value of Gray of each of the pixels. In the data processing circuit (the image processing device) 52, the average value (the representative value) of each of the values of RGB of each of the pixels and the average value (the representative value) of Gray of each of the pixels are obtained. That is, the average value of R, the average value of G, the average value of B, and the average value of Gray are obtained, and these values are output to the communication circuit 53. In the communication circuit 53, the camera 30 is capable of performing communication with respect to a smart phone (the smart phone 1: a user terminal) as the portable terminal 130, through wire communication, for example, using USB or a wired LAN (Ethernet (Registered Trademark)) or wireless communication, for example, using WIFI (a wireless LAN) or bluetooth (Registered Trademark), and thus, each of the average values of RGB of the image data obtained by imaging the leaf described above and the average value of Gray are transmitted.

That is, as illustrated in FIG. 3, the plant information acquisition device 101 is connected to the portable terminal 130, and the portable terminal 130 can be connected to a server 143 through a wireless public line network and the Internet 142. The portable terminal 130 includes a wireless communication device for performing sound communication and data communication through a wireless public line network, a control device (the plant information acquisition device) controlling various communications and executing an installed application (hereinafter, simply referred to as app), a display (a display device) for performing display based on the execution of the app or a system (OS), a display control device displaying an image on the display on the basis of the execution of the app or the like, a sound control device controlling the input and output of sound, and various sensors including a GPS, as a portable telephone (the smart phone 1).

In addition, the portable terminal 130 includes the app or a flash memory as a storage which is used in the app. Furthermore, an RAM as a memory which is used in a program of the app or the like, for example, is provided in the control device.

In addition, an app for plant information acquisition processing (plant information acquisition device) is preinstalled in the flash memory, and the SPAD conversion value, which is an index of a chlorophyll amount, is calculated with respect to the representative values (the average values) of RGB and Gray described above transmitted from the plant information acquisition device 101 (the camera 30).

For example, a (multiple) regression equation (a correlation equation) between the representative value described above and the SPAD conversion value, which is obtained by regression analysis or multiple regression analysis, is registered in the app for plant information acquisition processing (an app for crop management). For example, a multiple regression equation for calculating the SPAD conversion value from the average value of G of each of the average values of RGB and the average value of Gray is registered. Accordingly, in a case where each of the average values of RGB and the average value of the Gray are received from the plant information acquisition device 101, the SPAD conversion value is output from the portable terminal 130 on the basis of the average value of G and the average value of Gray.

For example, in a case where the converted leaf color value (the SPAD conversion value) is set to Y, the average value of G is set to X1, and the average value of Gray is set to X2, the multiple regression equation becomes $Y=a(X1)+b(X2)+c$. In this equation, the average value (the independent variable) of the values of G of the plurality of pixels in the predetermined range of the image data obtained by performing imaging is substituted into X1, and the average value (the independent variable) of Gray of the plurality of pixels in the predetermined range of the image data is substituted into X2, and thus, the SPAD conversion value, which is Y dependent variable) is calculated.

In addition, the obtained SPAD conversion value, the variety of the rice plant, which is input into the portable terminal 130, a region (an address) in which the rice plant is cultivated, the current date, and the height of the rice plant are transmitted to the server 143 as data for performing fertilizer application management. The server 143 basically stores the SPAD conversion value and the height of the rice plant corresponding to the region, the current date, and the variety. The SPAD conversion value corresponding to the region, the current date, and the variety is searched and extracted by the region (the address) and the current date, the SPAD value which is registered is compared with the measured SPAD conversion value. Similarly, the height of the rice plant which is registered is compared with the input height of the rice plant. Furthermore, for example, a value which is measured by height measurement software installed in the portable terminal 130, may be transmitted as the height of the rice plant.

In a case where the SPAD conversion value which is measured is less than the SPAD conversion value which is registered, it is possible to determine that a nitrogen fertilizer is insufficient, whereas in a case where the SPAD conversion value which is measured is greater than the SPAD conversion value which is registered, there is a possibility that the nitrogen fertilizer is sufficient or the amount of nitrogen fertilizer is greater than a requisite amount. In addition, in a case where the measured SPAD conversion value is less than the registered SPAD conversion value, and the measured height of the rice plant is lower than the registered height of the rice plant, the fact that the fertilizer is insufficient is supported, and in a case where the measured SPAD conversion value is greater than the registered SPAD conversion value, and the measured height of the rice plant is higher than the registered height of the rice plant, a possibility that the fertilizer is excessively sufficient, is high.

The SPAD conversion value, which becomes a standard as described above, is registered in the server 143 according to the region, the date (or the number of days from insemination or rice planting), and the variety, and for example, guidance is registered with respect to the measured SPAD conversion value. For example, in a case where the measured SPAD conversion value is less than the SPAD conversion value, which becomes the standard, basically, guidance for urging fertilizer application of the nitrogen fertilizer or the like is registered, and in a case where the measured SPAD conversion value is greater than the SPAD conversion value, which becomes the standard, guidance for avoiding the fertilizer is registered.

In addition, not only the fertilizer application management but also guidance of water management, weeding, diseases countermeasure, or the like are obtained according to the season, the region, and the variety. There are guidance which is relevant to the SPAD conversion value and guidance which is not relevant to the SPAD conversion value. Furthermore, currently, in the SPAD conversion value, guidance including the fertilizer application management with respect to the measured SPAD conversion value is provided in an organization (an agricultural cooperative, an agricultural experiment station, an administrative institution, or the like) relevant to rice cultivation in each region, and the guidance can be used.

In a plant information acquisition method of such a plant information acquisition device 101, for example, as illustrated in a flowchart of FIG. 4, the plant information acquisition processing is performed by the plant information acquisition device 101 (the camera 30) of this embodiment, which is one type of camera.

At this time, the leaf is imaged.

In the imaging of the leaf, for example, a normal leaf which is approximately identical to other leaves is selected. The leaf is interposed between the device main body 32 and the receiving member 33 in the position of the hood 34 of the camera 30. According to such an operation, the switch 35 is turned on from off (step S1), the control circuit 50 mounted on the camera 30 is turned on, and the white LED 42 is turned on, the imaging element 41 is activated, the image processing circuit 51 is activated, the data processing circuit 52 is activated, and the communication circuit 53 is activated, on the basis of the control of the control circuit 50 (step S2). Such circuits may be on one chip.

Next, imaging is automatically performed, by using the fact that the switch is turned on as a trigger (step S3). In the image processing circuit 51, the signal output from the imaging element 41 is subjected to the synchronization processing as described above, and the image data is generated. At this time, the data of Gray is also calculated from the data of RGB. That is, the values of RGB and Gray of each of the pixels are calculated (step S4), the values of RGB and Gray of each of the pixels are transmitted to the data processing circuit 52 (step S5). In the data processing circuit 52, a representative value of R, a representative value of G, a representative value of B, and a representative value of Gray are calculated from the value of R, the value of G, the value of B, and the value of Gray of each of the pixels in the predetermined range of the image data (step S6). The representative value of R, the representative value of G, the representative value of B, the representative value of Gray, and the image data are transmitted to the smart phone (the portable terminal 130) 1 through the communication circuit 53 (step S7). Furthermore, each of the representative values may be obtained from the image data described above by the smart phone 1.

As illustrated in a flowchart of FIG. 5, in a case where each of the representative values described above is input into the portable terminal 130 from the plant information acquisition device 101 (step S11), each of the representative values is substituted into the relational equation between the representative value and the SPAD conversion value described above, and thus, the SPAD conversion value (the converted leaf color value) is calculated (step S12). That is, the representative value of G and the representative value of Gray are substituted into multiple regression equation based on a correlation between the SPAD value and the representative value of each color described above, and thus, the converted leaf color value is obtained.

The obtained converted leaf color value is displayed on the display of the portable terminal 130 along with data such as the address, the date, or the variety described above as the other data (step S13). At this time, the image data obtained by performing imaging may be displayed. The data displayed on the display can be transmitted to the server 143, and the display of data other than the SPAD conversion value is displayed to be directly changed. In a case where a user changes the data (step S14), correspondingly, the data stored in the portable terminal 130 is changed, updated, and stored (step S15). Next, the height of the rice plant is input (step S16). Furthermore, the height of the rice plant may be input by being measured by the user, and the height of the rice plant may be calculated and input by providing a known height measuring function in the app for plant information acquisition processing and by performing imaging by the camera of the portable terminal 130.

The obtained SPAD value is transmitted to a database which is registered in the server 143 (step S17). As illustrated in a flowchart of FIG. 6, in a case where data such as the SPAD value is received in the server 143 from the portable terminal 130 (step S21), the database of the server 143 is searched on the basis of the region, the date, the variety of the rice plant, the SPAD value, and the height of the rice plant described above (step S22), data relevant to the fertilizer application management of whether or not the fertilizer is applied, the amount of applied fertilizer per unit area in the case of applying the fertilizer, or the like is obtained (step S23). Information relevant to the fertilizer application management which is obtained by the search is transmitted to the portable terminal 130 (step S24).

In a case where the information relevant to the fertilizer application management is received in the portable terminal 130 (step S18), the information is displayed (step S19). Information relevant to whether or not the fertilizer is applied, described above, a fertilizer amount per unit area in the case of applying the fertilizer, and other agricultural works of the rice plant is received in the portable terminal 130, and is displayed on the portable terminal 130.

In a case where each of the representative values described above is input into the mart phone (the portable terminal 130) 1 from the camera 30, each of the representative values is substituted into the relational equation between the representative value and the converted leaf color value (the SPAD conversion value) described above, and thus, the converted leaf color value is calculated. It is known that there is a correlative relationship between the SPAD value and a read value of a leaf color scale of green, and the converted leaf color value is measured by using the values of G and Gray in RGB+Gray. That is, the representative value of G and the representative value of Gray are substituted into the multiple regression equation based on the correlation between the converted leaf color value (the SPAD conversion value) and the representative value of each color described above, and thus, the converted leaf color value is obtained.

The obtained converted leaf color value is displayed on the display of the smart phone 1 along with the data such as the address, the date, or the variety described above as the other data. At this time, the image data obtained by performing imaging may be also displayed. The data displayed on the display can be transmitted to the server 143 (a management server 10 described below), and the display of data other than the converted leaf color value is displayed to be directly changed. In a case where the user changes the data, correspondingly, the data stored in the smart phone 1 is changed, updated, and stored. Next, the height of the rice plant is input. Furthermore, the height of the rice plant may be input by being measured by the user, and the height of the rice plant may be calculated and input by providing a known height measuring function in the app for plant information acquisition processing and by performing imaging by the camera 30.

Next, the process of a calibration method of the camera 30 will be described by using FIG. 7. In the camera 30, the plant information (the crop information) is obtained according to the color. At this time, an individual difference, a temporal change, or the like of each of the cameras 30 is required to be calibrated.

A color chip, which becomes a predetermined SPAD conversion value (a calibration standard value) in the case of performing measurement by a chlorophyll meter, for example, is bundled with the camera 30 at the time of selling the camera 30 (step St1). The user performs calibration by using the color chip (step St2). It is preferable that the calibration is performed at the start of use, and is approximately periodically performed for each set period as far as possible.

First, the camera 30 is connected to the portable terminal 130 (the smart phone 1), and the app for plant information acquisition processing (the app for crop management) is activated.

Calibration processing is processing performed by the smart phone 1 to which the camera 30 is connected, and processing from step S31 described below is the processing performed by the smart phone 1.

For example, a submenu in which items such as calibration are displayed as a button, can be displayed on the display of the smart phone 1 in which the crop management app is activated. In a case where the calibration processing is performed, the user presses a calibration button, and thus, the smart phone 1 senses that a touch screen is touched in a range of the display where the calibration button is displayed (step S31). Here, the app for crop management is activated, and then, a standby state is obtained by monitoring the detection of the touch of each button displayed as a menu, and the touch of the calibration button is sensed, and thus, the calibration processing starts (step S32).

A display which urges that the bundled color chip is imaged a predetermined, number of times (for example, five times or ten times) and represents that the color chip is imaged by being interposed between the device main body 32 and the receiving member 33, is displayed on the display of the smart phone 1, and a standby state is obtained by monitoring the input of the image data obtained by performing imaging by the camera 30. At this time, the number of times of input of the image data is counted, and a display which urges that the color chip is continuously imaged, is displayed on the display until a count value of the number of times of input becomes the predetermined number of times described above. Correspondingly, the user images the color chip, and thus, the image data is sequentially input into the smart phone 1 (step S33).

In the smart phone 1, the input image data is acquired, and is stored in a storage device such as a flash memory (step S34).

In the control device of the smart phone 1, the average value as the representative value of the value of G in the values of RGB of each pixel in a predetermined range of a predetermined number of image data items obtained by imaging the color chip and the value of Gray of each of the pixels in the predetermined range are calculated from the values of RGB, and the average value as the representative value of the value of Gray of each of the pixels in the predetermined range is obtained. That is, the average value of a G value and a Gray value of each of the pixels in the predetermined range is obtained. Such an operation is performed with respect to all of a predetermined number of image data items, and each one of the G value and an R value averaged in each of the image data items is obtained, and then, the average value (the representative value) of the G value and the Gray value in each of the predetermined number of image data items is obtained.

The calculated G value and the calculated Gray value are substituted into the regression equation described above, and thus, the SPAD conversion value is obtained. A difference between the converted leaf color value obtained by imaging the color chip and the leaf color value, which becomes a standard set in the color chip, is calculated and determined as correction data (step S35).

The calculated correction data is automatically registered in the smart phone 1 (step S36), and the processing ends (step S37). Hereinafter, when an SPAD conversion value based on an imaged image of an actual leaf is calculated, the SPAD conversion value is corrected by using the correction data. That is, it is possible to obtain the converted leaf color value in a state of being calibrated from the average value of G and the average value of Gray by using a correlation equation in which a correction value is substituted into a correction term set in the regression equation.

Here, the correction data is registered in the smart phone 1, but is not limited thereto, and may be registered in the server 143, or may be registered in both of the smart phone 1 and the server 143. In a case where the SPAD conversion value described below is calculated by the server, but not by the smart phone 1, the processing can be simplified. In addition, in a case where the correction data is constantly registered in the server along with the history, the server checks a fluctuation in the correction value, and thus, it is possible to grasp the degradation of the performance of the camera 30, to urge the user to take precautions, and to prevent an abnormal imaged image and an abnormal SPAD conversion value from being registered in the database.

As described above, the multiple regression equation is represented by Y=a(X1)+b(X2)+c, and is corrected to Y=a(X1)+b(X2)+c+α by using a correction term (α). That is, the correction value calculated as described above is substituted into α, and the converted leaf color value as a dependent variable Y is obtained.

For example, in FIG. 8, regression analysis is performed by setting the converted leaf color value (the SPAD conversion value) obtained by being calculated from image data of the leaf to an independent variable X, and by setting the SPAD value in a case where the leaf is measured by a chlorophyll meter, to the dependent variable Y, and as the result of the regression analysis a correlation equation (a regression equation) between an SPAD conversion value (X) calculated from color information and an SPAD value (Y) obtained by measuring the leaf by a chlorophyll meter is represented by 0.8762X+4.6722. In FIG. 8, a vertical axis is the SPAD conversion value (X) which is calculated from the color information, and a horizontal axis is the SPAD value (Y) which is obtained by measuring the leaf by the chlorophyll meter. Plotted points correspond to the number of measured rice plants.

At this time, in a case where the SPAD value, which becomes a standard value of the color chip (a value approximately identical to a measurement value which is measured by the chlorophyll meter), is set to 40, and a calculation value of the SPAD conversion value from the color information is set to 34 at the time of performing calibration, the standard value−the calculation value=+6 is obtained, and the correlation equation is corrected to Y=08762X+4.6722+6. Accordingly, a regression line represented by the correlation equation is moved to the right. Furthermore, in FIG. 8, a determination coefficient R2 of 0.8762 represents a contribution rate in the correlation equation described above. That is, the determination coefficient R2 represents the degree of describing a fluctuation in a measurement result by an explanatory variable, and accuracy becomes high as being close to 1. In addition, FIG. 8 illustrates a correlative relationship between a case where the SPAD conversion value is obtained by being calculated and a case where the SPAD conversion value is measured by the chlorophyll meter and in actual calibration, as described above, Y=a(X1)+b(X2)+c, which is a correlation equation for obtaining the SPAD conversion value from the representative value of G and the representative value of Gray, is corrected to Y=a(X1)+b(X2)+c+α.

As described above, it is possible to obtain the converted leaf color value in a state of being calibrated from the average value of G and the average value of Gray by using the correlation equation in which the correction value is substituted into the correction term set in the regression equation.

In addition, in the calibration method described above, the user calibrates the camera 30, but alternatively, calibration which is performed by the manufacturer or the like of the camera 30 at the time of shipping the camera 30, will be described.

For example, the imaging element 41, which is a CMOS sensor, and the image processing circuit 51 as an integrated circuit are disposed in the camera 30. Furthermore, the imaging element 41 and the image processing circuit 51 may be configured in one chip as SOC, or may be configured of an individual chip.

For example, in the image processing circuit 51, white balance, black level control, various filter functions, matrix gain adjustment, aperture correction, gamma correction, and the like can be performed, or may be automatically adjusted, and for example, in the matrix gain adjustment, the aperture correction, the gamma correction, and the like, parameters are set in each RGB from the outside, and colors or luminance can be adjusted.

Here, using a blue LED and a yellow fluorescent body in the white LED 42 which is used for illumination, is comparatively inexpensive and becomes mainstream, and for example, in a case where a variation in performance such as luminance is comparatively large in the same rod, and the white LED 42 is used as a light source, there is a concern that the individual difference of the camera 30 increases.

Therefore, in the camera 30, the color chip (for example, an object for calibration of green, which becomes a leaf color value of 4 or a leaf color value in the vicinity of 4 (the plant information) included in a range of a proper leaf color of the leaf of the rice plant in a leaf color scale), which becomes a predetermined leaf color value, is imaged in a stage before shipping, and the parameter of the image processing circuit 51 described above is changed such that the leaf color value as a conversion value of a read value of the leaf color scale, for example, becomes 4 as described above. Accordingly, the individual difference decreases in a range where the individual difference can be adjusted by the image processing circuit 51 at the time of shipping the camera 30, and the calibration of the user described above can be omitted or a period until the calibration of the user is performed can be prolonged. In addition, the individual difference of the camera 30 decreases, and a variation in the converted leaf color value in each period of each farming family or each agricultural relationship, and thus, it is possible to increase the accuracy of the management using the converted leaf color value.

In the measurement of the converted leaf color value using the camera 30, the outside light is shielded, and predetermined illumination can be performed at any given time, and the measurement can be performed by the imaging element 41 having a small number of pixels without requiring the imaging element 41 having a large number of pixels. In addition, a part of arithmetic processing, data display, or the like can be performed by the smart phone 1 side. From the above description, it is possible to manufacture a measurement device which is more expensive than the leaf color scale but is less expensive than the chlorophyll meter including a dedicated colorimetric analyzing device but not a camera.

In addition, the outside light is cut, and the LED illumination is used, and thus, stable imaging can be performed, it is possible to prevent the measurement result from being changed according to the season, the time, the weather, or the environment, and to perform measurement with a small error. In addition, in a case where there is a correlative relationship between the colors of the surfaces of various portions of the leaf, the stem, the fruit, and the root of the plant (the crop) and various information items of the crop, various information items can be measured. At this time, insofar as having a function of outputting each of the values of RGB of each of the pixels of the image data obtained by imaging the surface of the plant (the crop) by the camera 30, and each of the values including Gray obtained from RGB, it is possible to measure the content of a substance other than chlorophyll by adding the relational equation which is registered in the app for plant information acquisition processing on the smart phone 1 side. For example, not only the SPAD value but also the chlorophyll amount is actually measured by actually crushing the leaf and by extracting the chlorophyll, and a correlation equation between the representative value described above and the concentration of the chlorophyll which is actually measured is obtained, and thus the chlorophyll amount may be obtained, but not the SPAD value. In addition, a nitrogen amount which has a correlative relationship with respect to the chlorophyll amount is actually measured, and a correlative relationship between the actually measured nitrogen amount and the representative value described above is obtained, and thus, the nitrogen amount may be measured. In addition, in the fruit or the like, in a case where a correlative relationship between the color and the concentration of sugar, acids, polyphenol, which is a pigment component, or the like contained in the fruit is confirmed, it is possible to use the camera 30 and the smart phone 1 for the measurement thereof.

Furthermore, in this embodiment, the representative value of S and the representative value of Gray are used, and thus, the representative value of R and the representative value of B may not be calculated. In a case where the SPAD conversion value is obtained from the regression equation, the SPAD conversion value, the region (the address), the date, the variety of the rice plant, and a plant length of the rice plant, which are input into the smart phone 1, are transmitted to the server 143 (the management server 10) through the Internet 142. Furthermore, for example, position information of the smart phone 1 read by the GPS provided in the smart phone may be used as the information of the region. In addition, a function of inputting the date may be a function of inputting the date of today from a clock function or a calendar function of the smart phone 1.

In addition, in this embodiment, the data processing circuit 52 is disposed in the camera 30, and a function of the data processing circuit 52 may be added to a function of the app for crop management of the smart phone 1. In this case, the camera 30 basically outputs each of the values of RGB and the value of Gray as the image data. Furthermore, depending on the height of the correlative relationship, all of RGB+Gray may be set as the independent variable, RG+Gray except for B may be set as the independent variable, or only G or Gray may be set as the independent variable.

Next, a second embodiment of the present invention will be described.

As illustrated in FIG. 9, a crop management system of this embodiment includes the smart phone (the smart phone 1) which is the user terminal used by the user, the management server 10 (the server 143) which uses a public wireless line for a portable telephone or a wired or wireless LAN and can be connected to the smart phone 1 through the Internet 2 (142), the camera 30 as the measurement device (the imaging device) which can be connected to the smart phone 1 through a USB or the like, and a terminal 60 for managing the management server 10, which includes a personal computer and can be connected to the management server 10 through the Internet 2 or the like.

The smart phone 1 as the portable terminal 130 is known, has a function of performing data communication, a display function including a display which displays display data such as an image (a static image and a moving image) and a text, as data to be subjected to communication, an input function of data such as a text, which is performed by mainly using a touch panel, and a program execution function of executing an application (an app), and functions as a terminal which is capable of performing input and output of the data with respect to the management server 10.

In addition, an agriculture worker is assumed as the user using the smart phone 1, and it is assumed that a person who performs agricultural works or the management of the agricultural works becomes the user of the smart phone 1. In addition, here, the cultivation of the rice plant is assumed as the agricultural works, and it is assumed that the agriculture worker is involved in rice production according to the cultivation of the rice plant. Furthermore, this embodiment relates to the management of the cultivation of the crop, and the cultivation of various grains, various vegetables including beans, potatoes, and the like, various fruits, and the like may be managed as the crop, in addition to the rice. In addition, the crop is not limited to the plant which becomes food insofar as the cultivation of the crop is basically managed, and the crop includes flowers, teas, trees, and the like. In addition, the present invention can be applied to color management of an ornamental plant such as a flower or a foliage plant.

The management server 10 is capable of simultaneously performing data communication with respect to a plurality of smart phones 1, which are the portable terminals 130, through the Internet 2, for example, includes a central processing unit (CPU), an RAM, an ROM, and the like, and includes a control unit 11 including various interfaces for data storage and data communication, a storage device formed of a hard disk or the like, and the like. In the storage device, a database which functions as a storage device storing various data items to be searched and is capable of extracting the stored data by searching or the like, is constructed.

In the management server 10 of this embodiment, a user information database 12, an agricultural land information database 13, a cultivation information database 14, a measurement value database 15, a leaf color standard value database 16, an agriculture and fertilizer database 17, and the like are constructed.

Individual information which is mainly input at the time of registering an account described below is registered in the user information database 12 in association with a unique user ID which is capable of specifying a user. For example, a user ID, a name, an address, an e-mail address, a telephone number, and the like are stored in the user information database 12, and a date of birth, a job, an organization (a group, a corporation, or the like) to which the user belongs, and the like are registered in the user information database 12. Furthermore, information of a credit card for charging or the like may be included in the user information database 12.

Furthermore, not only an individual person but also an organization such as a corporation and a group may be registered as the user.

The position of an agricultural, land (an agricultural field) in which the user performs agricultural works (the user performs management) is stored in the agricultural land information database 13 in association with the user ID described above. Furthermore, the position of the agricultural field is basically represented by the degree of latitude and the degree of longitude, and in a case where there is an address in the agricultural field, the address is also registered. Furthermore, a plurality of agricultural fields can be registered with respect to one user. In addition, the type of agricultural field and the area of the agricultural field are registered in the agricultural land information database 13.

The type of agricultural field is mainly separated according to a crop to be cultivated, and for example, includes a rice plant, a cabbage, a tomato, and the like. In addition, the type of crop which is registered as the type of agricultural field includes a variety name or a brand name which is capable of specifying the crop.

Furthermore, the position of the agricultural field, for example, may be input by using a GPS function of the smart phone 1, or may be input on a map app of the smart phone 1, and in a case where the degree of latitude and the degree of longitude of the agricultural field are known, the degree of latitude and the degree of longitude may be directly input. In addition, the degree of latitude and the degree of longitude of one spot representing the agricultural field may be input as the position of the agricultural field, and it is preferable to obtain a state where the shape and the area of the agricultural field are known, by inputting the degree of latitude and the degree of longitude of each corner of each agricultural field. Furthermore, for example, a quadrangular land includes four corners a triangular land includes three corners, and an approximately L-shaped land includes five external corners and one internal corner.

Thus, in a case where the degrees of latitude and the degrees of longitude of all corners (including the external corner and the internal corner) of the agricultural field are input, for example, an air photograph is displayed on the map app of the smart phone 1, each of the corners of the agricultural field is sequentially indicated on the air photograph, and thus, the degrees of latitude and the degrees of longitude of each of the corners are fixed and input. In addition, by using the GPS function of the smart phone 1, an operator of the smart phone 1, who is the user or the like possessing the smart phone 1, may register the degree of latitude and the degree of longitude measured in the corner of each of the agricultural fields by using the GPS function.

Here, in the GPS, there is a concern that an error occurs, and thus, it is preferable that the position of the agricultural field can be corrected on the map app. In the management server 10, the shape of the agricultural field and the area of the agricultural field are calculated on the basis of the position of the corner of the agricultural field. Furthermore, the area of the agricultural field may be input from the smart phone 1 by the user. In addition, a lot serial number which is capable of specifying the agricultural field in each lot, is applied to each of the agricultural fields, data such as the degree of latitude and the degree of longitude of each of the agricultural fields, data such as the type or the variety of crop, and a customer ID are stored in association with the lot serial number.

As described above, the position of the agricultural field in which the user performs the management or the agricultural works the variety of the crop to be cultivated in the agricultural field as the type of agricultural field, the area of the agricultural field, and the lot serial number are registered in the agricultural land information database 13 in association with the customer ID.

Cultivation information is stored in the cultivation information database 14 in association with the customer ID, corresponding to the variety of each crop, a lot serial number of art agricultural field in which each of the crops is cultivated, and a period (date and time). For example, the contents (including the amount of fertilizer or the amount of pesticide) of the agricultural works such as a day of sowing seeds, a day of planting, a day of having buds, a day of applying a fertilizer, a day of having ears (a heading day) an predicted heading day, a day of draining water from a rice-field, a day of applying a fertilizer, and a day of spreading a pesticide, the period of the agricultural works, and a day which becomes a turning point of the growth of the crop are stored as the cultivation information. Furthermore, the cultivation information stored in the cultivation information database 14 can be different according to the type of the variety of crop.

In this embodiment, the image data (the image information) obtained by performing imaging by the camera 30 described above and the data of the converted leaf color value (the crop information) read from the image data are stored in the measurement value database 15. Furthermore, in a case where the measurement value (the crop information) such as the plant length of the crop, the number of plants per unit area, the number of stems per a plant is included in addition to the converted leaf color value, data of all of the measurement values may be stored in the measurement value database 15. Furthermore, each information item is stored in the cultivation information database 14 and the measurement value database 15 in association with the customer ID described above, the lot serial number, and period information such as the date and time or the date, the user, the agricultural field, and the date and time can be specified from the crop information, the cultivation information or the agricultural land information can be searched from the customer ID or the lot serial number, and the region of the agricultural field can be searched. In addition, the converted leaf color value as the measurement value can be basically converted into the color scale value or the SPAD value in the case of reading a color scale, and in this embodiment, the converted leaf color value (the SPAD conversion value) is determined on the basis of the correlative relationship with respect to the SPAD value.

Furthermore, in this embodiment, a leaf color standard value which becomes a standard, is calculated on the basis of the converted leaf color value which is obtained by using the camera 30, and the converted leaf color value (the measurement value) and the leaf color standard value are obtained by the same method using the image data of the camera 30. Furthermore, the converted leaf color value or the leaf color standard value may be obtained by using image data obtained by performing imaging by an element other than the camera 30. Alternatively, the leaf color standard value may be set on the basis of the color scale value or the SPAD value as in the related art. In addition, in the following description, there is a case where the measured converted leaf color value is described as a measurement value, and the leaf color standard value is described as a standard value.

A preferred leaf color standard value which is associated with a period according to the variety of the crop and a cultivation region, is registered in the leaf color standard value database 16. Here, the period indicates that a time axis such as a date of the corresponding year or the number of days elapsed from a rice planting day. The standard value is set by analyzing the converted leaf color value which was measured by an expert in the past season of the corresponding variety in the corresponding region, and by determining the converted leaf color value to be a standard with respect to a specific time axis. The leaf color standard value of the leaf color standard value database 16 is determined in a tillering stage or a period before rice planting or the like, and is suitably changed by the expert according to the weather conditions or the like of the corresponding year.

In a case where the measured converted leaf color value is coincident with or close to the leaf color standard value, the leaf color standard value basically represents that the crop smoothly grows. For example, in a case where the converted leaf color value in a predetermined period is less than the leaf color standard value, it is indicated that the nitrogen fertilizer is insufficient, and in a case where the converted leaf color value is greater than the leaf color standard value, there is a possibility that overgrowth occurs due to an excessive nitrogen fertilizer, depending on the height of the rice plant, or the like. Furthermore, in a case where the height of the rice plant increases due to the overgrowth, a possibility that the rice plant falls down by the wind or the like increases, and thus, it is preferable to limit the cultivation of the rice plant to a certain degree, and for example, a nitrogen fertilizer amount is limited.

The leaf color standard value, for example, is calculated by analyzing all-year converted leaf color value data of the corresponding region in the season before the current season, not only the converted leaf color value data of the camera 30 but also leaf color value data based on the color scale or the SPAD value is considered, and data of a preferred converted leaf color value in each period of each variety is stored as the leaf color standard value. Furthermore, the period of the leaf color standard value may be shifted according to the conditions such as the weather of the current season, or an allowable range of the converted leaf color value with respect to the leaf color standard value may be widened or narrowed to a lower side or a higher side.

The amount of applied fertilizer per unit area is registered in the agriculture and fertilizer database 17 as management information for performing the fertilizer application management in the crop cultivation, in association with a difference between the measurement value of the converted leaf color value and the standard value with respect to the variety, the region, and the period. Furthermore, in a case where the measurement value is greater than the standard value, the amount of applied fertilizer basically becomes 0. Here, the fertilizer is mainly a nitrogen-based fertilizer, and for example, the amount of applied fertilizer, which becomes a standard of a phosphorus-based fertilizer, a potash-based fertilizer, or the like, or the amount of applied fertilizer according to the growth state may be registered. The amount of applied fertilizer per unit area is determined with respect to the difference described above between the measurement value of the leaf color and the standard value by the expert and is registered in the agriculture and fertilizer database 17. That is, information of the amount of applied fertilizer for performing the fertilizer application management is registered in the agriculture and fertilizer database 17 as one of management of the crop cultivation, and thus, a management information storage device storing management information relevant to the management of the crop cultivation is obtained. As with the leaf color standard value database 16, the agriculture and fertilizer database 17 is also suitably changed by the expert according to the weather conditions or the like of the corresponding year.

Here, the management server 10 adjusts the amount of applied fertilizer per unit area described above according to the converted leaf color value, the growth state such as the plant length, a cultivation density such as the number of plants per unit area or the number of stems in one plant, and the like. In addition, in the management server 10, the amount of applied fertilizer in each of the agricultural fields is calculated on the basis of the area of the agricultural field described above.

For example, on the basis of a difference of the measured converted leaf color value with respect to the leaf color standard value, the amount of applied fertilizer per unit area may be multiplied or divided by a coefficient such as 1.1 or 0.9, or the coefficient may be added to or subtracted from the amount of applied fertilizer per unit area, and in a case where the measured converted leaf color value is greater than the leaf color standard value and the plant length is higher than a plant length which becomes a standard, the amount of applied, fertilizer may be set to 0.

It is determined whether or not a growth density of the crop is higher than the standard on the basis of the number of plants per unit area, the number of stems in one plant, or the like, and on the basis thereof the amount of applied fertilizer per unit area may increase and decrease.

In addition, the terminal 60, for example, used by an operator of a group, who performs or supports the fertilizer application management or the fertilization management in an agriculture-related group such as a province autonomous community, an agricultural cooperative, and an agricultural corporation, is basically a terminal for performing data management such as data registration with respect to the leaf color standard value database 16 and the agriculture and fertilizer database 17, and data change, and is installed with a dedicated app B (the app for crop management) for browsing each of the databases of the management server 10. In the data registration of the leaf color standard value database 16 and the agriculture and fertilizer database 17, and the data change, there is a case where the data items are used by being subjected to statistical processing with reference to the agricultural land information database 13, the cultivation information database 14, and the measurement value database 15 or the like, and the terminal 60 logs in to the management server 10, and thus, is capable of accessing all of the databases of the management server 10. In addition, not data for each user but measurement data items or the like of a plurality of users using the crop management system is browsed by the terminal 60, and thus, it is possible to observe the conditions of the entire region or to compare measurement results of each of the users in each of the agricultural fields with each other. Therefore, it is possible to compare the measurement value of the leaf color not only with the standard value but also with the measurement value in the other agricultural field, and in a case where the measurement value is obviously greater than or less than the measurement value in the other agricultural field, the measurement value can be used in a determination material of the fertilizer application management.

Here, the camera 30 is for measuring the converted leaf color value, and is capable of imaging the surface of the leaf by interposing the leaf of the crop in a hatch kiss-like portion on a device upper portion, in a state where the outside light is shielded. The camera 30 is connected to the smart phone 1, outputs the image data obtained by performing imaging to the smart phone 1, and outputs the image data to the management server 10 or the like through the smart phone 1.

Furthermore, as with the plant information acquisition system of the first embodiment, in a crop management system of the second embodiment, the converted leaf color value is used as an index of a cultivation state of the crop (the plant). That is, in the crop management system, the converted leaf color value is acquired as the crop information on the basis of the image data obtained by imaging the surface of the crop by the camera 30. As with the first embodiment, in the second embodiment, the converted leaf color value representing the chlorophyll density is obtained for example, from the values of a plurality of variables configuring the color space of red, green, and blue (RGB) of the image data.

That is, the crop management system is approximate or similar to the plant information acquisition system, and substantially, is approximately the same system, and the camera 30 of the crop management system is identical to the camera 30 of the plant information acquisition system described above.

In addition, the smart phone 1 includes a flash memory as a storage storing an app, data which is used in the app, and the like. Furthermore, an RAM as a memory which is used in a program of the app or the like, for example, is provided in the control device.

In addition, the app for crop management is installed in the flash memory, and the converted leaf color value, which is an index of the chlorophyll amount, is calculated with respect to the representative values (the average values) of RGB and Gray described above, which are transmitted from the camera 30. Furthermore, the converted leaf color value is calculated from the image data obtained by performing imaging by the camera 30, and processing of calculating the converted leaf color value may be performed by the smart phone 1, may be performed in the management server 10 to which the image data is transmitted from the smart phone 1, or may be performed in the camera 30. Furthermore, in the following description, the converted leaf color value be described, and here, a color scale conversion value can be converted into the SPAD conversion value, and as described in examples described below, the SPAD conversion value is obtained, and the obtained SPAD conversion value is converted into the color scale value.

A dedicated app A (the app for crop management) is downloaded and installed in the smart phone 1 from the management server 10. For example, the (multiple) regression equation (the correlation equation) between the representative value described above and the converted leaf color value (the SPAD conversion value), which is obtained by regression analysis or multiple regression analysis, is registered in the app for crop management. For example, the multiple regression equation calculating the SPAD conversion value from the average value of G in each of the average values of RGB and the average value of Gray is registered. Accordingly, in a case where each of the average values of RGB and the average value of Gray are received from the camera 30, the converted leaf color value is output from the smart phone 1 on the basis of the average value of G and the average value of Gray.

In addition, the obtained converted leaf color value, the variety of the rice plant, which is input into the smart phone 1, the region (the address) in which the rice plant is cultivated, the current date, and the height of the rice plant (the plant length) are transmitted to the management server 10 as data for performing the fertilizer application management. In the management server 10, for example, the leaf color standard value, which becomes a standard, is registered in the leaf color standard value database 16 described above in association with the variety of the rice plant, the region (the address), and the period (the date).

In the management server 10, as processing of the fertilizer application management, the leaf color standard value database 16 is searched, and the leaf color standard value is extracted, from the region (the address of the agricultural field, or the degree of latitude and the degree of Longitude), the current date, and the variety of the rice plant, which are input from the smart phone 1. Next, the extracted leaf color standard value is compared with the input converted leaf color value.

Here, in a case where the leaf color standard value which is registered in the leaf color standard value database 16 in association with the variety, the region, and the period (the date) and is extracted as described above, is compared with the measured converted leaf color value, for example, in a case where the converted leaf color value is less than the leaf color standard value (in a case where the color is pale), it is considered that a nitrogen source is insufficient, whereas in a case where the converted leaf color value is greater than the leaf color standard value (in a case where the color is dense), it is considered that the nitrogen source is excessive.

Accordingly, it is possible to transmit guidance on the fertilizer application management such as whether or not the nitrogen fertilizer is applied, to the smart phone 1 from the management server 10.

A crop information acquisition method of acquiring the converted leaf color value as the crop information of the camera 30 of the crop management system of the second embodiment is performed, for example, as with the plant information acquisition method of the plant information acquisition system of the first embodiment. That is, the crop information acquisition method is performed as with the plant information acquisition processing illustrated in the flowchart of FIG. 4 described above.

Next, main processing, login processing, and initial setting processing in the app for crop management of the smart phone 1 will be described with reference to flowcharts of FIG. 10, FIG. 11, and FIG. 12. Furthermore, here, for the sake of easy description, cultivation management such as the fertilizer application management or the fertilization management of the rice plant as the crop is performed as the app for crop management, but the crop is not limited to the rice plant, and the crop management system can be applied to various vegetables, fruits, various crops such as grains as the crop.

FIG. 10 is a flowchart and a main screen illustrating the main processing of the crop management app. In a case where the app for crop management is activated by the smart phone 1, the main processing starts, and a main screen 1*a* is displayed (step A1). Here, the login processing, the initial setting processing, and crop management processing are basically performed in the app for crop management. In addition, the crop management processing includes three modes, and the user is able to select any one mode by the smart phone 1. The mode of the crop management processing includes a measurement determination mode in which the converted leaf color value is measured and the growth state of the crop representing the measured converted leaf color value is determined, a cultivation information input mode in which the user inputs information of the agricultural works such as planting, spreading of the pesticide, and the fertilizer application, and a leaf color value history display mode in which the history of the measurement result of the measured converted leaf color value is compared with the leaf color standard value and is displayed.

As illustrated in FIG. 10, an initial setting button 1*b*, a measurement determination button 1*c* as a button corresponding to each of the modes of the crop management processing described above, a cultivation information input button 1*d*, and a leaf color value history display button 1*c* are displayed on the main screen (an activation screen) 1*a* at the time of being activated. In addition, a login button 1*f* is displayed on the main screen 1*a*, and in a case where the login button 1*f* is touched, and login is not performed, the login processing starts, and basically, in a state where the login is not performed, the login processing starts by touching any button.

That is, in the smart phone 1, the crop management app is activated, and then, it is determined whether or not the login is performed by using a touch operation with respect to the main screen 1*a* as an opportunity (step A2). Furthermore, a state where the login is performed, is a state where authentication is performed in the management server 10 according to the input of account information from the smart phone 1 where the crop management app is activated, and the access of the smart phone 1 to the management server 10 is allowed.

In a case where the login is not performed, the login processing described below starts (step A3). In a case where the login is already performed, and the login processing described above ends, an operation (processing) corresponding to each of the buttons 1*b* to 1*e* on the main screen is selected by using a touch operation with respect to each of the buttons 1*b* to 1*e* on the main screen 1*a* other than the login button 1*f* as an opportunity (step A4), and corresponding to the touched buttons 1*b* to 1*e*, the initial setting processing is selected and executed (step A5), the measurement determination mode of the crop management processing is selected and executed (step A6), the cultivation information input mode of the crop management processing is selected and executed (step A7), or the leaf color value history display mode of the crop management processing is selected and executed (step A8).

Next, the login processing will be described with reference to the flowchart of FIG. 11.

As described above, when the app for crop management is activated, in a case where the login is not performed, the login processing starts, and a login screen is displayed on the screen 1*a* of the smart phone 1 (step B1). For example, the user ID and an input box of a password are displayed on the login screen, the user ID and the password are input, and then, the login button for performing the login is displayed. In addition, a registration button is displayed on the login screen wits respect to an unregistered user to whom the user ID and the password are not set.

In a case where the registration button is pressed on the login screen, the user registration processing starts, and in the app for crop management, it is determined whether or not user registration is performed according to whether the registration button is pressed or the login button is pressed (step B2).

That is, in a case where the registration button is touched, the user registration processing is performed by considering that the user registration is selected, and in a case where the login button is pressed, the login processing is performed.

In a case where the registration button is touched, the user registration processing is performed (step B3). In the user registration processing, user information of each user, which is registered in the user information database 12 of the management server 10, is input. Basically, an input box of each item of the user information is displayed, and the user inputs the user information corresponding to each input box. Furthermore, in the user registration processing, the user information is transmitted to the management server 10 from the smart phone 1, and the user information is registered in the user information database 12 of the management server 10, and thus, a state is required to be obtained in which the data communication is performed between the smart phone 1 and the management server 10 at the time of registering the user information.

The user information which is input by the user registration processing and is registered in the user information database 12, for example, includes a customer ID, a user ID, a password, a name, an address, an e-mail address, a telephone number, charging information, a contract period, a camera serial number, an affiliated group, and the like.

In the user information registration processing, the registration of the user information is notified to the management server 10 from the smart phone 1, and at this time, the management server 10 performs processing of automatically setting a customer ID which is not registered in the user information database 12, and then, registers the user information input by the smart phone 1 in the management server 10 in association with the customer ID.

The user ID is an ID which is set by the user, and for example, may be a nickname, an e-mail address, or a name, and it is preferable that the ID does not overlap with IDs of other users. Furthermore, the user ID is associated with the unique customer ID, and thus, may overlap with the IDs of the other users.

The charging information, for example, is information of a credit card, and charging may be performed by a prepaid card, an electronic money card, bank transfer, automatic withdrawal, and the like. In addition, in the use of the crop management system, the user may not be necessarily charged.

The contract period is a use period of the user on the contract of the crop management system, and for example, the contract period is automatically updated. The camera serial number is a number which is uniquely set in each of the cameras 30 connected to the smart phone 1 described above, and it is possible to determine whether or not the camera 30 is a regular product according to the camera serial number. In this example, the camera 30 for the crop management system is set, the set camera 30 is purchased and used by the user, or the camera 30 is provided from an affiliated group, and a serial number is applied to each of the cameras 30, and thus, it is possible to determine (authenticate) whether or not the camera 30 can be used in the crop management system according to the serial number. Furthermore, the camera 30 which can be used is limited, and thus, it is possible to suppress a variation in the measurement result of the converted leaf color value, and to improve the reliability of the measurement result.

Furthermore, in a case where the serial number is not input, the crop management system may not be used by considering that the camera 30 connected to the smart phone 1 is not capable of being used. For example, the purchase of the camera 30 may be one of the use conditions of the crop management system.

The affiliated group, for example, includes an agricultural cooperative, an agricultural corporation, and the like.

According to the affiliated group, a service that guidance is received from the terminal 60 managed by the affiliated group, can be performed with respect to a user belonging to the group.

In a case where the user information is input into each of the input boxes of the user information, the user registration is completed, and the user registration processing ends. Furthermore, when the user registration ends, a state is obtained in which the login is performed.

In a case where the login button is pressed, the user registration processing is not performed, and the login input processing is performed (step B4). In the login input processing, the user ID and the password input into the input box described above are transmitted to the management server 10, and authentication processing using the user information database 12 is performed in the management server 10. In the management server 10, as described above, the password is extracted from the user information database 12 on the basis of the user ID and the customer ID input from the smart phone 1, and in a case where the extracted password and the input password are coincident with each other, the login is permitted, and in a case where the extracted password and the input password are not coincident with each other, the login is rejected.

In the smart phone 1 where the login input processing ends, the authentication processing starts (step B5), and in a case where the result of the permission or the rejection of the login described above is transmitted from the management server 10, the result is displayed. Furthermore, when the login is permitted, the smart phone 1 is in a state of being logged in the management server 10, and selects a menu set in the management server 10, and thus, each processing is performed. In a case where the login is rejected, the user inputs again the user ID and the password as an account, or ends the app for crop management.

Next, in the main screen (the activation screen) 1*a* at the time of being activated, processing when the initial setting button 1*b* is selected, will be described. When the smart phone 1 is logged in the management server 10, the smart phone 1 urges the initial setting processing in a case where initial setting is not yet completed. Furthermore, whether or not the initial setting is completed is registered in the user information database 12 in association with the customer ID, and is confirmed at the time of being logged in the management server 10. Furthermore, in a case where an agricultural land corresponding to the customer ID is not registered in the agricultural land information database 13, agricultural field registration of the initial setting processing is not performed, and thus, it is possible to confirm whether or not the initial setting processing is performed.

In the initial setting processing, the position of the agricultural field is basically registered in which the user performs the agricultural works. Furthermore, when the fertilizer application management is performed in the crop management system, data or the like of the area of the agricultural field in the agricultural land information is required, and for example, in a case where the growth state of the crop such as a rice plant is determined from the converted leaf color value or the like, and the fertilizer application management is performed by a unique method, information of each agricultural field is not necessarily required to be input as the agricultural land information. Furthermore, the agricultural land information may be input from a setting screen at any given time.

As illustrated in flowchart of FIG. 12, in the initial setting processing of the smart phone 1, an initial setting screen is displayed on the display (step C1). A selection screen of whether or not the agricultural field registration is performed is displayed on the initial setting screen, and whether or not the agricultural field registration is performed can be input by the user on the selection screen. In the smart phone 1, it is determined whether or not the agricultural field registration is performed on the basis of the input of the user (step C2). In a case where it is selected that the agricultural field registration is not performed, the initial setting processing ends. In contrast, in a case where it is selected that the agricultural field registration is performed, an input box of the agricultural land information is displayed, and the information of the agricultural field described above can be input by the user as each agricultural land information item. Furthermore, each of the users is able to register a plurality of agricultural fields. In a case where each of the agricultural land information items is input into the input box of the agricultural land information, the smart phone 1 transmits the input agricultural land information to the management server 10 as agricultural field registration processing (step C3). The transmitted agricultural land information is registered in the agricultural land information database 13 of the management server 10 in association with the customer ID (the user ID). Furthermore, in the agricultural land information database 13, the agricultural field is registered in each of the lots as the unit of the agricultural field.

The information of the agricultural field as the agricultural land information input in the initial setting processing includes a lot serial number in each agricultural field (in each lot), an agricultural field name, an address, a region name, the area of the agricultural field, the number of vertices (corners) of the shape of the agricultural field, the degree of latitude and the degree of longitude of each of the vertices, and an owner name. In a case where the user has a plurality of agricultural fields, the agricultural field name is for easily distinguishing each of the agricultural fields, and is arbitrarily set. Furthermore, the agricultural field name may be automatically set by a combination between the user ID or the like and a sequence number, an alphabet, and the like. The lot serial numbers of each of the agricultural fields are unique numerical values which do not overlap with each other in the agricultural land information database 13, and the lot serial numbers, for example, are set in the management server 10 not to overlap with each other, with reference to the agricultural land information database 13.

The area of the agricultural field may be input by the user, and the shape and the size of the agricultural field are determined by inputting the position of each of the vertices described above, and thus, the area of the agricultural field may be calculated from the shape and the size of the agricultural field. The region name is basically a name which becomes the municipal of the address, and for example, in a case where the region name is used as a brand of rice, a name which becomes the brand may be used.

In the input of the degree of latitude and the degree of longitude as the position of the vertex of the shape of the agricultural field, for example, the current location obtained by the GPS of the smart phone 1 may be used.

For example, the number of vertices is input, and then, the user is positioned in each of the vertices with the smart phone 1 and presses a predetermined button on the initial setting screen of the smart phone 1, and thus, inputs the current position which is measured by the GPS of the smart phone 1. In addition, a map app is used, and a vertex position on a map is touched, and thus, the vertex position may be input. In this case, not only the map but also an air photograph may be used as the display of the smart phone 1.

In the input of the current location performed by using only the GPS, there is a concern that an error occurs, and thus, the position of the vertex of each of the agricultural fields is input by the GPS, and then, the input position of the vertex on the map of the map app is displayed, and thus, the position may be corrected on the map. Furthermore, in a case where the area of the agricultural field is input in advance by the user, and the area is not calculated from the shape represented by the vertex position of the agricultural field, there is no problem even in a case where there are some errors in the vertex position, and thus, the position on the GPS may be used without being corrected.

In a case where the input of information of one agricultural field ends, subsequently, a measurement point of the agricultural field is input by the user, and the input measurement point information is registered in a measurement point D/B (step C4). The measurement point can be input by the same method as an input method of the position of the vertex of the shape of the agricultural field described above. In the measurement of the SPAD conversion value, fixed-point observation is required, and thus, the measurement point is registered in advance. A measurement point NO is applied to the measurement point in the input order.

In a case where the input of the information of one agricultural field ends, a screen for performing selection of whether or not information of the next agricultural field is input is displayed on the initial setting screen, and thus, the user selects whether or not information of another agricultural field is further input.

In the smart phone 1, subsequently, it is determined whether or not the information of the next agricultural field is input (step C5), and in a case where the information of the next agricultural field is not input, the initial setting processing ends, and in a case where the information of the next agricultural field is input, the process returns to a state where the information of the agricultural field before step C3 is input, and the information of the next agricultural field is input.

In the crop management system, the user periodically measures the converted leaf color value in a state where the initial setting ends, it is determined whether or not the measured converted leaf color value is greater than the leaf color standard value, and the measurement value such as the variety of the crop (the rice plant), the growth rate of the crop, and the cultivation density of the crop is input to the measurement value database 15 of the management server 10 from the smart phone 1 as the cultivation information in addition to data of the converted leaf color value. In addition, in a case where the agricultural works such as applying of the fertilizer and the spreading of the pesticide are performed, the agricultural works are registered in the cultivation information database 14 as the cultivation information.

The cultivation information is input in the cultivation information input mode of the crop management processing. In the input of the cultivation information, the information of the agricultural field is required, and can be used after the initial setting processing. In the main screen 1*a* described above, the cultivation information input button 1*d* is touched, and thus, the cultivation information input mode of the crop management processing starts.

Next, in the main screen (the activation screen) 1*a* at the time of being activated, processing when the cultivation information input mode button 1*d* is selected will be described. As illustrated in a flowchart of FIG. 13, in the cultivation information input processing, data specifying the agricultural field is input, and for example, an input box of the agricultural field name is on a cultivation information input screen of the smart phone 1 is displayed (step D1), and the user inputs the agricultural field name, and thus, the agricultural field name is transmitted to the management server 10 from the smart phone 1 (step D2). Furthermore, the smart phone 1 is logged in the management server 10 in advance, and thus, the agricultural field name that the user possesses, occupies, and handles, may be displayed on the screen such that the user may select the agricultural field name. In addition, at this time, data representing the current year-month-day is transmitted to the management server 10 from the smart phone 1. Furthermore, the data of the year-month-day may be data from which any one of the current year, Western calendar, and Japanese calendar is known, and may be obtained by a clock function of the management server 10 side.

In the cultivation information database 14, the cultivation information of each of the agricultural fields is registered for each lot of the agricultural field and for each year, as data of one record, and each record is associated with the customer ID, and the lot serial number of the agricultural field described above which is capable of specifying the agricultural field is associated with the year. Therefore, in a case where data representing the agricultural field name and the year is transmitted to the management server 10 from the smart phone 1 in which the login is performed, and the customer is recognized, in the management server 10, it is confirmed that the agricultural field corresponding to the agricultural field name is registered with reference to the agricultural land information database 13, and the cultivation information which is stored in the agricultural field of the cultivation information database 14 for each of the agricultural fields and for each of the years, as one record, is extracted from the customer ID, the lot serial number extracted from the agricultural land information database 13, and the current year.

Whether or not there is a record of the cultivation information corresponding to the customer ID, the lot serial number, and the year described above in the cultivation information database 14, is transmitted to the smart phone 1 from the management server 10. In the smart phone 1, the presence or absence of the record corresponding to the customer ID, the lot serial number, and the year described above, is determined according to the notification from the management server 10 (step D3).

In a case where there is no record of the cultivation information corresponding to the agricultural field and the current year, a new record is prepared and registered (step D4).

In this case, the preparation of the new record is requested from the smart phone 1, and in the management server 10, the new record is prepared in the cultivation information database 14.

When the new record is prepared, the customer ID is registered corresponding to the smart phone 1 in which the login is performed at the time of preparing the record and the cultivation information input processing is selected, the lot serial number on the agricultural land information database 13 is registered on the basis of the agricultural field name described above, and the current year is registered, in the new record. In general, the new record is prepared at the start of a year, and at this time, for example, the variety of the rice is input as information which is determined in advance. From this point forward, the cultivation information can be searched in the cultivation information database according to the customer ID, the lot serial number, and the year which are registered at the time of preparing the new record, and uninput cultivation information can be input in a suitable period.

In a case where there is a record of the cultivation information corresponding to the information of the customer ID, the lot serial number, and the year described above, in the management server 10, a record of the corresponding cultivation information is extracted from the cultivation information database 14, and the record is transmitted to the smart phone 1 (step D5).

In a case where the new record of the cultivation information is registered and in a case where the record of the cultivation information is extracted, the smart phone 1 is in a state where the record is received, and checks whether or not the data is input into each basic item into which data is input in the cultivation information of the record (step D6). Furthermore, the item to be input is a basic item described below which is set in advance. In addition, the check may be performed in the management server 10 but not in the smart phone 1. For example, in a case where the new record is prepared first, information such as the variety of the rice and the number of plants per lot area is required as an input item. After that, a message of urging the input of the item to which input is required is output on the screen according to the period.

The basic item of the data to be input in the cultivation information database 14 includes the variety of the rice, the number of plants per lot area, a planting day, prediction of a heading day, a harvesting day, a yield (Kg), a yield per unit area (Kg/m2), a grade, an average water amount (%), and an average protein amount (%). The variety of the rice, for example, is a variety such as Koshihikari and Akitakomachi. Furthermore, here, as described above, the crop is the rice, and in a case where the crop is other than the rice, the variety of the crop is registered.

The number of plants per lot area, for example, corresponds to the number of plant bundles per unit area planted bundle by bundle at the time of performing planting. One plant includes a plurality of stems of a rice plant, the number of stems per one plant sequentially increases from the stage of seeding. The planting day is a day of planting rice, and in the management of the agricultural works in the crop management system, it is preferable that the cultivation information is input before and after the planting day, and the cultivation of the rice plant is managed.

The predicted heading day is a day on which the heading of the rice plant is predicted, and is determined on the basis of the region and the planting day. Basically, the heading day is predicted in an autonomous community or an agricultural cooperative of the region, and thus, can be known to an agriculture worker of each region. Furthermore, in the management server 10, the predicted heading day may be automatically input according to the region and the planting day.

The harvesting day is registered after the day on which harvesting is actually performed, and thus, is the item of data to be input, but is not input during the actual cultivation. Furthermore, the data of the harvesting day remains as the data of the year before the current year of the cultivation information, and can be used in the cultivation after the following year as past information. In addition, in the cultivation information database 14, data fixed after the harvest is input, and data such as the yield (Kg), the yield per unit area (Kg/m2), the grade, the average water amount (%), and the average protein amount (%) is input after an examination which is performed after the harvest.

The performed agricultural works are stored in the cultivation information database 14, in addition to information of the basic item described above, and for example, an implementation item code representing the fertilizer which is applied in association to a day of applying the fertilizer or a day of spreading the pesticide, and an implementation item code representing an applied amount or the pesticide, and a spread amount can be input. In the cultivation information database 14, codes are set in each of various fertilizers and various pesticides, as implementation items of the agricultural works, and it is possible to specify the fertilizer or the pesticide by the code of the implementation item. Furthermore, the agricultural works are not limited to the fertilizer or the pesticide, but are capable of including various agricultural works insofar as the codes of the agricultural works are set. All agricultural works which can be actually performed, such as the access of water with respect to the rice-field, the amount of water at the time of performing irrigation with respect to a crop other than the rice, weeding, and bagging of fruits, can be registered as the agricultural works.

In the smart phone 1, it is determined whether or not there is an item to be input according to the check of the item to be input described above (step D7). Furthermore, as described above, in a case where the check is performed in the management server 10, the check result is also determined in the management server 10.

In a case where the cultivation information is an uninput item in the basic items to be input, an input screen of the basic item is displayed on the smart phone 1, the cultivation information can be input into the uninput item (step D8). Basically, the harvesting day is not input during the cultivation, an input screen of the basic item is displayed until the harvest is performed, and the input screen of the basic item can be skipped. In addition, in a case where the record of the cultivation information in each of the agricultural fields is newly registered, there is an uninput basic item, and thus, the basic item of the cultivation information is input.

In a case where the basic item is input, in a case where the input of the basic item is skipped, and in a case where there is no basic item to be input, the cultivation information in-out screen for inputting the items of the agricultural works described above is displayed on the smart phone 1 (step D9). In the smart phone 1, the information of the agricultural works can be input, and an implemented date, the code of the implementation item, and a numerical value relevant to the implemented contents (for example, the amount of fertilizer, pesticide, water, or the like) can be input into an input box of the agricultural works (step D10).

Furthermore, in the input of the cultivation information, an input box of each of the cultivation information items is displayed on the cultivation information input screen of the smart phone 1, and the cultivation information such as the code of the implementation item described above is input by the user. In a case where the cultivation information is input into the input box, the input cultivation information is transmitted to the management server 10 from the smart phone 1, and the cultivation information is input into the cultivation information database 14 of the management server 10 (step D11).

Next, in the main screen (the activation screen) 1*a* at the time of being activated, processing when the measurement determination mode button 1*c* is selected will be described with reference to a flowchart of FIG. 14. In this embodiment, the converted leaf color value of the leaf the plant length of the crop, and the number of stems in one plant are measured as an index measuring the growth state of the crop. The plant length of the crop represents the growth state of the crop, and for example, in the case of harvesting not a leaf or a stem but a fruit as a grain, as with the rice, the plant length is not proportionate to a harvest amount. In particular, in the rice plant, in a case where the plant length is excessively high, a probability that the rice plant falls down increases, and thus, adversely affects the harvest amount or the quality of the fruit.

The leaf color value basically depends on the chlorophyll density, and the chlorophyll density depends on the nitrogen amount. That is, in a case where the nitrogen amount as the fertilizer is sufficient, the leaf color value becomes a large value, and in a case where the nitrogen amount is insufficient, the leaf color value becomes a small value. In the leaf color value, even in a case where the density is denser than a state representing a sufficient density, the density does not favorably affect the harvest amount of the rice, or the like, and basically, it is preferable that the leaf color value, that is, the density of green becomes an appropriate density. The leaf color standard value corresponding to each variety and each period, for example, represents a leaf color value which is preferable for harvesting a large amount of high-quality rice. The number of stems in one plant increases after the planting as described above, a requisite amount of the fertilizer or the like increases according to an increase in the number of stems.

In a case where the measurement determination button is displayed on the main screen 1*a* of the smart phone 1 is pressed as described above, the measurement determination mode of the crop management processing starts. Even though it is not illustrated, the user selects the agricultural field first. The agricultural field is determined by displaying an agricultural field list screen of the user on the screen, and by allowing the user to touch the agricultural field list screen and to select the agricultural field. The agricultural field is selected, and thus, an agricultural land information D/B and the measurement point D/B on the server are searched, the information of the agricultural field and information of the measurement point are acquired, the shape of the selected agricultural field is displayed on the screen, and the position of the measurement point is displayed thereon. Measurement determination processing of the subsequent crop management processing is performed by the number of measurement points of the selected agricultural field. In a case where the user selects the measurement point first by touching the measurement point, in the smart phone 1, an input box of the plant length of the rice plant and an input box of the number of stems per one plant are displayed before the converted leaf color value is measured. Accordingly, in a case where the user inputs the plant length of the rice plant and the number of stems per one plant on the smart phone 1, the plant length and the number of stems are stored in the smart phone 1 (step E1).

Next, the leaf of the rice plant is imaged by the camera 30 connected to the smart phone 1, and thus, the image data of the leaf is input into the smart phone 1 from the camera 30 (step E2). At this time, the leaf is imaged by the illumination light of the LED in a state where the outside light is shielded. Accordingly, the influence of the outside light can be suppressed, direct reflection light from the surface of the leaf is suppressed by the polarizing plate in the imaging using the LED illumination, and the reflection light with respect to the LED illumination from a close position is prevented from being imaged as white. A map representing the current location and the measurement point may be displayed on the smart phone such that imaging can be performed at the designated measurement point, before imaging is performed, and the user may be guided to an accurate position. Alternatively, voice guidance such as "move slightly to the front by ○ m" and "move diagonally to the front by ○m" is performed.

In the smart phone 1, the degree of latitude and the degree of longitude of the current position are read from the internal GPS function, corresponding to the input of the imaging data, the current time (including the year, the month, and the day) is read by the internal clock function, and the position and the date and time are stored in association with the image data (step E3). Furthermore, a case where the degree of latitude and the degree of longitude of the read current position is separated from the measurement point which is currently selected, by greater than or equal to 1 m, is considered as an input error, and thus, an error message is output. Alternatively, in a case where it is determined that the degree of latitude and the degree of longitude of the read current position is separated from any measurement point which is registered in the agricultural field, by less than 1 m, it is considered that there is an input error of the measurement point, and the following processing may be performed by using the input measurement point as the closest measurement point.

In addition, the smart phone 1 accesses a site which outputs weather information, and reads the current weather of a region including the current location which is read by the GPS described above or in the vicinity of the current location (step E4). Next image analysis for calculating the converted leaf color value from the image data is performed (step E5). Basically, as described above, the representative values of each of the values of R, G, B, and Gray are obtained from the image data. Furthermore, the processing, for example, may be performed in the camera 30, or may be performed in the smart phone 1.

Next, the obtained values of R, G, B, and Gray and the converted leaf color value are calculated by using the correlation equation described above (step E6). Here, the converted leaf color value is obtained from the correlation with respect to the SPAD value, and is a value which is approximate to the SPAD value. The converted leaf color value (the SPAD conversion value) can be used as the SPAD value, and can also be converted into the color scale conversion value which is assumed by the color scale. Basically, in data which is provided by a province autonomous community, an agricultural cooperative, or the like, the color scale value and the SPAD value are used, and determination using the provided data can be performed by using the converted leaf color value (the color scale conversion value and the SPAD conversion value) obtained from the image data.

In a case where measurement at one measurement point of the converted leaf color value ends, as illustrated in FIG. 15, the measurement result is displayed on a screen 5*b*(1) (a measurement display mode screen) of the smart phone 1. Furthermore, the switch 35 of the hotchkiss-like camera 30 interposing the leaf is turned on, and thus, imaging is automatically performed. At this time, in the smart phone 1 to which the camera 30 is connected, a shutter sound is output, and vibration (for 1 second) occurs.

A display 5*c* of the image data obtained by performing imaging is performed on the screen 5*b*(1). The display 5*c* represents the surface of the leaf, and for example, a green color image indicating the converted leaf color value. In addition. A display 5*d* of the values of R, G, B, and gray (Gray) as the average value (the representative value) of the color of the image data, a display 5*e* of the SPAD conversion value calculated from the values described above, and a display 5*f* of the color scale conversion value converted from the SPAD conversion value are performed on the screen 5*b*(1). In addition, measurement is performed at one measurement point by the set number of times, the average of the SPAD conversion values and the color scale conversion values of each measurement point is obtained, and the display 5*g* is performed by the number of times of imaging which is the remainder obtained by dividing the number of times of imaging by the set number of times for performing imaging. In addition, a shutter button 1*b* is displayed on the screen 5*b*(1), the switch 35 interposing the leaf is not turned on, the shutter button 1*h* on the screen 5*b*(1) is touched by a finger, and thus, imaging can be performed. Accordingly, the surface of root vegetables or fruits as a crop can also be imaged, in addition to a thin such as a leaf.

As illustrated in FIG. 16, in a case where the set number of times of imaging ends at one measurement point, a measurement result display 1*i* is performed on the smart phone 1. In the display, the SPAD conversion value and the color scale conversion value are displayed as the measurement value of each measurement of the set number of times of measurement, and the average value thereof is measured. Furthermore, in a case where there is an abnormal value in the measurement value before being averaged, measurement can be performed again, and for example, in a case where one measurement value is touched, and change on the screen is touched, imaging can be performed again. In a case where there is no problem, registration is touched, and thus, data such as the measurement value and the average value is transmitted to the management server 10 and is stored. Furthermore, a point which is found by a measurer at the time of performing measurement, can be described as a comment, and the comment is also stored at the time of registering the data.

Next, data of the position and the month and day input as described above is transmitted to the management server 10. In the management server 10, the leaf color standard value is extracted from the leaf color standard value database 16 on the basis of the variety of the rice plant, the position, and the month and day, and is transmitted to the smart phone 1. In the smart phone 1, the leaf color standard value can be obtained (step E7).

Furthermore, in this step E7, when the camera is connected to the smart phone in a wired manner or a wireless manner, the serial number of the camera stored in the memory in the camera may be acquired and may be transmitted simultaneously at the time of transmitting the data described above to the server, and in the server, in a case where the received serial number of the camera and the camera serial number stored in a user information D/B are compared with each other and are not coincident with each other, a response may be transmitted to the smart phone as an inappropriate access request, and in the smart phone, the error message may be output, and the subsequent processing may not be performed. Accordingly, it is possible to prevent an inappropriate access, and an image and an SPAD conversion value of an inappropriate camera from being registered in the server, and to properly determine a leaf color standard value of the next year.

As illustrated in a graph of FIG. 14, the leaf color standard value, which is a standard leaf color value, is registered in the leaf color standard value database 16 in association with the variety and the date, and the variety and the date are input, and thus, it is possible to extract the leaf color standard value. In the smart phone 1, the converted leaf color value which is obtained from the image data by measurement is compared with the leaf color standard value which is obtained from the leaf color standard value database (step E8). Furthermore, here, the color is dense as the leaf color value increases.

The comparison result includes a case where the measurement value is approximately identical to the standard value, and the measurement value is in an allowable range with respect to the standard value (step E9). A case where the measurement value is greater than the standard value over the allowable range (step E10), and a case where the measurement value is less than the standard value over the allowable range (step E11).

In a case where the standard value and the measurement value are in the allowable range, the converted leaf color value of the rice plant which is cultivated is approximately identical to the leaf color standard value, and thus, the rice plant smoothly grows, and for example, a display representing that the rice plant smoothly grows is performed in the smart phone 1 (step E9). In a case where the measurement value is greater than the standard value over the allowable range, that is, in a case where the color is dense, a possibility that the nitrogen fertilizer is excessive increases, and thus, a display of calling attention is performed in the smart phone 1 such that the fertilizer is avoided or the condition of the rice plant is observed (step E10). In a case where the measurement value is less than the standard value over the allowable range, it is considered that nitrogen is insufficient, and thus, it is preferable to apply the nitrogen fertilizer, and in order to determine the fertilizer amount, the agriculture and fertilizer database 17 of the management server 10 is searched by using the measurement value and the standard value (step E11). In this case, the variety of the rice plant, the region of the agricultural field, the planting day, the current date, and the like are input in addition to the measurement value of the converted leaf color value and the standard value. Table data of a difference between the standard value and the measurement value, the number of days elapsed from the planting day to the current, and the amount of applied fertilizer, with respect to each variety and each region, is stored in the agriculture and fertilizer database 17. In the table data, the amount of applied fertilizer is obtained from the difference between the standard value and the measurement value and the number of days elapsed from the planting day.

The amount of applied fertilizer is the weight of the set type of fertilizer per unit area of the agricultural field. The amount of applied fertilizer extracted from the agriculture and fertilizer database 17, for example, is multiplied by the area registered in the agricultural land information database 13. Accordingly, the amount of applied fertilizer per unit area and the amount of applied fertilizer per one agricultural field are calculated. In this case, the amount of applied fertilizer may be corrected on the basis of data such as the number of plants per unit area (lot) in the cultivation information database 14, the number of stems per a plant in the measurement value database 15, and the plant length. For example, standard values of the number of stems and the plant length are set corresponding to the month and day, a standard value of the number of plants is also set, and in a case where the number of stems and the number of plants are greater than the standard value, correction may be performed to increase the amount of applied fertilizer, and in a case where the plant length is long, correction may be performed to decrease the amount of applied fertilizer.

The amount of applied fertilizer per unit area and the amount of applied fertilizer per one agricultural field, which are determined, for example, are calculated in the management server 10, are transmitted to the smart phone 1 (step E12), and are displayed on the smart phone 1 (step E13). Furthermore, in a case where the fertilizer application is actually performed on the basis of the displayed data of the amount of applied fertilizer, the cultivation information input mode described above is selected, and the implementation of the fertilizer application is stored. When processing based on the comparison result between the measurement value and the standard value described above ends, the measured various values are registered in the measurement value database 15, with respect to each of the agricultural fields (with respect to each of the lot serial numbers) (step E14).

That is the customer ID, the lot serial number, the imaging date and time, the measurement spot (GPS), the weather, the temperature, the color image, the converted leaf color value (the converted measurement result), the standard value, the plant length value, the number of stems per one plant, the R value, the G value, the B value, the Gray (Y) value, the examination result, and the like are registered in the measurement value database 15.

The data stored in the measurement value database 15 can be basically browsed from the smart phone 1 of the user who is authenticated by the customer ID and the password, and can be browsed from the terminal 60 of a group operating the crop management system, for example, a province autonomous community, an agricultural cooperative, an agricultural corporation, and the like, and thus, the data can be used by the group. In this case, it is possible to compare data items of each of the agricultural fields of the plurality of users with each other.

A screen display which can be browsed from the smart phone 1 of the user will be described. Processing using the data of the measurement value database 15 includes the leaf color value history display mode of the crop management processing described above. As described above, in a case where the leaf color value history display button 1*c* is pressed on the main screen 1*a*, as illustrated in FIG. 17, a screen is displayed on which past data (the history) of the measurement value and past data (the history) of the standard value can be compared with each other.

In this case, it is possible to observe that both of the standard value and the measurement value fluctuate over time, and thus, for example, in a case where the amount of applied fertilizer increases in a state where the measurement value is less than the standard value, a case where the measurement value does not reach the standard value even after the amount of applied fertilizer increases, a case where the measurement value approximately reaches the standard value, a case where the measurement value exceeds the standard value, and the like can be observed, and an optimal amount of applied fertilizer with respect to a difference between the measurement value and the standard value can be obtained from the observation. Furthermore, in FIG. 17, the fertilizer application, a date of spreading the pesticide, and a use amount of the fertilizer or the pesticide, which are registered in the cultivation information database 14, are displayed. The display of the fertilizer application or the spreading of the pesticide is displayed on a time axis of a graph, corresponding to a date on which the fertilizer application or the spreading of the pesticide is performed. Accordingly, it is possible to easily confirm the influence of the fertilizer or the pesticide on the measurement value.

In addition, on this screen, the color of a background of a graph of FIG. 17 is displayed to be changed corresponding to a change in a difference between the measurement value of the converted leaf color value (the SPAD conversion value) and the standard value. That is, the background of the graph is divided into blocks in each predetermined period of the time axis, and the color of the background in each of the blocks is displayed as a color set in advance corresponding to the value of the difference between the measurement value and the standard value. Accordingly, it is possible to visually confirm the difference between the measurement value and the standard value. At this time, it is preferable that a color in a period in which measurement is not performed, is complemented, predicted, and colored from colors before and after a measurement day. At this time, the standard value is also displayed as a band on an upper portion or a lower portion of the graph, and is expressed as a gradation, and thus, it is possible to visually recognize the difference between the standard value and the measurement value according to a difference in the color.

In addition, in the agricultural field selected by the user, the outer shape of the agricultural field is displayed on the screen of the smart phone 1 by using data of the SPAD conversion value which is measured and calculated with respect to all of the measurement points and an image which is obtained by imaging the entire agricultural field from above with the camera function of the smart phone 1 by the user, the measurement value of the SPAD conversion value at each of the measurement points and the standard value are displayed, a SPAD conversion value distribution in the entire range of the agricultural field is predicted from the SPAD conversion value at each of the measurement points and a hue condition represented by the image obtained by imaging the agricultural field, and an image displayed by color-coding and painting the difference with respect to the standard value is illustrated in FIG. 18. Here, the agricultural field in the image imaged by the smart phone 1 is recognized. At this time, an imaging position of the agricultural field is determined by a position measurement function of the GPS or the like of the smart phone 1, the shape of the agricultural field is recognized as an image by a ridge, and the range of the agricultural field is recognized from a vertex position of the shape of the agricultural field described above. Furthermore, the user may input the range of the agricultural field on the image which is obtained by imaging the agricultural field, on the screen of the smart phone 1. In this case, for example, the range of the agricultural field is input by touching the vertex position of the shape described above on the image of the agricultural field.

Next, in the smart phone 1, the position of the measurement point at which measurement is performed as described above, is set on the image data. In this case, the degree of latitude and the degree of longitude of the measurement point described above are used. In the image data of the agricultural field, the agricultural field is partitioned into a plurality of areas according to a difference in the color on the image. At this time, for example, a value having high correlativity with respect to the SPAD value is used, among values relevant to each of the values of RGB of the image data, a color difference obtained from RGB, luminance, and the like. For example, the value of G or the value of Gray relevant to luminance obtained from the values of RGB may be used. In addition, a temporary SPAD conversion value may be used by being obtained from the values of RGB or the value of Gray of each of the pixels by the correlation equation described above.

For example, arbitrary method can be used as a method of partitioning the agricultural field into each of the areas by using the value (for example, the value of G) described above, the values of G on the image data at each of the measurement points are sorted and arranged in order of size of the value, a value intermediate between the adjacent values of G is used as a threshold value, the range of the value of G including the values of G at each of the measurement points is set as a range which is separated at each threshold value, and each of the pixels is partitioned into areas in each range on the basis of the value of G of each of the pixels of the image data.

Each of the partitioned areas is color-coded according to the size of the value of the difference between the measurement value at a measurement point to be included and the standard value. In addition, the SPAD conversion value distribution in the entire range of the agricultural field but not the difference with respect to the standard value may be painted and displayed. A mark such as a mark of × is displayed on a spot on the screen, where the measurement point is positioned, along with the measurement value of SPAD.

Next, a screen displayed on the terminal 60 of the group operating the crop management system, for example, a province autonomous community, an agricultural cooperative, an agricultural corporation, and the like, will be described. As described above, the terminal 60 is registered in the crop management server 10, and thus, for example, as illustrated in FIG. 19, the range of each of the agricultural fields registered in the crop management system on the map can also be displayed by color-coding a difference between the average value of the measurement values of all of the measurement points in the agricultural field and the standard value. In this case, it is possible to distinguish between an agricultural field which is similar to the standard value and an agricultural field which is greatly different from the standard value in approximately the same region, a message of calling attention can be transmitted to the smart phone 1 of the user of the agricultural field having a large difference between the standard value and the measurement value.

In addition, the difference between the standard value and the measurement value of each of the agricultural fields, a rice production amount or rice quality of each of the agricultural fields, and the like are compared with each other, and thus, the standard value can be close to a measurement value of an agricultural field where the rice production amount is large and the rice quality is high. Accordingly, it is possible to improve the standard value to a more suitable value. Furthermore, the color-coding of FIG. 17 to FIG. 19 represents a difference with respect to the standard leaf color value, and may be color-coding (color-coding directly expressing a leaf color or color-coding according to the converted leaf color value) representing the measurement value of the converted leaf color value (the SPAD conversion value).

Next, a third embodiment of the present invention will be described.

The third embodiment describes a method for detecting and deleting an abnormal value of the color information or the plant information in the plant information acquisition system of the first embodiment and the crop management system of the second embodiment.

For example, in a case where a skillful agriculture worker measures the SPAD value by a chlorophyll meter, there is a case where the measurement result is determined as abnormal from the feeling of the color obtained by visually perceiving the rice plant, and the SPAD value, which is the measurement result, and the measurement is performed again, and thus, a possibility that the influence of the abnormality on the crop management is excluded is high. However, it is not easy for an agriculture worker who is not skilled in measurement to pick out the abnormal value. Therefore, in the plant information acquisition system and the crop management system, the camera 30 or the smart phone 1 senses an abnormal value of color information or plant information to be measured.

In this embodiment, in a sensing method of an abnormal value corresponding to three causes for abnormality illustrated in FIG. 32, an abnormal value is determined in a case where any one of three abnormal value determination conditions is satisfied. In a case where an object is imaged in a predetermined range of the imaging range of the camera 30, a first abnormality determination condition determines a case where an imaging position is shifted, and a part of the predetermined range deviates from the object, or a case where the imaging position overlaps with a side edge portion of the object as abnormal. Here, the predetermined range, for example, is a range of approximately 180 pixels×180 pixels in 2 mm×2 mm. Therefore, for example, there is a case where the predetermined range is sufficiently less than the width of the leaf of the rice plant but the entire predetermined range does not overlap with the leaf depending on the way of imaging. In this case, a state is obtained in which any one of four corners of an image in the obtained rectangular predetermined range is shifted from the object, and thus, a corner portion deviating from the object of the image is darker (the color becomes denser) or brighter (the color becomes paler) than the other portions.

Therefore, in the first abnormal value determination condition, RGB values are acquired from pixels of four corner portions of the predetermined range, and a converted leaf color value of each of the corner portions is obtained. Here, in a case where a yellow conversion value is set to a conversion value of a read value of a leaf color scale, and the converted leaf color values of four corner portions are less than 1 or greater than 7, and color information in the entire predetermined range to be obtained by the measurement or the converted leaf color values are determined as the abnormal value.

That is, the abnormal value determination condition obtains each of the converted leaf color values of four corner portions in the rectangular predetermined range, and in a case where any one of the leaf color conversion values exceeds a predetermined upper limit value or a predetermined lower limit value, the converted leaf color value as the measurement result at the time of performing the measurement is determined as the abnormal value. In FIG. 32, in the image for describing the first abnormal value determination condition, the converted leaf color value of only one corner portion of four corner portions of 1 to 4 is greater than or equal to 9 over 7, and thus, the converted leaf color value in the entire predetermined range is determined as the abnormal value. Furthermore, one being used in abnormality determination is not limited to the converted leaf color value, and any one of the RGB values and the GRAY value (the average values) as the measurement result, which are used for obtaining the leaf color conversion value, may be independently used or a plurality of the values may be used by being combined, and may be determined by being compared with a single threshold value or a plurality of threshold values (the upper limit value and the lower limit value), which are set.

A second abnormal value determination condition mainly determines the abnormal value in a case where the outside light enters without being sufficiently shielded at the time of performing imaging. In this embodiment, the leaf is imaged in an interposed state by shielding the light, and the surface of the leaf is not a flat surface but a curved surface, and thus, the outside light enters without being sufficiently shielded, and there is a case of being brighter than a case of a normal image (the color becomes paler). The second abnormal value determination condition detects a case where the image (the color information) becomes brighter as abnormal. Furthermore, a state is obtained in which the outside light mainly enters from one side edge portion of the rectangular predetermined range described above, one side edge portion of a rectangular image mainly becomes brighter. As illustrated in items of the second abnormal value determination condition of FIG. 32, the converted leaf color value which is obtained in a case where a luminance value (the representative value) of blue B is greater than or equal to 75 (a range of 0 to 255) as the threshold value, is determined as abnormal. Furthermore, in a case where a green leaf is measured, in a state where the outside light is sufficiently shielded and a state where the outside light enters as illustrated in FIG. 32, a change in a luminance value of blue B is greater than that in other colors, the presence or absence of the outside light is easily grasped, and thus, the abnormal value is determined according to the luminance of blue B. Furthermore, an average luminance value of each color and a luminance value in the case of being determined as abnormal are illustrated in FIG. 32, and thus, a change amount of the luminance of blue B is obviously greater than change amounts of the luminance of the other colors.

Furthermore, as the abnormal value determination condition, it may be determined whether or not the luminance values of the other colors or a luminance value of full color (white) but not the luminance value of blue B exceed the threshold value. It may be determined whether or not the luminance values exceed the threshold value with reference to the luminance values of blue or the other colors of four side edge portions in the rectangular predetermined range.

A third abnormal value determination condition senses an abnormal value due to leaf contamination, a flaw, and the other causes, obtains a standard deviation $\sigma$ of the RGB values and the Gray value from plurality of measurement results, and for example, determines a converted leaf color value as the measurement result, which exceeds a range of $2\sigma$, as abnormal. Furthermore, in the measurement of a leaf color value by using a leaf color scale or a chlorophyll meter, for example, there are many cases where ten rice plants are selected in one agricultural field, and a leaf color value of an unfolding second leaf is measured in each of the plants. Therefore, in the present embodiment, in a case where ten converted leaf color values are obtained by one measurement, the standard deviation $\sigma$ is obtained, and the abnormal value can be detected. In the detection, a case where any one of the RGB values and the Gray value exceeds the range described above is determined as abnormal. Alternatively, calculation values of only RG, calculation values of RGB, or a calculation value of only Gray may be determined.

Hereinafter, abnormal value determination processing will be described with reference to a flowchart of FIG. 33. Furthermore, the abnormal value determination processing, for example, is performed by the smart phone 1, and the camera 30 may have a function of performing the abnormal value determination processing. In the abnormal value determination processing, first, the number of times of measurement is set (step F1). As described above, in one measurement, for example, the measurement is performed ten times.

Next, measurement (imaging) of the camera 30 starts (step F2), and the imaging of the camera 30 is performed (step F3). Actually, the measurement starts, and an image signal or the like is sequentially input from the camera 30 in a state where the smart phone 1 side waits for the sequential input of the image signal from the camera 30. The input image signal is stored in the smart phone 1 side. Furthermore, in a case where the abnormal value is deleted and the measurement is performed again, the measurement result of the image signal or the like, which is the abnormal value, is deleted, and then, a new image signal is stored.

The values of R, G, B, and gray of each of the pixels in the predetermined range are calculated from the image signal, the average value as the representative value of each of the pixels is obtained, and thus, the color information is set, and the converted leaf color value is calculated from the color information (step F4). At this time, the color information and the converted leaf color value in the entire predetermined range are obtained, the color information and the converted leaf color values of four corner portions are obtained. Furthermore, for example, the average values of green G and gray may be obtained as the average value each of the pixels, and here, the average value (the representative value) of blue B is further obtained for determining the abnormal value. Furthermore, the average values of RGB may be calculated by the camera 30, or may be calculated by the smart phone 1.

Next, it is determined whether or not the converted leaf color values of four corner portions of the rectangular predetermined range in the imaging range exceed the predetermined upper limit value or the predetermined lower limit value (step F5).

In a case where the converted leaf color values do not exceed the upper limit value and the lower limit value, it is determined whether or not the average value of blue B exceeds a predetermined threshold value (step F6).

In step F5, in a case where the converted leaf color value of the corner portion of the image in the rectangular predetermined range exceeds the upper limit value or the lower limit value and in a case where the average value of blue B exceeds the predetermined threshold value in step F6, an error display is performed in the smart phone 1 (step F7). For example, the occurrence of the abnormal value is displayed on the display of the smart phone 1, and remeasurement is notified. The user basically repeats imaging until the set number of times of imaging ends, and in the case of being determined as abnormal in step F5 and step F6, the number of times of measurement is not counted up, an error is notified in step F7, the process proceeds to step 3, and the smart phone 1 waits for the input of the next image signal from the camera 30.

In a case where the color information of blue is determined as normal in step F6, the number of times of measurement is increased by 1, and it is determined whether or not the number of times of measurement becomes the set number of times described above (step F8). In a case where the number of times of measurement does not reach the set number of times, the process proceeds to step F3, and when an image signal based on the next imaging of the camera 30 is input, the image signal is stored, and the process proceeds to step P4.

In a case where the number of times of measurement reaches the set number of times in step F8, the standard deviation $\sigma$ of RGB values and the Gray value and the average value of all of the measured converted leaf color values are obtained (step F9), and then, for example, it is determined whether or not there is a converted leaf color value exceeding the range of $2\sigma$ from the average value of the converted leaf color value (step F10).

In a case where there is no converted leaf color value exceeding the range of $2\sigma$, the result is confirmed (step F11), and the measured converted leaf color value is registered in the smart phone 1 (step F12).

In addition, in a case where there is a leaf color value exceeding 2σ in step F10, an alarm representing that there is an abnormal value is displayed (step F13). Next, when the abnormal value is deleted, the user performs remeasurement or performs indication of intention by pressing a button or the like in order to obtain the measurement value instead of the abnormal value, and thus, it is determined whether or not the remeasurement is performed (step F14). In a case where it is determined that input representing that the user does not perform the remeasurement is performed, the process proceeds to step F12, and all of the measurement results are registered in the smart phone 1. Furthermore, the measurement result exceeding the range of 2σ described above may be excluded, or the user is asked whether or not to perform registration, and thus, the user may determine whether or not to perform registration. Furthermore, in the abnormality detection, in a case where any one of the RGB values and the Gray value exceeds the range, it is determined as abnormal. Alternatively, calculation values of only RG, calculation values of RGB, or a calculation value of only Gray may be determined.

In step F14, in a case where the user determines to select the remeasurement, for example, in the measurement results of the image signals or the like to which numbers are applied in order of measurement, the number of the measurement result which is determined as the abnormal value is input (step F15). Next, the process returns to step F3, and imaging is performed by camera 30. At this time, when the image signal or the like obtained by performing imaging is registered in the smart phone 1, the image signal, the color information, the leaf color conversion value, and the like, which become the abnormal value corresponding to the input number, are deleted.

According to such abnormality determination processing, even in a case where the user does not determine whether or not the measurement result is abnormal, it is determined whether or not there is an abnormal value in the smart phone 1, and the abnormal value is deleted, and thus, it is possible for the user who is difficult to determine the abnormal value to perform measurement with security. In addition, it is possible to exclude the abnormal value with a high probability, and thus, the reliability of the converted leaf color value as the measurement result increases, and a difference in the measurement result due to a difference in the measurer can be reduced.

Next, a fourth embodiment of the present invention will be described.

This embodiment describes a display method of the smart phone 1 of the converted leaf color value obtained as described above, in the plant information acquisition system or the crop management system described above. The camera 30 described above is connected to the smart phone 1 such that the image signal or the color information can be output. Furthermore, the color information may be calculated from the image signal on the smart phone 1 side.

FIG. 34 illustrates a display screen (a display device) 102 of the smart phone 1 in a state of performing imaging by using the camera 30, and in the display screen 102, the image signal output from the camera 30 is displayed on an imaged moving image display unit 103 as a moving image in the predetermined range described above, and image data which becomes a comparative target and is already obtained by performing imaging, is displayed on a comparative target display unit 104 on a lower side of the display screen 102 as a static image (a picture). In addition, as described above, imaging is continuously performed by the set number of times, and thus, the static image which is already imaged before the current imaging is displayed on the comparative target display unit 104. Here, for example, as described above, ten measurements (imaging) are performed at one time, and in FIG. 34, at the time of performing the seventh imaging, a static image, which becomes the sixth imaging result, is displayed on the comparative target display unit 104. Furthermore, the conversion value (the leaf color value) of the read value of the leaf color scale and the SPAD conversion value (the SPAD value) are displayed on a lower portion of the display screen 102. Therefore, the user is able to recognize the measurement result as a numerical value and a color. In addition, the agricultural field name in which the position of the agricultural field is registered in advance, and a symbol representing a section in the agricultural field are displayed on an upper side of the display screen 102. The agricultural field name and the symbol of the section are searched from the position according to the GPS function of the smart phone 1 and are displayed. Furthermore, not a color but a static image which is imaged may be displayed on the comparative target display unit 104.

In FIG. 35, in a case where the display screen 102 of the smart phone 1 of FIG. 34 is set to a screen in a normal mode, the display screen 102 is in a comparative mode, and a second comparative target display unit 105 is displayed in addition to the comparative target display unit 104. Other agricultural fields registered in an external database such as the smart phone 1 or the data management server 10, the color of color information (the representative values of the RGB values) of a different year, and an image can be displayed on the second comparative target display unit 105, and for example, an exemplary color in which the growth is excellent, the color of the state of the other agricultural field, and an image can be compared with the image of the current imaging. Furthermore, a color image of one color, which is in a solid coating state described above, for example, is obtained by displaying the average values (the representative values) of the RGB values calculated from the image data which is obtained by performing imaging at the time of obtaining the leaf color conversion value described above, as a color. In addition, data of the color which becomes the comparative target (the average values of the RGB values), for example, may be provided from a province autonomous community, an agricultural cooperative, or other organizations, or may be collected by an organization operating the management server 10 with the camera 30 of this embodiment.

In FIG. 36, a plurality of results measured in one measurement are displayed on a result display unit 106 of one display screen 102, and a plurality of conversion values (leaf color values) of the leaf color scale and a plurality of SPAD conversion values are displayed as the measurement result of each measurement, and correspondingly, the color information as the representative values of the RGB values described above are displayed as a color.

Accordingly, it is possible to confirm a set of measurement results by a numerical value and a color, and to confirm the measurement result by visual perception. Furthermore, in the result display unit 106, a measurement result which is considered as abnormal, can be manually changed by remeasurement, and the measurement result can be manually registered.

FIG. 37 illustrates the display screen 102 for comparing a plurality of measurement results with past measurement data or the like, which becomes the comparative target, by the static image (the picture), and in a data comparison unit 107 of the display screen 102 the static image is displayed on a measurement result display unit 108 with respect to each measurement result. In addition, the static image as the measurement data, which becomes the comparative target, is displayed on a comparative picture display unit 108*a*. Here, the static image which becomes the comparative target, for example, includes 1. the previous measurement result in the same agricultural field, 2. the measurement result of the same period in the past in the same agricultural field, 3. the measurement result of the same period in a different agricultural field, 4. the measurement result of the same period in a standard agricultural field of the section, 5. the measurement result of the same period in a practical farming family of the section, 6. a standard leaf color value which is recommended by the prefecture in the period, and the like. Furthermore, 6. is not a picture, but a color represented by the average values of RGB as described above. In addition, a color image of an average value obtained by further averaging the average values of RGB as each of the measurement results described above is displayed on an average result display unit 109, and an image of a color of the RGB values, which becomes a standard value, is displayed on a standard result display unit 110. The color which becomes the standard value, for example, is supplied from a public institution, and is color information which is considered as an optimal growth state in the present circumstances. Furthermore, the color or the converted leaf color value, which becomes the standard value, for example, may be based on the past result, an index which becomes a standard from the public institution, an average value of a crop in the region, a cultivation result of the excellent producer in the region, and the like.

In a method of obtaining the color, which is the average value of RGB described above, for example, in a case where the image data includes 32400 pixels (180 pixels×180 pixels) in total, and RGB values of each of the pixels are calculated, each luminance value of 32400 RGB in total is obtained. In a case where the total of each of the luminance values of RGB is divided by the number of pixels (32400 pixels), an average is obtained.

Furthermore, in the measurement result, in a case where the measurement data, which becomes the comparative target, is displayed as the color of the average value of RGB in the solid coating state as described above or in a case where the converted leaf color value is obtained from the average values of RGB and Gray as the measurement result, for example, in a case where the type or a manufacturer of the camera 30 is different, image processing is different, and thus, an image signal to be output is changed according to the process of the image processing, setting of parameters, or the like, in addition to the individual difference of the imaging sensor, the light source, the optical system, and the like. Therefore, it is preferable that the same type of camera 30 is used by being calibrated as described above in order to accurately perform comparison with respect to the color of a plant which becomes an imaging target or the converted leaf color value based on the color. In a case where the same type of camera 30 is not used, and a color chip of the same color is imaged as with the calibration described above, it is preferable to perform adjustment such that approximately the same average values of RGB can be acquired even by a different type of camera. Furthermore, a color to be displayed is changed according to a difference in the type of display, but a comparative display is performed by the same type of display, and thus, it is not necessary to adjust the image processing circuit or the like on the display side.

In FIG. 38, the measurement results of different periods, the measurement results of different spots, and the standard value described above are simultaneously displayed in chronological order, and thus, can be compared with each other. The converted leaf color value is displayed on a graph display unit 112 of the display screen 102 as a line graph by being divided into the measurement value and the standard value, and thus, the measurement value and the standard value can be compared with each other. In addition, similarly, the standard value and the measurement value are displayed side by side on a color comparison unit 113 as the color of the color information (the color of the average value of RGB) described above.

Accordingly, in a case where the measurement result and the standard value are displayed in chronological order, it is possible to determine whether the condition is excellent, is degraded, or is improved, from the graph and the color. In addition, in a case where the measurement result and the standard value are displayed corresponding to different spots, it is possible to determine whether or not the growth situation is excellent with respect to each of the spots, and to perform the fertilizer application management or the consideration of a countermeasure with respect to each of the spots.

EXAMPLES

Hereinafter, as examples of the present invention, a test performed for obtaining a multiple regression equation based on a correlative relationship between the values of RGB and Gray of image data obtained by performing imaging by the camera 30 and the SPAD value will be described.

As illustrated in FIG. 20, in test conditions, measurement was performed five times during approximately 50 days from Jun. 25, 2014 to Aug. 18, 2014, as a measurement period (a data period). Measurement days were five days of June 25, July 4, July 11, July 25, and August 18, and patterns measured only on July 11, July 25, and, August 18, which are the last half of the measurement period, were also set as the test conditions. A developing camera not including the receiving member 33 was used as a camera used in the measurement. The receiving member 33 was not provided, and thus, when the measurement was performed, it was necessary to press the tip of the hood 34 against a leaf in a state where the leaf was placed on a table, various stands, or the like, and a rice plant was not measured on site, and thus, the rice plant was sampled, and then, the imaging and the measurement of the SPAD value were performed in a building.

When the measurement was performed, a plurality of test sections were set in a plurality of rice paddies, and one rice plant, which became a representative, was sampled from each of the test sections. Furthermore, there is a case where the test section from which the rice plant as a sample was sampled and the number thereof are different a according to the measurement day. Ten stems were taken out from each of the rice plants, a center portion of a completely unfolding second leaf each of the stems was imaged by the camera, and thus, image data was acquired, and an SPAD value was measured on the same spot by using a chlorophyll meter. In the measurement of the SPAD value, SPAD-502Plus (manufactured by Konica Minolta, Inc.) was used. Therefore, in one test, ten leaves of one rice plant in each of the test sections were measured. In addition, in regression analysis, a data processing method includes a case where ten measurement values with respect to different leaves of one rice plant are directly used and a case where an average value is obtained as a representative value of the measurement values of ten leaves of one rice plant, and multiple regression analysis is performed by using the average value. Furthermore, as described above, a value which is generally used as the representative value, such as a center value or a mode value, can be used as the representative value.

In addition, four types of conditions described below were set as imaging conditions of the camera. Three white LEDs 42 were mounted on the developing camera, the imaging was capable of being performed in a two-lamp mode in which two lamps of the white LED 42 were turned on and a three-lamp mode in which three lamps were turned on, and in the imaging, imaging in the two-lamp mode and imaging in the three-lamp mode were performed. In addition, in the imaging, the leaf was disposed on a desk, the hood 34 was pressed against the leaf, the outside light was shielded, and the imaging was performed in a desktop pattern which was imaged by the illumination of the white LED 42 and a window watermark pattern which was imaged by both of the outside light transmitted through the leaf and the illumination of the white LED 42 by turning on the white LED 42 in a state where the leaf was pressed against a window by the hood 34. The window watermark pattern is affected by the outside light, and is imaged not only by the reflection light but also by both of the reflection light and the transmission light. Furthermore, the desktop pattern is imaged by the reflection light but not the transmission light.

In this example, a color mode (a color space) used in image analysis as an image analysis method was set to RGB+Gray and HSV+Gray. As described above, each of the values of RGB and the value of Gray or each of the values of HSV and the value of Gray of each of the pixels in the predetermined range of the image data obtained by imaging the leaf were set to an explanatory variable (the independent variable), and the SPAD value was set to an objective variable (the dependent variable), and thus, the multiple regression analysis was performed. Furthermore, the result of performing single regression analysis by using RGB+Gray as the color mode described above before the multiple regression analysis is performed, by using a two-lamp desktop as a measurement method, and by setting the SPAD value to the dependent variable and each of the values of RGB+Gray to one independent variable by using the average value of the measurement result of ten leaves of one rice plant, is illustrated in a graph of FIG. 21.

In the graph of FIG. 21, a horizontal axis is the SPAD value, and a vertical axis is each of the values (intensities) of RGB+Gray. In addition, a tetragonal dot is G, a rhomboidal dot is R, a trigonal dot is B, and a circular dot is Gray. In addition, in each straight line on the graph, the first straight line from the top represents a regression equation (a regression line) between G and the SPAD value, the second straight line from the top represents a regression equation (a regression line) between Gray and the SPAD value, the third straight line from the top represents a regression equation (a regression line) between R and the SPAD value, and the fourth straight line from the top represents a regression equation (a regression line) between B and the SPAD value.

In a case where the SPAD value is set to Y, and G is set to X, the regression equation is $Y=-0.0076X+0.47$, and the determination coefficient $R^2$ is 0.7892. In addition, in a case where Gray is set to X, the regression equation is $Y=-0.0054X+0.3289$, and the determination coefficient $R^2$ is 0.7719. In addition, in a case where R is set to X, the regression equation is $Y=-0.0035X+0.1794$, and the determination coefficient $R^2$ is 0.7461. In addition, in a case where B is set to X, the regression equation $Y=-0.0003X+0.0198$, and the determination coefficient $R^2$ is 0.0589. Furthermore, the determination coefficient $R^2$ is equal to the square of a correlation coefficient R, and is also referred to as a contribution rate. From the above description, in a case where each of the values of RGB+Gray is individually set to the independent variable, and the SPAD value is set to the dependent variable, the contribution rates of G and Gray are high, and the contribution rate of B is low.

Therefore, in a multiple regression equation of the multiple regression analysis, the multiple regression equation was prepared by setting only a variable having a strong correlation to the independent variable but not by setting all of the respective values of RGB+Gray to the independent variable. As illustrated in FIG. 22, the multiple regression analysis was performed by decreasing the independent variable one by one from four independent variables of RGB+Gray in four steps. That is multiple regression analysis using all of four independent variables was performed as step 1, multiple regression analysis using three independent variables by excluding an independent variable having the lowest absolute value of a t value representing a significance from four independent variables described above was performed as step 2, multiple regression analysis using two independent variables by excluding the independent variable having the lowest absolute value of the t value from three independent variables described above was performed as step 3, and regression analysis using one independent variable by excluding the independent variable having the lowest absolute value of the t value from two independent variables described above was performed as step 4.

In such four (multiple) regression analyses, an independent variable to be used is determined with reference to the correlation coefficient R, correction (a freedom degree-adjusted determination coefficient) $R^2$, and an explanatory variable selection standard Ru. The correction $R^2$ represents a contribution rate as with the determination coefficient $R^2$, and the determination coefficient $R^2$ tends to increase as the independent variable increases, whereas the correction $R^2$ is in consideration of the number of independent variables, and thus, is effective for determining an optimal independent variable. In addition, the freedom degree correct determination coefficient (the correction) $R^2$ is a value less than or equal to 1, which is less than the determination coefficient $R^2$, and can be a negative value.

In addition, the explanatory variable selection standard Ru is an index for determining whether or not the independent variable is an effective independent variable (the explanatory variable), and in a case where the multiple regression analysis is performed by combining each of the independent variables described above, it is possible to determine to the independent variable as effective as Ru increases. In addition, the t value described above represents the significance of the regression coefficient, obtained by dividing a coefficient illustrated in FIG. 24 by a standard error illustrated in FIG. 24, and indicates an influence rate with respect to the objective variable. In a case where an absolute value of the t value is less than 2, statistically, it is determined that the explanatory variable does not affect the objective variable. Theoretically, the t value is a value from negative infinity to positive infinity. It is indicated that incorporating the independent variable corresponding to the t value in the multiple regression equation is effective as the absolute value of the t value increases.

FIG. 23 illustrates each data item in a case where the multiple regression analysis is performed by setting the illumination in the test conditions illustrated in FIG. 20 to be in the two-lamp mode using two lamps of the white LED 42, by setting an imaging method to the desktop pattern in which imaging is performed by shielding the outside light on the desk, and by using the average value of ten measurements in the case of measuring ten leaves per one plant. The average value of R, the average value of G, the average value of B, and the average value of Gray of the image data as the measurement result, and the average value of the SPAD value measured by the chlorophyll meter are shown with respect to each of the measurement days and each of the test sections in which the sample is sampled. Furthermore, the average value of R (the R value), the average value of G (the G value), the average value of B (the B value), and the average value of Gray (the Gray value) are the average of each pixel in a predetermined range of image data obtained by performing imaging in one measurement, and are the average of ten measurements performed by using ten leaves.

FIG. 24 illustrates the result of performing the multiple regression analysis according to steps 1 to 4 illustrated in FIG. 22 by setting the SPAD value illustrated in FIG. 23 to the dependent variable and by setting the R value, the G value, the B value, and the Gray value to the independent variable. The multiple regression analysis was performed by using regression analysis of analysis tools of Microsoft Excel (Registered Trademark).

As illustrated in FIG. 24, as a result of performing the multiple regression analysis with four independent variables of the R value, the G value, the B value, and the Gray value, a value having the lowest absolute value of the t value representing the significance of each of the independent variables described above was the B value in the R value, the G value, the B value, and the Gray value. Therefore, in step 2, the B value was excluded, and the multiple regression analysis was performed with three independent variables of the R value, the G value, and the Gray value. In step 2, a value having the lowest absolute value of the t value was the R value. Therefore, in step 3, the R value, was excluded, and the multiple regression analysis was performed with two independent variables of the G value and the Gray value. In step 3, a value having the lowest absolute value of the t value was the Gray value. Therefore, in step 4, the regression analysis was performed by using the G value as the independent variable.

FIG. 25 illustrates combination patterns of four independent, variables used in steps 1 to 4 described above, and the correlation coefficient R, the correction (the freedom degree-adjusted determination coefficient) R2, and the explanatory variable selection standard Ru of (multiple) regression analysis of steps 1 to 4 in each of the patterns.

Here, as illustrated in FIG. 25, the correlation coefficient R is slightly high in the case of using four independent variables in step 1, and the correction R2 and the explanatory variable selection standard Ru are highest in the case of using two independent variables of G and Gray in step 3. In addition, the correlation coefficient R tends to be high as the number of independent variables increases, and thus, the correlation coefficient R in step 3 where the number of independent variables is 2, is slightly lower than the correlation coefficient R in step 1 where the number of independent variables is 4, but the t value of each of the independent variables is higher in step 3 than in step 1, and the significance each of the independent variables is higher in step 3 than in step 1. From the above description, in multiple regression analysis using a color space of RGB+Gray, the pattern of step 3 using two independent variables of G and Gray is adopted in which the number of independent variables is 2, which is less than 4, and the correction R2 and the explanatory variable selection standard Ru are highest. Furthermore, in the case of HSV+Gray, the multiple regression analysis was performed by using four variables of an H value, an S value, a V value, and the Gray value without optimizing the independent variable.

FIG. 26 illustrates the (multiple) determination coefficient $R^2$ and significance F in the multiple regression analysis using measurement results in different test conditions performed by combining the test conditions illustrated in FIG. 20. The significance F represents a probability that all coefficients of the regression equation are 0, and in a case where the significance F is approximately less than 5% (less than 0.05), it is possible to statistically represent that "all of the coefficients of the regression equation are not 0". In a case where the significance F is close to 0, the reliability of the regression equation increases as being close to 0.

In addition, FIG. 27 illustrates the (multiple) determination coefficient as a bar graph, corresponding to a graph horizontal axis name applied to each combination of the test conditions of FIG. 26. Furthermore, the significance F illustrated in FIG. 26 represents that the reliability of the regression equation is high in all of the test conditions.

In the (multiple) determination coefficient $R^2$, an HSV-two-lamp desktop (the average) on the first place from the top of FIG. 26 and on the first place from the left of the graph of FIG. 27, and an RGB-two-lamp desktop (the average) on the third place from the top of FIG. 26 and on the third place from the left of the graph of FIG. 20 represent high values. As illustrated in FIG. 26, in the HSV-two-lamp desktop (the average), the leaf is imaged on the desk in the two-lamp mode as described above, HSV+Gray are used as the variable of the color space, and an average value of ten measurement results is set to data of the multiple regression analysis.

In addition, in the RGB-two-lamp desktop (the average), the leaf is imaged on the desk in the two-lamp mode as described above, RGB+Gray are used as the variable of the color space, and the average value of ten measurement results is set to the data of the multiple regression analysis. Furthermore, in a case where RGB+Gray are used as the color mode, in the multiple regression analysis, only the value of G and the value of Gray are used as the independent variable as described above, and in a case where HSV+Gray are used, all of the value of H, the value of S, the value of V, and the value of Gray are used.

FIG. 28 illustrates multiple regression analysis results of the HSV-two-lamp desktop (the average) and the RGB-two-lamp desktop (the average). Basically, in the HSV-two-lamp desktop (the average) having many independent variables, the values of the correlation coefficient R, the determination coefficient $R^2$, and the correction $R^2$ are slightly large, and in the RGB-two-lamp desktop (the average), the number of independent variables is 2, and the t value of each of the independent variables is large, whereas in the HSV-two-lamp desktop (the average), the number of independent variables is 4, the independent variable is two times the independent variable of the RGB-two-lamp desktop (the average), and the t value each of the independent variables is small compared to the RGB-two-lamp desktop (the average).

As described above, as a result of performing the multiple regression analysis, it was possible to obtain a higher correlation coefficient compared to the single regression analysis.

In a case of the single regression analysis, the multiple determination coefficient $R^2$ was 0.6171 (conditions in which the color space was set to RGB, G was set to the independent variable, and the two-lamp desktop, a ten-point average, and all sections were set), whereas in the multiple regression analysis the multiple determination coefficient R2 was 0.87619 (conditions in which the color space was set to RGB, the independent variable was set to G and Gray, and the two-lamp desktop, the ten-point average, and all of the sections were set).

According to the multiple regression analysis of individual data, a result that a correlation between the average of each of 10 measurement points and the SPAD value was high was obtained. That is, it is considered that the height of a correlative relationship is in order of the average> the individual data, and in order of the two-lamp desktop> the three-lamp desktop> a three-lamp window watermark> a two-lamp window watermark.

Then, in the conditions where the two-lamp desktop, the ten-point average, and all of the sections were set, a high correlation coefficient was shown in HSV image analysis or RGB image analysis. As a result of comparing the HSV image analysis with the RGB image analysis, the t value in the RGB image analysis represents a high value (the influence rate is high). As described above, the number of variables in the RGB image analysis is small. That is, a high correlation coefficient is shown in a small number of variables, and thus, an influence rate of each factor (the independent variable) increases.

From the above description, the RGB image analysis was used in the conditions of the RGB-two-lamp desktop (the average) as the data used in the multiple regression analysis.

As this time, the multiple regression, equation (a correlation equation) is the SPAD value=−701.166x (the average value of G)+785.3087x (the average value of Gray)+68.92808. That is, the average value (the representative value) of G and the average value (the representative value) of Gray of the pixel s in a predetermined range of each of ten image data items obtained by imaging ten leaves by the camera 30 are obtained, the average values are set to the value of G and the value of Gray, and then, the average value (the representative value) of the values of G of ten image data items and the average value (the representative value) of the values of Gray of ten image data items are obtained, and the average value of G and the average value of Gray are substituted into the multiple regression equation, and thus, the SPAD conversion value (the converted leaf color value) is obtained. Furthermore, it is not necessary to perform the measurement ten times and to substitute the average value of ten measurement results into the correlation equation, and the number of times of measurement may be changed.

FIG. 29 illustrates a regression line obtained by performing regression analysis with respect to each SPAD conversion value as a calculation value, which is obtained by the multiple regression equation from the average value of G and the average value of Gray of the image data obtained in the conditions of the RGB-two-lamp desktop (the average) described above, and the average value of ten measurement results of the SPAD value measured by the chlorophyll meter at the time of performing the imaging by the camera 30 as described above.

A vertical axis represents the SPAD value (the SPAD conversion value) as a calculation result obtained from the multiple regression equation, and a horizontal axis represents the SPAD value as a measurement result of the chlorophyll meter. In addition, each dot represents the SPAD conversion value, which is the calculation result corresponding to ten leaves of the same rice plant, and the SPAD value as the measurement result.

As illustrated in FIG. 29, a correlation equation between the SPAD conversion value as the calculation result and the SPAD value as the measurement result was y=0.8762x+4.6772, and the determination coefficient $R^2$ was 0.8762. In FIG. 29, the shortest distance between the regression line and each of the dots was obtained as illustrated in FIG. 30. In FIG. 31, a horizontal axis represents the shortest distance of each of the dots from the regression line as the SPAD value of FIG. 29, a vertical axis represents the number of dots included in each of the sections in the case of separating the shortest distance described above by a range of 0.1, and a graph of FIG. 31 illustrates a frequency distribution.

In most dots, the shortest distance of each of the dots from the regression line is less than 2 in the SPAD value. Furthermore, the shortest distances of only three dots exceed 2. A measurement accuracy on the specification of the chlorophyll meter is ±1, whereas as described above, the shortest distance of each of the dots from the regression line is approximately less than or equal to 2, and thus, it is possible to indicate that the respective dots are distributed in a measurement accuracy range. That is, it is possible to increase the correlativity of the chlorophyll meter with respect to the SPAD value.

Furthermore, the color mode (the color space) to be used is not limited to RGB+Gray, and may be HSV+Gray as described above, or the other color spaces may be used. In addition, even in a case where a color space other than RGB+Gray, such as HSV+Gray, is used, as described above, the multiple regression analysis is repeated while sequentially decreasing the independent variable having the lowest t value in the multiple regression analysis. The independent variable used in the multiple regression analysis may be narrowed on the basis of the correct ion $R^2$ and the explanatory variable selection standard Ru which are rarely affected by the number of independent variables.

Furthermore, the numerical values relevant to the standard deviation σ, the threshold value, and the number of pixels of the image data, and other numerical values described in each of the embodiments and examples described above are not limited to the described values.

REFERENCE SIGNS LIST

1 smart phone (portable terminal: user terminal; control device: normal value sensing device)
10 management server
17 agriculture and fertilizer database (management information storage device)
30 camera (imaging device, plant information acquisition device)
33 receiving member (light shielding device)
34 hood (light shielding device)
40 lens (optical system)
41 imaging element (image sensor)
42 white LED (light source)
50 control circuit
51 image processing circuit (image processing device)
52 data processing circuit (image processing device)
53 communication circuit
101 plant information acquisition device
130 portable terminal

The invention claimed is:

1. A plant information acquisition system comprising:
an imaging element;
an illumination light source configured to illuminate a plant as an object;
an optical system including a lens focusing an image based on a reflected light of the plant illuminated by the illumination light source on the imaging element;

a first polarizing plate through which illumination light emitted from the illumination light source is transmitted;

a second polarizing plate through which reflection light of the plant is transmitted;

a light shielding device configured to shield outside light at the time of performing imaging by using the imaging element;

an image processing device configured to acquire color information representing a color of the plant on the basis of an image signal output from the imaging element; and a plant information acquisition device configured to acquire plant information from the color information on the basis of a correlative relationship between the color information and the plant information relevant to the plant which is correlated with the color information, wherein the first polarizing plate and the second polarizing plate are in a state where polarization directions of the first polarizing plate and the second polarizing plate are orthogonal to each other.

2. The plant information acquisition system according to claim 1, wherein the plant information is a numerical value which becomes an index of a content of a predetermined component contained in the plant, and the color information representing the color of the plant is represented by values of one or more types of variables among values of a plurality of types of variables configuring a color space of each pixel of image data obtained by performing imaging by the imaging element and is a representative value representing values of the variables respectively corresponding to a plurality of pixels in a predetermined range of the image data.

3. The plant information acquisition system according to claim 2, wherein regression analysis or multiple regression analysis is performed by setting the numerical value which becomes the index of the content of the predetermined component contained in the plant to a dependent variable and the representative value of the variable configuring the color space as the color information representing the color of the plant to an independent variable, and thus, a correlation equation for calculating the dependent variable from the independent variable is obtained, and the plant information acquisition device calculates the numerical value which becomes the index of the content of the predetermined component contained in the plant from the representative value as the color information on the basis of the image signal output from the imaging element by using the correlation equation.

4. The plant information acquisition system according to claim 2, wherein the plant information is a leaf color value which becomes the index of the content of chlorophyll as the predetermined component, and the color space includes red (R), green (G), blue (B), and gray (Gray), or hue (H), saturation (S), brightness (V), and gray (Gray), as the type of the variable.

5. The plant information acquisition system according to claim 1 comprising:

a plant information acquisition device including the imaging element, the optical system, the light source, the light shielding device, and the image processing device; and a portable terminal including the plant information acquisition device, wherein the plant information acquisition device is connected to the portable terminal to be capable of transmitting the color information.

6. The plant information acquisition system according to claim 5 comprising:

a server including a database in which information relevant to cultivation of the plant is stored, corresponding to the plant information, wherein the portable terminal is capable of being connected to the server such that data communication is capable of being performed with respect to the server through Internet by wireless communication, and in a case where the plant information is received from the portable terminal, the server extracts the information relevant to the cultivation of the plant corresponding to the received plant information from the database, and transmits the extracted information relevant to the cultivation of the plant to the portable terminal.

7. A plant information acquisition device which is provided in the plant information acquisition system according to claim 5, images the plant, and outputs the color information representing the color of the plant.

8. The plant information acquisition system according to claim 5, wherein the portable terminal is capable of being connected to a server such that data communication is capable of being performed with respect to the server through Internet by wireless communication, the portable terminal includes a transmitting device that transmits crop information including the plant information obtained by the plant information acquisition device to the server, and the server receives the crop information, includes management information storage device storing management information relevant to management of crop cultivation associated with the crop information, and transmits the management information which is extracted from the management information storage device on the basis of the crop information to the portable terminal.

9. The plant information acquisition system according to claim 8, wherein period information representing an acquisition period of the crop information and region information representing a region in which the crop information is acquired are included in information which is transmitted from the portable terminal and are received by the server, the management information storage device stores management information relevant to management of crop cultivation associated with the crop information, the period information, and the region information, and the server transmits the management information which is extracted from the management information storage device on the basis of received crop information, received period information, and received region information to the portable terminal.

10. The plant information acquisition system according to claim 9, wherein agricultural land information relevant to an area of an agricultural land in which the crop is cultivated is included in information which is transmitted from the portable terminal and is received by the server.

11. The plant information acquisition system according to claim 9, wherein the server extracts the management information stored in the management information storage device on the basis of the crop information, the period information, and the region information which are transmitted from the portable terminal, and in a case where information of an amount of applied fertilizer per unit area is included in the extracted management information, the management server calculates the amount of applied fertilizer of the agricultural land on the basis of the information of the amount of applied fertilizer and the agricultural land information transmitted from the portable terminal, and transmits the amount of applied fertilizer to the portable terminal.

12. The plant information acquisition system according to claim 1 comprising:

an abnormal value sensing device configured to set the color information or the plant information to an abnormal value in a case where the acquired color information or the acquired plant information satisfies an abnormal value determination condition which is set.

13. The plant information acquisition system according to claim 1 comprising:

a display device configured to display an image based on the image signal or the color information which is acquired from the image signal as a color; and a display control device configured to cause the display device to display the image or the color and to display a comparative image or a comparative color which becomes a comparative target.

14. The plant information acquisition system according to claim 13, wherein the color information is a representative value of each color of a value corresponding to each color of each pixel of an image in a predetermined range which is imaged by the imaging element.

15. The plant information acquisition system according to claim 1, wherein the image processing device is adjusted such that the plant information acquisition device is capable of acquiring the plant information which approximates to predetermined plant information, by using the optical system, the light source, and the light shielding device, at the time of imaging a calibration object corresponding to the predetermined plant information.

16. A plant information acquisition method using a plant information acquisition device including an imaging element, an illumination light source configured to illuminate a plant as an object, an optical system including a lens focusing an image based on a reflected light of the plant illuminated by the illumination light source on the imaging element, a first polarizing plate through which illumination light emitted from the illumination light source is transmitted, a second polarizing plate through which reflection light of the plant is transmitted, a light shielding device configured to shield outside light at the time of performing imaging by using the imaging element, and an image processing device configured to acquire color information representing a color of the plant on the basis of an image signal output from the imaging element, wherein the first polarizing plate and the second polarizing plate are in a state where polarization directions of the first polarizing plate and the second polarizing plate are orthogonal to each other, the method comprising:

acquiring plant information from the color information on the basis of a correlative relationship between the color information and the plant information relevant to the plant which is correlated with the color information.

17. The plant information acquisition method according to claim 16, wherein the plant information is a numerical value which becomes an index of a content of a predetermined component contained in the plant, and the color information representing the color of the plant is represented by values of one or more types of variables among values of a plurality of types of variables configuring a color space of each pixel of image data obtained by performing imaging by the imaging element and is a representative value representing values of the variables respectively corresponding to a plurality of pixels in a predetermined range of the image data.

18. The plant information acquisition method according to claim 17, wherein regression analysis or multiple regression analysis is performed by setting the numerical value which becomes the index of the content of the predetermined component contained in the plant to a dependent variable and the representative value of the variable configuring the color space as the color information representing the color of the plant to an independent variable, and thus, a correlation equation for calculating the dependent variable from the independent variable is obtained, and the numerical value which becomes the index of the content of the predetermined component contained in the plant is calculated from the representative value as the color information on the basis of the image signal output from the imaging element by using the correlation equation.

19. The plant information acquisition method according to claim 17, wherein the plant information is a leaf color value which becomes the index of the content of chlorophyll as the predetermined component, and the color space includes red (R), green (G), blue (B), and gray (Gray), or hue (H), saturation (S), brightness (V), and gray (Gray), as the type of the variable.

20. The plant information acquisition method according to claim 16, wherein the plant information is acquired, and then the information relevant to the cultivation of the plant corresponding to the plant information is extracted from a database in which the information relevant to the cultivation of the plant is stored, corresponding to the plant information.

* * * * *